(12) United States Patent
Fuksenko et al.

(10) Patent No.: US 11,694,802 B2
(45) Date of Patent: Jul. 4, 2023

(54) SYSTEMS AND METHODS FOR IMPROVING DISEASES DIAGNOSIS

(71) Applicant: OTraces, Inc., Rockville, MD (US)

(72) Inventors: Yuriy Fuksenko, Derwood, MD (US); Richard Saul, Gaithersburg, MD (US); Galina Krasik, Montgomery Village, MD (US); Mohsen Marefat, Silver Spring, MD (US); Keith Lingenfelter, Potomac, MD (US)

(73) Assignee: Otraces Inc., Rockville, MD (US)

( * ) Notice: Subject to any disclaimer, the term of this patent is extended or adjusted under 35 U.S.C. 154(b) by 284 days.

(21) Appl. No.: 16/072,000

(22) PCT Filed: Jan. 23, 2017

(86) PCT No.: PCT/US2017/014595
§ 371 (c)(1),
(2) Date: Jul. 23, 2018

(87) PCT Pub. No.: WO2017/127822
PCT Pub. Date: Jul. 27, 2017

(65) Prior Publication Data
US 2019/0027249 A1    Jan. 24, 2019

Related U.S. Application Data

(60) Provisional application No. 62/281,797, filed on Jan. 22, 2016.

(51) Int. Cl.
*G16H 50/20*    (2018.01)
*G16B 5/00*    (2019.01)
(Continued)

(52) U.S. Cl.
CPC ............... *G16H 50/20* (2018.01); *G16B 5/00* (2019.02); *G16B 5/20* (2019.02); *G16H 50/30* (2018.01); *G16H 50/50* (2018.01); *Y02A 90/10* (2018.01)

(58) Field of Classification Search
None
See application file for complete search history.

(56) References Cited

U.S. PATENT DOCUMENTS 6,058,322 A * 5/2000 Nishikawa ............ G06T 7/0012
382/128
7,604,956 B2   10/2009 Drukier
(Continued)

FOREIGN PATENT DOCUMENTS

CN    105005680 A    10/2015
CN    105209631      12/2015
(Continued)

OTHER PUBLICATIONS

Cun, Yupen—Thesis "Network-Based Biomarker Discovery: Development of Prognostic Biomarkers for Personalized Medicine by Integrating Data and Prior Knowledge"; *Dissertation zur Erlangung des Doktorgrades* Jan. 1, 2014 (Jan. 1, 2014).
(Continued)

*Primary Examiner* — Robert A Sorey
(74) *Attorney, Agent, or Firm* — Blank Rome LLP

(57) ABSTRACT

The present invention relates to systems and methods for improving the accuracy of disease diagnosis and to associated diagnostic tests involving the correlation of measured analytes with binary outcomes (e.g., not-disease or disease), as well as higher-order outcomes (e.g., one of several phases of a disease). Methods of the present invention use biomarker sets, preferably those with orthogonal functionality, to obtain concentration and proximity score values for disease and non-disease states. The biomarker set's prox-
(Continued)

imity scores are graphed on an orthogonal grid, with one dimension for each biomarker. The proximity scores and orthogonal gridding is then used to calculate a disease state or non-disease state diagnosis for the patient.

25 Claims, 29 Drawing Sheets

(51) Int. Cl.
  *G16H 50/30* (2018.01)
  *G16B 5/20* (2019.01)
  *G16H 50/50* (2018.01)

(56) References Cited

U.S. PATENT DOCUMENTS

| | | | |
|---|---|---|---|
| 9,952,220 B2 | 4/2018 | Michalek et al. | |
| 2003/0032017 A1* | 2/2003 | Anderson | G01N 27/44773 435/6.12 |
| 2004/0047493 A1* | 3/2004 | Rowe | A61B 5/117 382/128 |
| 2004/0121343 A1* | 6/2004 | Buechler | C12Q 1/6883 435/6.14 |
| 2005/0272110 A1* | 12/2005 | Drukier | G01N 33/60 435/7.93 |
| 2008/0133141 A1* | 6/2008 | Frost | G01N 33/6848 702/19 |
| 2008/0286776 A1 | 11/2008 | Young | |
| 2009/0234627 A1* | 9/2009 | Yu | A61N 5/1031 703/11 |
| 2009/0263827 A1* | 10/2009 | Johansen | G01N 33/6893 435/7.1 |
| 2011/0123976 A1* | 5/2011 | Raftery | G01N 33/68 548/321.5 |
| 2011/0178273 A1* | 7/2011 | Aabersold | G01N 33/6848 530/350 |
| 2012/0022793 A1 | 1/2012 | Baker et al. | |
| 2012/0132540 A1* | 5/2012 | Wang | G01N 27/3274 204/403.01 |
| 2012/0315641 A1 | 12/2012 | Dubinett et al. | |
| 2013/0261010 A1* | 10/2013 | Bailey | G01N 27/745 422/69 |
| 2013/0316374 A1 | 11/2013 | Penninger et al. | |
| 2013/0344111 A1* | 12/2013 | Roder | G16B 20/00 424/274.1 |
| 2014/0194304 A1* | 7/2014 | Shi | G01N 33/50 435/7.92 |
| 2014/0274794 A1* | 9/2014 | Speicher | C12Q 1/6886 435/23 |
| 2016/0034651 A1* | 2/2016 | Krasik | G16B 20/00 706/12 |
| 2017/0281725 A1 | 10/2017 | Sims et al. | |
| 2017/0372023 A1* | 12/2017 | Krasik | G16H 50/20 |

FOREIGN PATENT DOCUMENTS

| | | |
|---|---|---|
| JP | S60-209177 | 10/1985 |
| JP | 2011-528442 A | 11/2011 |
| WO | WO-2010009337 A2 | 1/2010 |
| WO | WO-2012037603 A1 | 3/2012 |
| WO | PCT/JP2012/514208 | 6/2012 |
| WO | WO-2014-149629 | 9/2014 |
| WO | WO-2014/158287 A2 | 10/2014 |
| WO | WO 2016/115511 A2 | 7/2016 |
| WO | WO-2017/127822 A1 | 7/2017 |
| WO | WO-2017127822 A1 * | 7/2017 ............... G16B 5/00 |

OTHER PUBLICATIONS

Borges et al.,"Building Multidimensional Biomarker Views of Type 2 Diabetes on the Basis of Protein Microheterogeneity," *Clinical Chemistry* 57:5 719-728. ; Jan. 1, 2011 (Jan. 1, 2011).
Song et al., "Identification of serum biomarkers for lung cancer using magnetic bead-based SELDI-TOF-MS," Acta Pharmacologica Sinica (2011) 32: 1537-1542.
Drukier et al., "High-Sensitivity Blood-Based Detection of Breast Cancer by Multi Photon Detection Diagnostic Proteomics," *Journal of Proteome Research*, 5(8) Aug. 1, 2006, 1906-1915, XP55350821.
Malik et al., "Soluble adhesion molecules and prediction of coronary heart disease: a prospective study and meta-analysis," *The Lancet*, Sep. 22, 2001, vol. 358; pp. 971-975.
International Preliminary Report on Patentability in International Application No. PCT/US2014/000041, dated Sep. 15, 2015.
International Search Report in International Application No. PCT/US2014/000041, dated Sep. 25, 2014.
European Search Report in EP Appln. No. 147765382, dated Mar. 9, 2017.
The International Search Report/Written Opinion for PCT/US/2018/46056 dated Oct. 26, 2018.
Nagalla, Srinivasa R., et al. "Proteomic analysis of maternal serum in down syndrome: identification of novel protein biomarkers." Journal of proteome research 6.4 (2007): 1245-1257.
Ahmed, Nuzhat, et al. "An approach to remove albumin for the proteomic analysis of low abundance biomarkers in human serum." Proteomics 3.10 (2003): 1980-1987.
Lokshin et al., "Multimarker assay for early diagnosis of ovarian cancer," American Association for Cancer Research, *Amer Assoc Cancer Res* 2006, 47: 653, CME: Disclosure.
Drukier et al., "Ultra-Sensitive Immunoassays Using Multi Photon Detection in Diagnostic Proteomics of Blood," *Journal of Proteome Research* 2005, 4:2375-2378.
Evaluation of HE4, CA125, risk of ovarian malignancy algorithm (ROMA) and risk of malignancy index (RMI) as diagnostic tools of epithelial ovarian cancer in patients with a pelvic mass; Mona Aarenstrup Karlsen, Noreen Sandhu, Claus Høgdall, Ib Jarle Christensen, Lotte Nedergaard, Lene Lundvall, Svend A.Engelholm, Anette T.Pedersen, Dorthe Hartwell, Magnus Lydolph, Inga Alice Laursen, Estrid V.S.Høgdall; Gynecologic Oncology, vol. 127, Issue 2, Nov. 2012, pp. 379-383.
Performance of a Multiplexed Dual Analyte Immunoassay for the Early Detection of non-small cell lung cancer; Victoria Doseeva, Tracy Colpitts, Grace Gao, Juliana Woodstock and Vladimir Knezevic, Journal of Translational Medicine, (2015) 13:55, DOI 10.1186/s12967-015-0419-y.
Woelfel et al., "Orthogonal Rotation to Theoretical Criteria," pp. 1-20.
Torgerson, Warrenton, "Multidimensional Scaling: I. Theory and Method", *Psychometrika*, vol. 17, No. 4, Dec. 1952.
Toss, Angela et al. "Molecular Biomarkers for Prediction of Targeted Therapy Response in Metastatic Breast Cancer; Trick or Treat?." *International Journal Of Molecular Sciences*, vol. 18, 1 85. Jan. 4, 2017, doi:10.3390/ijms18010085 (Year: 2017).
Office Action dated Mar. 29, 2023 issued in corresponding CN Application No. 201880065502.9.

* cited by examiner

FIGURE 29

| Protein | Serum Concentration Regulation Direction | Condition or Drug | Incidence Approx. |
|---|---|---|---|
| IL 6 | Up | Alcoholism | 10.00% |
| IL 6 | Up | Asthma | 10.00% |
| IL 6 | Up | Autoimmune disease | 10.00% |
| IL 6 | Up | Bacterial Infections | 0.50% |
| IL 6 | Up | Breast Cancer | 0.50% |
| IL 6 | Up | Cardiomyopathy | 0.01% |
| IL 6 | Up | COPD | 10.00% |
| IL 6 | Up | Major depressive disorder (MDD) | |
| IL 6 | Up | Pulmonary Hypertension | |
| IL 6 | Up | Rheumatoid arthritis | 2.00% |
| IL 6 | Up | Schizophrenia | 3.00% |
| IL 6 | Up | Viral Infections (cold flu etc.) | 8.00% |
| IL 6 | Up | Vaccines | 1.00% |
| IL 6 | Down | Certain Diets | |
| IL 6 | Down | Corticosteroids Drug | |
| IL 6 | Down | Flurbiprofen, Osteoarthritis Drug | |
| IL 6 | Down | Immune suppressive disease | |
| IL 6 | Down | Nonsteroidal anti-inflammatory drugs | |
| IL 6 | Down | Tiaprofenic acid, Osteoarthritis Drug | |
| IL 6 | Down | Valproic acid, epilepsy and bipolar disorder | |
| IL 8 | Up | Active inflammatory bowel disease | |
| IL 8 | Up | Alcoholism | 10.00% |
| IL 8 | Up | Breast Cancer | 0.50% |
| IL 8 | Up | Chronic sarcoidosis | |
| IL 8 | Up | Cushing's syndrome | |
| IL 8 | Up | Cystic fibrosis | |
| IL 8 | Up | Drug Reparixin | |
| IL 8 | Up | Gingivitis | |
| IL 8 | Up | Obesity | 30.00% |
| IL 8 | Up | Psoriasis | |
| IL 8 | Up | Pulmonary fibrosis | |
| IL 8 | Up | Sepsis | |
| IL 8 | Up | Thyroid diseases: goiter | |
| IL 8 | Up | Viral infections primarily Hepatitis | 0.02% |
| IL 8 | Up | Vaccines | 1.00% |
| IL 8 | Down | Corticosteroids Drug | |
| IL 8 | Down | Immune suppressive disease | |
| Kallikrein | Up | Breast Cancer | 0.50% |
| Kallikrein | Up | Alzheimer's disease | 5.00% |
| Kallikrein | Up | neural plasticity | |
| Kallikrein | Up | Psoriasis | |
| Kallikrein | Up | Skin desquamation | |
| Kallikrein | Up | Tooth development | |
| TNFα | Up | Alcoholism | 10.00% |
| TNFα | Up | Alzheimer's Disease | 0.50% |
| TNFα | Up | Autoimmune disease | 10.00% |
| TNFα | Up | Breast Cancer | 0.50% |
| TNFα | Up | Graves Disease | |
| TNFα | Up | HIV | |
| TNFα | Up | Major depressive disorder (MDD) | |
| TNFα | Up | Psoriasis | |
| TNFα | Up | Severe heart failure | |
| TNFα | Up | Severe Septic Shock | |
| TNFα | Up | Some Parasites (malaria) | |
| TNFα | Down | Antibiotics Some | |
| TNFα | Down | Flurbiprofen, Osteoarthritis | |
| TNFα | Down | Nonsteroidal anti-inflammatory drugs | |
| TNFα | Down | Tiaprofenic acid, Osteoarthritis | |
| TNFα | Down | Valproic acid, epilepsy and bipolar disorder | |
| VEGF | Up | Age-related macular degeneration | |
| VEGF | Up | Asthma | 10.00% |
| VEGF | Up | Breast Cancer | 0.50% |
| VEGF | Up | Diabetes mellitus | 10.00% |
| VEGF | Up | Embryonic development | |
| VEGF | Up | Heart disease | 40.00% |
| VEGF | Up | Muscle following exercise | High |
| VEGF | Up | New blood vessels after injury | 2.00% |
| VEGF | Up | New vessels (collateral circulation) to bypass blocked vessels | |
| VEGF | Up | Rheumatoid arthritis | 2.00% |
| VEGF | Up | Simvastatin Drug | 10.00% |
| VEGF | Up | Stroke | 1.50% |
| VEGF | Down | Anti-angiogenesis treatment for cancer Drug | |
| VEGF | Down | Dilative but not ischemic cardiomyopathy | |
| VEGF | Down | Secondary progressive multiple sclerosis | |
| VEGF | Down | Thalidomide treatment for MS Drug | |

| Legend - Markers Regulated per Condition or Drug |
|---|
| One marker per Condition |
| Two markers per Condition |
| Three markers per Condition |
| All Five markers per Condition |

SYSTEMS AND METHODS FOR IMPROVING DISEASES DIAGNOSIS

This application is a national stage application of International Application No. PCT/US2017/014595, filed Jan. 23, 2017, which claims priority to U.S. Patent Provisional Application No. 62/281,797, filed Jan. 22, 2016, the entire disclosures of which are hereby incorporated by reference.

A related patent application, PCT/US2014/000041, filed Mar. 13, 2014, (hereby incorporated by reference in its entirety herein) describes methods for improving disease prediction using an independent variable for the correlation analysis that is not the concentration of the measured analytes directly but a calculated value termed "Proximity Score" that is computed from the concentration but is also normalized for certain age (or other physiological parameters) to remove age drift and non-linearities in how the concentration values drift or shift with the physiological parameter (e.g., age, menopausal status, etc.) as the disease state shifts from not-disease to disease.

FIELD OF THE INVENTION

The present invention relates to systems and methods for improving the accuracy of disease diagnosis and to associated diagnostic tests involving the correlation of measured analytes with binary outcomes (e.g., not-disease or disease), as well as higher-order outcomes (e.g., one of several phases of a disease).

BACKGROUND OF THE INVENTION

Diagnostic medicine has long held promise that proteomics, the measurement of multiple proteins with a correlation to the disease state, would yield breakthrough diagnostic methods in diseases for which research heretofore has not produced simple viable blood tests. Cancer and Alzheimer's are just two. A major problem has, in large part, boiled down to protein (or other biomolecule) concentration measurements of samples that are contaminated with factors related to other conditions or drugs (prescribed or not, e.g., alcohol), or that reflect geographic and environmental influences on biomolecule concentration measurements. Within a large population with known disease and not-disease states that would be used as the basis of a model to assess the correlation, there exists hundreds if not thousands of the conditions or drugs that affect up or down regulation of the biomarkers of choice. Furthermore, biological systems exhibit complex non-linear behaviors that are very difficult to model in a correlation method.

BRIEF DESCRIPTION OF THE FIGURES

A more complete appreciation of the invention and many of the attendant advantages thereof will be readily obtained as the same becomes better understood by reference to the following detailed description when considered in connection with the accompanying figures, wherein:

FIG. 29 shows a table with the various conditions or drugs that affect up or down regulation of the proteins used in the breast cancer detection panel.

SUMMARY OF THE INVENTION

The conventional wisdom in older proteomic methods is that the "truth" is in the raw concentration values measured, and their practitioners come from a biology or clinical chemistry background. In contrast, the methods of the present invention divert completely away from the notion that "truth" is in these raw concentration values, and is based on a deeper interpretation of what the concentrations mean, as discussed below. These dramatically improve the performance of regression methods, the neural network solution, render the Support Vector Machine mute, and bring other more powerful correlation methods forward. The solution comes in part from the mathematics of measurements and rejection of random noise. All measurements consist of the desired signal and noise. Mathematics proves that the noise can be eliminated by multiple sampling of the desired signal. The noise will be separated by such sampling into correlated noise (in sync with the measurement sampling scheme) and uncorrelated or random noise. The random noise is reduced by the square root of the number of samples. The signal and correlated noise (called offset) can be deduced very accurately by this multiple sampling. Finally, the offset can be determined with measurements in the absence of signal. These methods are used, for example, in transmissions of pictures from spacecraft with very low wattage transmitters from beyond the orbit of Pluto, in the presence of noise hundreds or thousands of times larger the desired signal.

Figure 1:
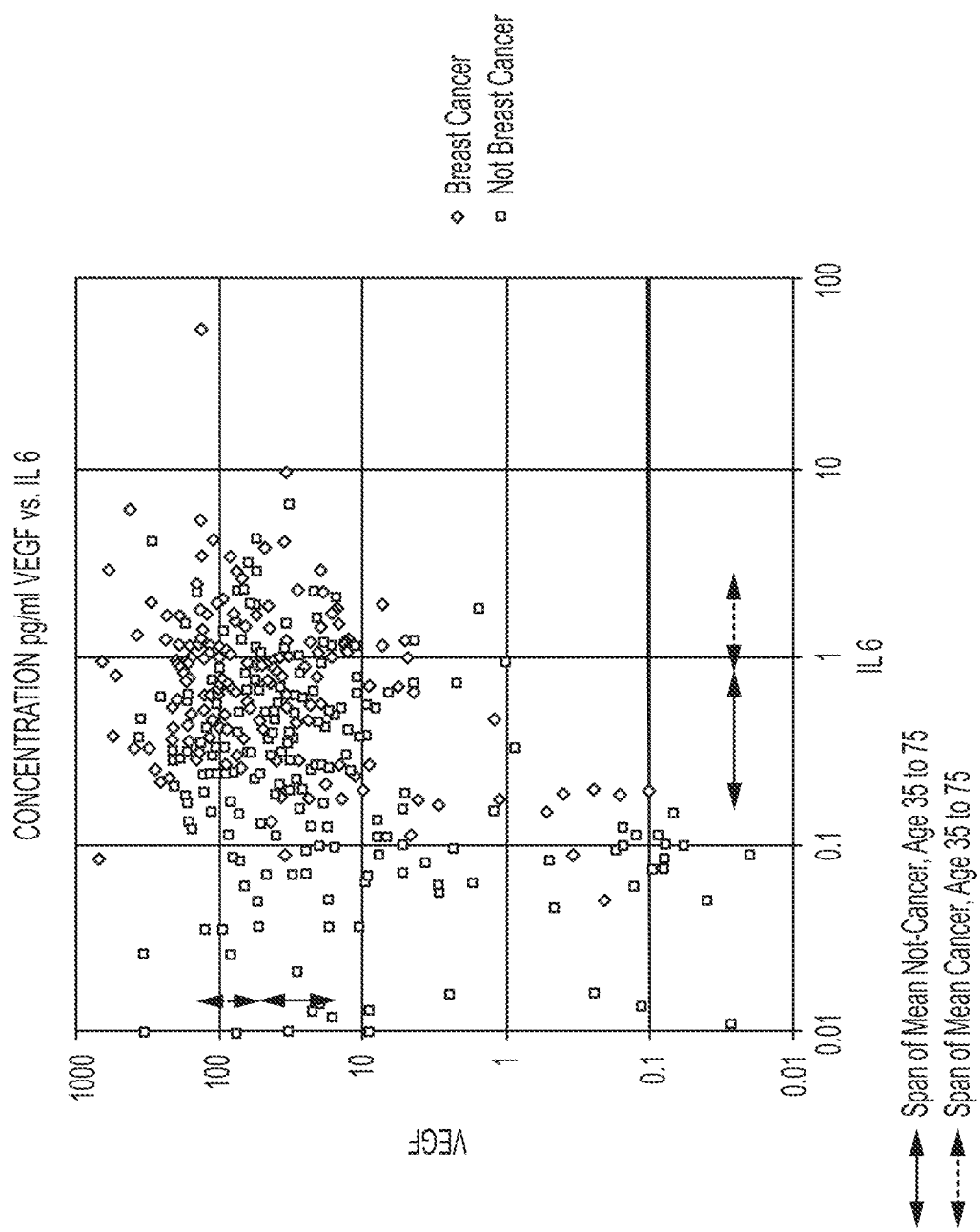
FIG. 1 shows two typical, IL 6 and VEGF, important biomarkers in 400 women that have been diagnosed with breast cancer (red) or not (blue).

In the case of proteomics, the noise is fixed in time for any one sample (individual tested for disease). Persons skilled in the art will understand that the methods of the present invention may be applied to the evaluation of all types and classes of biomarkers and biomolecules, although proteins and proteomics are used for convenience in much of the following discussion. The diagnosis must be made now, not after months of sampling. Thus, a somewhat different strategy must be used, and the information returned is somewhat different than the spacecraft case, but the underlying mathematics is the same. In the proteomics case, many hundreds of different sample measurements from individuals within known groups, disease and not-disease, are taken to determine the mean values of the signal (disease) and offset (not-disease). The accuracy of these parameters is only limited by the number of samples taken. Once these mean values are determined, some rationality can begin to be applied to the FIG. 1 plot. This method cannot fully determine the accurate values for disease or not-disease, for an individual as the "noise" for any given sample is fixed in time. However, a brief thought experiment illustrates that this parameter is not only not useful but is non-existent. For example, an individual must get disease to try to measure the "mean value" for disease, and the not-disease mean value has no meaning for one sample. A baseline could be measured over a long time for just that individual, but it would also be contaminated with the proteomics variances noted above. Certainly the management of the knowledge of these variances would be easier in one individual. However, the disease mean value would need to be again based upon a large population survey. The useful information in this case is the mean values for the population in general, and these means can then be used to place unknown samples into the correct "bucket," disease or not-disease, by processing the raw concentrations as explained below.

The present application describes improvements to previous techniques. For instance, this invention teaches how to apply the age or other physiological parameters noted in application No. 61/851,867 as a meta-variable. Additionally, this invention teaches why there is a need for and how to suppress proteomics variance. Accordingly, this application discusses using noise suppression methods transplanted from the physical sciences and mathematics to dampen information embedded in proteomics that contaminates the proteomics concentration measurements and confounds the ability to maximize correlation predictive power. This contamination is variances in the concentration measurements caused, for example, by a plethora of conditions or drugs that the individual patients may be on or may have been on. In the case of cancer, these conditions are non-malignant but functionally still contaminate samples and affect biomarker levels and noise in both the cancer and not-cancer patients. These conditions or drugs cause variances in the concentration measurements that would be normally associated with the condition of interest, such as breast cancer, for example. The variances are ubiquitous, and obtaining knowledge about the magnitude of them in one individual to correct them is impossible. This patent discusses how to dampen or eliminate these variances.

This application also discusses using certain biomarkers with specific functionality. These include: cytokines, whose functionality, primarily but not totally as signaling proteins, are in certain groups; immune system inflammatory markers, anti-tumor genesis, cell apoptosis and tumor vascularization and angiogenesis markers as well as known tumor tissue markers. These biomarkers are active in disease and indeed are active in cancer. They are either reactions of the immune system to the presence of the tumor or the tumor's action on the body. In effect, these biomarkers measure the micro-environment around the tumor, or the immune systems actions to kill the tumor or the tumors actions to survive and grow. Additionally, these biomarkers have complimentary functionality. That is complimentary to the correlation analysis. These biomarkers greatly improve predictive power when analyzed using a multi-dimensional Spatial Proximity or the Support Vector Machine correlation method (also called neighborhood search or cluster analysis). These biomarkers have functionality that are complimentary when viewed on the orthogonal multi-dimensional axes used in this correlation method. That is, the orthogonality improves separation and thus predictive power. A method for using these biomarkers to improve predictive power is discussed below. This improvement in predictive power is achieved by using a correlation method that retains orthogonal separation (e.g., a correlation method based spatial orientation of the biomarkers).

The method for damping or suppressing the variances embedded in proteomics based concentration measurements uses mathematical concepts used in electronics and communications to suppress noise. In the case of proteomics, the process of disease detection starts with collecting sample sets known to have the disease and not have the disease. The collected sample sets can include blood samples, plasma samples, urine samples, tissue samples, other biological samples, and the like. The collected sample sets are called the training set. These are then correlated to the two states, not-disease or disease, via a correlation algorithm. This process is degraded by proteomics variances. Random noise is suppressed in the measurement physics realm by applying the notion that random noise is 90 degrees out of phase with the sample measurements. This mathematically reduces to the random noise by an amount proportional to the square root of the number of measurement samples taken. The Proteomic Variances are caused by numerous conditions and drugs and may be completely unrelated to the condition of interest for diagnosis that they can be considered uncorrelated to the measurement of interest. Thus, they can be suppressed using techniques described in this application.

Much cancer biomarker research focuses on tumor markers. The CLIA lab test for lung cancer, PAULA's Test, for example, uses 4 tumor markers and one antibody to tumor markers in its test panel. The issue with this strategy is that if one tumor marker is included in the test panel, a second tumor marker for the same tumor could be redundant and thus does not add as much useful predictive power information as a functional protein. This application discloses a better strategy for selecting biomarkers for cancer.

Commonly, correlation methods use logistic or linear regression or methods that are intended to maximize area under Receiver Operator Characteristic (ROC) curves with multiple parameters to maximize predictive power. Many of these methods achieve about 80% predictive power. The discussion below describes the claimed invention and a method where biomarkers that are not normally associated with cancer detection are used. These biomarkers are generally considered to have an insufficiently specific reaction to the cancer to be useful. Described is a method that uses orthogonal Spatial Proximity correlation techniques where the biomarkers are selected due to the orthogonality of their functions. That is, their functions do not interact. Using multiple tumor markers would seem to force adding up predictive power. However, we show that using biomarkers not specifically associated with cancer that are within certain groups; immune system inflammatory markers, anti-tumor genesis, cell apoptosis and tumor vascularization and angiogenesis circulatory markers as well as a single known tumor tissue marker can produce predictive power far better than just tumor markers. Using these groups can narrow the number of possible conflicting conditions that would represent false positive test results to very low levels. Furthermore, the cancer has been shown herein to cause these biomarkers to react in a highly specific way, yielding very high test sensitivity.

Indeed, the present invention resolves many problems in the art. For example, methods in the art destroy or wipe out much information containing the biological measurements. The concentration measurements invariably span many (5 or more) orders of magnitude. These ranges are compressed and forced upon the averaged mean values, and focused into zones that are fixed by these mean values. Information in the highly non-linear behavior of the signaling proteins used in these analysis is wiped out. Far-out or outlier data is forced to "look" like ordinary data near the mean values.

The present invention addresses this issue as follows. In a large group of known samples with disease and not-disease, there are only two pieces of useful information for answering the diagnosis question, the mean values of disease and the mean values of not-disease. All other information can be suppressed as discussed in this application. Conventional wisdom in biology is that the information in raw concentration values or limited variations on this (e.g., logarithm of concentration) are meaningful in determining the accuracy (truth) of a disease—not-disease diagnosis. The notion that a log/log plot of two biomarkers is dominated by mostly Proteomic Variances (noise) has been unnoticed or seemingly counter to current knowledge.

Another deficiency is the art is that one could have a sample with cancer (up regulated inflammatory) and an immune suppression condition (down regulated) and thus this sample may have a low pro-inflammatory response, thus forcing these samples' pro-inflammatory "behavior" into the Not-cancer bin.

The present invention resolves the foregoing issue by including other signaling proteins that illuminate other actions of the tumor and the immune system. This method of forcing them into their respective "grouping" zones will tend to help mask the above-described situation. To the extent that the immune suppression conditions are included in the not-cancer training group this situation, and many similar situations will be mitigated. This is true of all the other functional parameters used in this method. False positives will result only when a not-disease condition exactly mimics the disease condition. In the case of cancer, we can find only multiple abnormal not-cancer conditions that could mimic cancer. For example, men with BPH (PSA elevated), an auto-immune disease (IL 6 and TNFs elevated) and a condition where strong vascularization is triggered, severe wounds (IL8 and VEGF elevated) will mimic the disease. Furthermore, this situation of duplicate conditions that force the inflammatory response both up and down will be present no matter how one approaches the correlation. The method of the claimed invention suppresses its influence, where others may simply try to correlate to the not-disease and disease trend lines (e.g., logistic regression of concentration values).

Another example of a deficiency in the art is that the average values of the biomarkers for either the disease or not-disease for a single sample are the same as they are for the group mean values.

If these parameters are known for a single isolated sample, they may well do better at the task of detecting a not-disease to disease transition. But the fact is these parameters are not measured routinely (year by year) for patients and in fact they are not measured at all today. Furthermore, it is not possible to determine the individual mean value for the disease state until the individual gets the disease. Thus, this determination of forcing them to look like group mean values is the valuable strategy for making such diagnoses today. The notion of recording these parameters year in year out for an isolated patent (for just not-disease) may well be ultimately a better approach to solving the problem. Without this personal pattern of biomarker behavior, attempting to know the true mean value of disease and not-disease is not only impossible for a single individual but is irrelevant. The only information of value is the group behavior of the disease in the population, mean values for not-disease and disease.

The present invention relates to true random noise, not noise that is correlated to a function or action, especially where this function or action has a relationship to the signal. Thus, it cannot work in proteomics when the so-called extraneous information is actually actions by these signaling proteins necessary for organism function. In those cases, the noise is not random but correlated to some unknown function.

These measured concentration levels are indeed related to organism actions or reactions, however, they need not be totally unrelated (and random) compared to the signal. The action of measuring correlated noise theoretically forces the other component of noise to be uncorrelated. Furthermore, there are many hundreds of conditions that drive actions of these proteins and the presence of any one or more in several hundred samples used in the training set renders their possible correlated error zero.

In summary, many practitioners would be concerned about the concentration information lost when implementing these techniques to zero out the extraneous information. However, contrary to conventional techniques, the inventors have developed analytical approaches for which the only useful information in a population where one desires to determine whether a blind sample is in the not-disease or disease group, is the mean value of the groups in the general population. To be sure, there is additional information in the raw measured data. For example, if the training set also has cancer stage information for each cancer case, and it is desired to determine whether the cancer stage is 0 or higher, the average mean value of the population for stage 0 and the average value of all stages above 0 are of use. In this case, the training set model will consist of cancer samples grouped into two groups: 1) stage 0; and 2) stage 1 and up. If the mean values for these groups are different, then a predictive power will result if the information extraneous to the mean values are again zeroed out within the model. The mean values for this case (cancer stage) are different than the case for cancer detection, and the model reduces difference information.

It is contemplated that more than one analyte will be necessary to provide sufficient separation between the disease and not-disease states when creating or utilizing an evaluative model that indicates a probability of a disease state in a patient under examination. Persons skilled in the art will understand that multiple analytes make that separation more accurate, and would typically employ two, three, four, five, six or more analytes.

DETAILED DESCRIPTION OF THE PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose. Several preferred embodiments of the invention are described for illustrative purposes, it being understood that the invention may be embodied in other forms not specifically shown in the figures.

For the purposes of this application, for ease of understanding, the following definitions are utilized:

"Analyte" refers to the chemical compound of interest for measurement. In a proteomics case, an analyte is a protein, and the method of measurement is usually an immunoassay. The unit of measurement is the concentration noted in mass units per unit volume of the biological fluid or tissue being sampled. The concentration value is related to a medical diagnostic procedure. Analyte would be considered a more general term for "Biomarker." Analyte could be a compound such as glucose found in the blood of patients and in the outside world, as well as a protein found generally only within the blood of a patient. These terms could be used interchangeably in this document, unless specific differences are discussed.

"Analytical Sensitivity" is defined as three standard deviations above the zero calibrator. Diagnostic representations are not considered accurate for concentrations below this level. Thus, clinically relevant concentrations below this level are not considered accurate and are not used for diagnostic purposes in the clinical lab. Measurements at the level of Analytical Sensitivity statistically are at a 99.7% confidence level.

"Baseline Analyte Measurement for an Individual" is a measurement set of the biomarkers of interest for the transition of an individual patient from the not-disease state to the disease state, measured for a single individual multiple times over a period of time. The Baseline Analyte Measurement for the not-disease state is measured when the individual patient does not have the disease, and alternatively, the Baseline Analyte Measurement for the disease state is determined when the individual patient has the disease. These baseline measurements are considered unique for the individual patient and may be helpful in diagnosing the transition from not-disease to disease for that individual patient. The Baseline Analyte Measurement for the disease state may be useful for diagnosing the disease for the second or higher occurrence of the disease in that individual.

"Bi-marker" is a set of two of the Proximity Scores that are normalized and functionally related to a meta-variable's variation with respect to the biological transition from a non-disease to a disease state when plotted in a two axis graph (or grid), and referred to below as "bi-marker planes."

"Biological Sample" means tissue or bodily fluid, such as blood or plasma, that is drawn from a subject and from which the concentrations or levels of diagnostically informative analytes (also referred to as markers or biomarkers) may be determined.

"Biomarker" or "Marker" means a biological constituent of a subject's biological sample, which is typically a protein or metabolomic analyte measured in a bodily fluid such as a blood serum protein. Examples include cytokines, tumor markers, and the like. The present inventors contemplate that other biological indicia can be used in the methods of the present invention, such as height, eye color, geographic factors, and/or other measurements or attributes that vary within a population(s) and are measurable, determinable or observable.

"Blind Sample" is a biological sample drawn from a subject without a known diagnosis of a given disease, and for whom a prediction about the presence or absence of that disease is desired.

"Closest" refers to the distance of a training set point from the grid location being scored. The distance for a two dimensional grid would be the hypotenuse of the coordinate distances from the grid location to the training set point. For higher dimensions, the distance would be the square root of the sum of squares of the distances. The closest training set points would be the ones that have the least value of this distance, to the grid location being scored.

"Disease Related Functionality" is a characteristic of a biomarker that is either an action of the disease to continue or grow or is an action of the body to stop the disease from progressing. In the case of cancer, a tumor will act on the body by requesting blood circulation growth to survive and prosper, and the immune system will increase pro-inflammatory actions to kill the tumor. These biomarkers are in contrast to tumor markers that do not have Disease Related Functionality, but are sloughed off into the circulatory system and thus can be measured. Examples of Functional Biomarkers would be Interleukin 6 which turns up the actions of the immune system, or VEGF which the tumor secretes to cause local blood vessel growth, whereas a non-functional example would be CA 125, a structural protein located in the eye and human female reproductive tract and has no action by the body to kill the tumor or action by the tumor to help the tumor grow.

"Biomarker Movement Action" is the movement of the above defined Disease Related Functional biomarker when concentrations or Proximity Scores are plotted on orthogonal axes. Further, if these Disease Related Functional biomarkers have orthogonal functionality, they will progress away from or toward the origin of a multi-dimensional plot where each axis represents the measured concentration or a proxy for this measured value (e.g. Proximity Score). This movement causes not-disease to disease separation in the plot and will dramatically improve the predictive power.

"Fine enough to be Suitable for Diagnosis" indicates that the divisions of the plotting grid have enough granularity to clearly differentiate a not-disease indication from a disease indication and to score the unknown samples with enough granularity that medical judgments of probability of disease are possible. The diagnosis may be for medical matters of some importance other than just not-disease versus disease, such as the internal breakdown of the disease state, including cancer stage or symptomless versus symptomatic Lyme's disease. A person skilled in the art can readily determine when the granularity is sufficient (e.g., a medical doctor).

"Isolated Point" is a training set data point from a single patient that is far isolated from other training set data points. When grid points near these points are scored for not-disease versus disease by proximity, they will unduly influence these surrounding points with the diagnosis of this isolated point. The system and method of the pending application addresses this undue influence. The best figure of merit for the process of improving this isolated point problem is the standard deviation of the multi-dimensional space of the training set data points on the grid. We find a standard deviation of 7 or more yields poor results and 3 or less yields much better results, that is, the accuracy of the correlation. Of course, these values are relative and may be somewhat different for other examples.

"Limit of Detection" (LOD) is defined as a concentration value 2 standard deviations above the value of the "zero" concentration calibrator. Usually, the zero calibrator is run in 20 or more replicates to get an accurate representation of the standard deviation of the measurement. Concentration determinations below this level are considered as zero or not present for example, for a viral or bacterial detection. For purposes of the present invention, 1.5 standard deviations can be used when samples are run in duplicate, although the use of 20 replicates is preferred. Diagnostic representations requiring a single concentration number are generally not rendered below this level. Measurements at the level of Limit of Detection statistically are at a 95% confidence level. Predictions of disease state using the methods discussed here are not based upon a single concentration and predictions are shown to be possible at measurements levels below the concentration based LOD. "Low Abundance Proteins" are proteins in serum at very low levels. The definition of this level as used in this specification includes a level less than about 1 picogram/milliliter in blood serum or plasma and other body fluids from which samples are drawn.

"Low Abundance Proteins" are proteins in serum at very low levels. The definition of this level as used in this application presently includes a level less than about 1 picogram/milliliter in blood serum or plasma and other body fluids from which samples are drawn.

"Mapping" is an operation that associates each element of a given set (the domain) with one or more elements of a second set (the range). In this case, the mapping associates the measured concentration values (domain) to the Proximity Score (the range).

"Meta-variable" means information that is characteristic of a given subject, other than the concentrations or levels of analytes and biomarkers, but which is not necessarily individualized or unique to that subject. Examples of such meta-variables include, but are not limited to, a subject's age, menopausal status (pre-, peri- and post-) and other conditions and characteristics such as pubescence, body mass, geographic location or region of the patient's residence, geographic source of the biological sample, body fat percent, age, race or racial mix, or era of time.

"Normalizing the Concentration-Age Shift" refers to removing inherent age related shifting of the not-disease to disease transition in concentration measurements. This "normalizing" action removes the age factor that degrades (by smearing out) the correlation of concentration to disease transition. This normalization is embodied in the "Proximity Score" variable.

"Normalizing the Midpoint Value of Concentration" refers to the value of concentration measurements that is the average of the two mean values for disease and not-disease. This parameter drifts with age. When mapped to Proximity Score the age drift of the concentration measurements is removed.

"Population Distribution" means the range of concentrations of a particular analyte in the biological samples of a given population of subjects. A specific "population" means, but is not limited to: individuals selected from a geographic region, a particular race, or a particular gender. And the population distribution characteristic selected for use as described in this application further contemplates the use of two distinct subpopulations within that larger defined population, which are members of the population who have been diagnosed as having a given disease state (disease subpopulation) and not having the disease state (non-disease subpopulation). The population can be whatever group in which a disease prediction is desired. Moreover, it is contemplated that appropriate populations include those subjects having a disease that has advanced to a particular clinical stage relative to other stages of disease progression.

"Population Distribution Characteristics" are determinable within the population distribution of a biomarker, such as the mean value of concentration of a particular analyte, or its median concentration value, or the dynamic range of concentration, or how the population distribution falls into groups that are recognizable as distinct peaks as the degree of up or down regulation of various biomarkers and meta-variables of interest are affected by the onset and progression of a disease as a patient experiences a biological transition or progression from the non-disease to disease state.

"Predictive Power" means the average of sensitivity and specificity for a diagnostic assay or test, or one minus the total number of erroneous predictions (both false negative and false positive) divided by the total number of samples.

"Proximity Score" means a substitute or replacement value for the concentration of a measured biomarker and is, in effect, a new independent variable that can be used in a diagnostic correlation analysis. The Proximity Score is related to and computed from the concentration of measured biomarker analytes, where such analytes have a predictive power for a given disease state. The Proximity Score is computed using a meta-variable adjusted population distribution characteristic of interest to transform the actual measured concentration of the predictive biomarker for a given patient for whom a diagnosis is desired.

"Slicing the Multi-Dimensional Grid" is useful for reducing the computation time needed to build the model. In this case, the multi-dimensional space, 5 dimensions, is cut into 2 dimensional slices along each set of orthogonal axes. This yields 10 "bi-marker planes" for the 5 dimensional case (6 dimensions would yield 15 planes). The training set data is then plotted on each plane, and the planes are again cut up into grid sections on each axis. Each bi-marker plane is thus a projection of the full multi-dimensional grid on the bi-plane.

"Topology Instability" is an area on the grids of the bi-marker planes where the points in the area are sitting on steep slope sections of the topology. The topology is the shape of the multi-dimensional correlation computation that takes all of the measured independent variables (that is, the determined biomarker concentrations) and the meta-variable into account. This topology, for a single value of the meta-variable, is at least five dimensions for a five biomarker measurement (it can be more). The topology also shifts in shape as the meta-variable changes in value. This multi-dimensional topology can be visualized by eye in pieces by taking ten bi-plane slices through the topology. This renders the calculated disease scores "at risk" of being wrong due to measurement noise. The score can be derived by weighting the individual bi-marker plots for predictive power to the disease and non-disease state, and by taking into account other factors such as topology measurement instability and simple measurement error. The score range can be arbitrary, and the value represents a percent probability of the patient being in the disease or non-disease state.

"Training Set" is a group of patients (200 or more, typically, to achieve statistical significance) with known biomarker concentrations, known meta-variable values and known diagnosis. The training set is used to determine the axes values "Proximity Scores" of the "bi-marker" planes as well as score grid points from the cluster analysis that is used to score individual blind samples.

"Training Set Model" is an algorithm or group of algorithms constructed from the training set that allows assessment of blind samples regarding the predictive outcome as to the probability that a subject (or patient) has a disease or does not have the disease. The "training set model" is then used to compute the scores for blind samples for clinical and diagnostic purposes. For this purpose, a score is provided over an arbitrary range that indicates percent likelihood of disease or not-disease or some other predetermined indicator readout preferred by a healthcare provider who is developing a diagnosis for a patient.

"Incongruent Training Set Model" (or "Secondary Algorithm") is a secondary training set model that uses a different phenomenological data reduction method such that individual points on the grids of the bi-marker planes are not likely to be unstable in both the primary correlation training set model and this secondary algorithm.

"Spatial Proximity Correlation Method" (or Neighborhood Search or Cluster Analysis) is a method for determining a correlation relationship between independent variables and a binary outcome where the independent variables are plotted on orthogonal axes. The prediction for blind samples is based upon proximity to a number (3, 4, 5 or more) of so called "Training Set" data points where the outcome is known. The binary outcome scoring is based upon the total distance computed from the blind point on the multi-dimensional to Training Set points of opposite outcome. The shortest distance determines the scoring of the individual blind data point. This same analysis can be done on bi-marker planes cut through the multidimensional grid where the individual bi-marker plane score is combined with the score of the other planes to yield a total. This use of cuts or two dimensional orthogonal projections through the space can reduce computation time.

"Orthogonal Functionality" is a term used in this description of the method that applies to low level signaling functions such as adaptor, effecter, messenger, modulator proteins, and the like. These proteins have functions that are specific to a body's reaction to the disease or the disease's action on the body. In the case of cancer, these are generally considered to be immune system actors such as inflammatory, or cell apoptosis and vascularization functions. One tumor marker is considered to be orthogonal to the extent that it does not also represent a specific signaling function. The marker should be selected as best as possible to be independent of the others. In other words, varying levels on one should not interact with the others except as the disease itself affects both. Thus, if variations in one orthogonal function occur, these changes in and of themselves will not drive changes in the others. Vascularization and inflammatory functions would be considered orthogonal in that proteins can be selected that primarily perform only one of these functions. These proteins, when plotted on the multi-dimensional Spatial Proximity grid, will act independently, and if the disease causes actions of both, they will amplify predictive power. Many cytokines have multiple interacting functions, thus the task is to select functions and the proteins such that this interaction is limited. The degree of "functional orthogonality" is a relative matter, and in fact it can be argued that all cytokines interact to some degree. Many have severely overlapping functions and many do not. Interleukin 8 is implicated in both pro and anti-inflammatory actions as well as angiogenesis. In a disease such as cancer, it is primarily the circulatory action, but other existing conditions within the organism may well be driving actions of this cytokine, contributing to the Proteomic Variance. The choice of best biomarkers with functional orthogonality is at best a compromise depending on the conditions being diagnosed.

"Individual Proteomic Variance" as used in this application includes the notion that proteomic test results, concentration measurements, by definition, contain a plethora of information that is not related to or helpful in diagnosing any particular condition or disease of interest. This variation is caused by hundreds of conditions that affect up or down regulation of the proteomic biomarkers of interest. These biomarkers can have very high correlation to and in fact a causal relation to the disease. These unrelated conditions affect the biomarkers and mask or contaminate the information about the disease of interest making the disease to not-disease correlation difficult. This variance, though not random noise per se, can be likened to random noise in that it is uncorrelated to the condition of interest, such as breast cancer, for example, and screening diagnosis of this cancer. Thus, actual information about the screening diagnosis can be accurately extracted by sampling many individual samples and determining the mean value of each biomarker for just the breast cancer. The mean value of the opposite condition, not-breast cancer, can also be determined to a degree of accuracy by measuring many such known not-breast cancer samples. See *The Complexity Paradox* (Kenneth L. Mossman, Oxford University Press, 2014), where the challenges faced by Proteomic Investigators are aptly summarized: "the non-linear dynamics inherent in complex biological systems leads to irregular and unpredictable behaviors."

"Signal (Disease) or Null Offset (Not-Disease Mean Values)" is defined as the mean value measured over a sufficiently large population to effectively dampen or remove the Proteomic Variance (noise) defined above. The definition of the cohort within which to measure these parameters is important. The signal (disease) mean value will be determined by medical sciences to truly have the condition. The condition may be a defined disease or a subset of those with the disease with a specific characteristic that may be of interest in treatment. It may be the disease proper (e.g., breast cancer, or it may be a characteristic of the disease, cancer stage, or the aggressiveness of the tumor's growth). The Null Offset (Not-Disease) also must be carefully defined based upon what conditions the diagnosis needs to separate. In the case of screening for disease, the population of people that generally present for health screening would be appropriate. This would preclude samples that just suffered trauma injury, for example, but would include conditions that affect the population of screening age, and most importantly the biomarkers in use. The signal (disease population) will also be infected with this proteomic noise. The Null offset (not-disease) may be the opposite within the disease group that does not have the sub condition of interest (e.g., for prostate cancer, this may be the non-aggressive form of the disease). Again, the mean values of both of these parameters must be pre-determined by medical science diagnosing the condition to determine accurate mean values.

"Proteomic Mean Value Separation" determines if the biomarkers of interest can actually separate the two conditions of interest signal (disease) or Null Offset (not-disease). If the mean values are measured accurately in a known population and they have separation (are different in value), then diagnostic predictive power will be achieved.

"Proteomic Variance Suppression" is the method whereby the aforementioned Proteomic Variance (noise) is suppressed. This suppression is done first on the known group of samples, termed the training set. The goal is to condition the concentration values of the training set samples such that they agree with the medically determined diagnosis. The mathematical methods are limited only by the goal of forcing the predictive scoring of the predictive model to agree with the known samples. The method may involve compression, expansion, inversion, reversal, folding portions of measured variables over onto itself producing a function where multiple inputs (concentrations) produce the same output (Proximity Score). The reasons for this are several (see below population distribution bias) and include the purpose of damping the variance "noise." Also, look up tables or similar tools can be used for the transformation, and for other mathematical schemes. This same noise suppression method, when applied to blind or validation sample, will produce this same noise suppression. The result after the transformation is called the Proximity Score. Suppression of proteomics variance is the mathematical transformation that eliminates or suppresses the variation not correlated with the conditions of interest, in this case not-breast cancer and breast cancer defined by the mean values of both as measured in a large known population of each.

Referring now to the drawings, FIG. 1 shows two typical, IL 6 and VEGF, important biomarkers in 400 women that have been diagnosed with breast cancer (red) or not (blue). It is a 2 dimensional plot of two biomarkers, Interleukin 6 and VEGF used in the breast cancer proteomics diagnostic method described in this document. The plot is a logarithmic plot of the raw, as measured, concentrations of these biomarkers. The red data points are diagnosed as having cancer by biopsy. The blue data points are a representative population of women who present for yearly screening mammography. No effort was extended to eliminate any non-malignant condition or disease state in this population. The red and blue arrows show the span over concentration of the mean values for breast cancer and not-breast cancer by age for each biomarker. In other words, the mean value of breast cancer concentration of IL 6 spans from about 0.9 pg/ml to about 2.1 pg/ml over the age range of 35 to 75 years of age. The data is for about 400 women 50% cancer and 50% not-cancer and the measurements were taken at the Gertsen Institute in Moscow, Russian Federation, using the OTraces CDx Immunochemistry System and the OTraces BC Sera Dx breast cancer test kit.

This plot is typical of hundreds of such plots with other biomarkers where the two states, not-disease and disease are poorly discriminated. In fact, this poor discrimination is endemic across all biomarkers. There is some upward regulation of the biomarkers as the women transition from not-disease to disease, but the transition is clearly not crisp. The problem with this plot is that most, if not all, of the women in the plot have many conditions unrelated to breast cancer, some possibly known but mostly not known. Many are on prescribed drugs that also affect up or down regulation of these cytokines. Thus, the plot is contaminated or noisy with unknowable information that confounds the correlation of these concentrations to the disease transition. In *The Complexity Paradox* (Kenneth L. Mossman, Oxford University Press, 2014), the challenges faced by Proteomic Investigators are aptly summarized: "the non-linear dynamics inherent in complex biological systems leads to irregular and unpredictable behaviors."

Proteomics research has tended to approach this problem by applying big computation methods to try to maximize the separation between disease and not-disease states. These have tended to be in two categories, neural networks, and what are called Support Vector Machines. Computational intelligence techniques in bioinformatics; Aboul Ella Hassanien, Eiman Tamah Al-Shammari, Neveen I. Ghali; Computational Biology and Chemistry 47 (2013) 37-47. The Neural Network strategy is to put "neural" nodes between the inputs, biomarker concentration, and the outputs, disease and not-disease. There are generally enough nodes such that each input has a unique pathway to each output through the "neural" nodes. The big computation then attempts to solve the correlation problem by assigning gain or attenuation (within the neural node) to each pathway for each input to each output. Support Vector Machines work by passing curved planes or surfaces through the biomarker plot space. These surfaces or planes are curved, folded, bent, shifted and rotated through all possible, unique solutions, looking for the curved surface that has the best separation power. The methods all use what is called a Training Set with known outcomes to try to put intelligence into the complexity. The theorem is that if the Training Set produced Model gets it correct, the Model will get unknown samples from the general population correct. These methods have not been able to cut through the complex mess typified in the FIG. 1 plot.

The first step is to reconcile what can be known about the FIG. 1 plot for breast cancer. There are only four useful pieces of information in the plot. They are the mean values of the two biomarkers for both not-breast cancer and breast cancer. Beyond these mean values, we can rank each individual sample by its relationship to the means. There are only four ranks, 1) the individual sample is less than the mean value for not-breast cancer; 2) greater that this value but less than the derived mid-point mean value between the breast cancer/not-breast cancer means; 3) above this mid-point of the means and below the mean value for cancer; and 4) above the mean value for breast cancer. Any information beyond this for individual samples is not useful and can be considered noise.

The problem is further displayed in the table shown in FIG. 29. This table shows various conditions or drugs that affect up or down regulation of the proteins used in the breast cancer detection panel. This table must be considered a very limited survey and, in fact, there are likely many conditions or drugs (prescribed or not e.g., alcohol) not known that affect these protein concentrations in serum. Note that for just IL 6 and VEGF, there are 35 listed. It is interesting to note the legend below the table. Yellow highlight indicates conditions or drugs that affect two of the proteins, tan indicates three, and light red indicates four or more affected proteins. Only breast cancer affects four or more and in fact all five are affected.

Some physicists may object to the use of the term "noise" as noise is usually considered random. The proteomics noise discussed here is caused by generally unknowable actions of conditions, drugs, environmental factors or individual variations (e.g., genetic variations, etc.). The "noise" can also be termed "Proteomics Variance." However, since the conditions that cause these variances are so numerous and randomly distributed in the population, they can rightly be considered uncorrelated, or like random noise, and thus treated as such. This means that information contained in very far outlier concentrations measured in some samples, for example, is useless information and can be damped (crushed mathematically).

There is a significant complication in this ranking and noise damping process. That is, the mean values vary dramatically with age. Thus, the mathematical method of placing these samples by rank, 1 through 4 above, must also sort out the age drift problem. This problem can be bad enough that the not-disease mean values will overlap the disease mean values at different ages in some cases. A new independent variable based upon the age related rank and the damping of noise is called for. We term this new variable the "Proximity Score." The Proximity Score must encompass above noted attributes including: 1) be anchored by the means for disease and not-disease; 2) normalize (zero out) age drift in the disease transition; 3) force ranking of the individual samples by their relationship to the means; and 4) mathematically dampen or compress the outlier noise in samples far from the means. In addition, the clustering behavior of the raw concentrations in the far out or outlier "noisy" samples must be retained to apply this to the spatial relation retaining correlation methods discussed below. The relationship of the Proximity Score to raw concentration may actually be inverted if the related correlation performance is improved.

Figure 2:
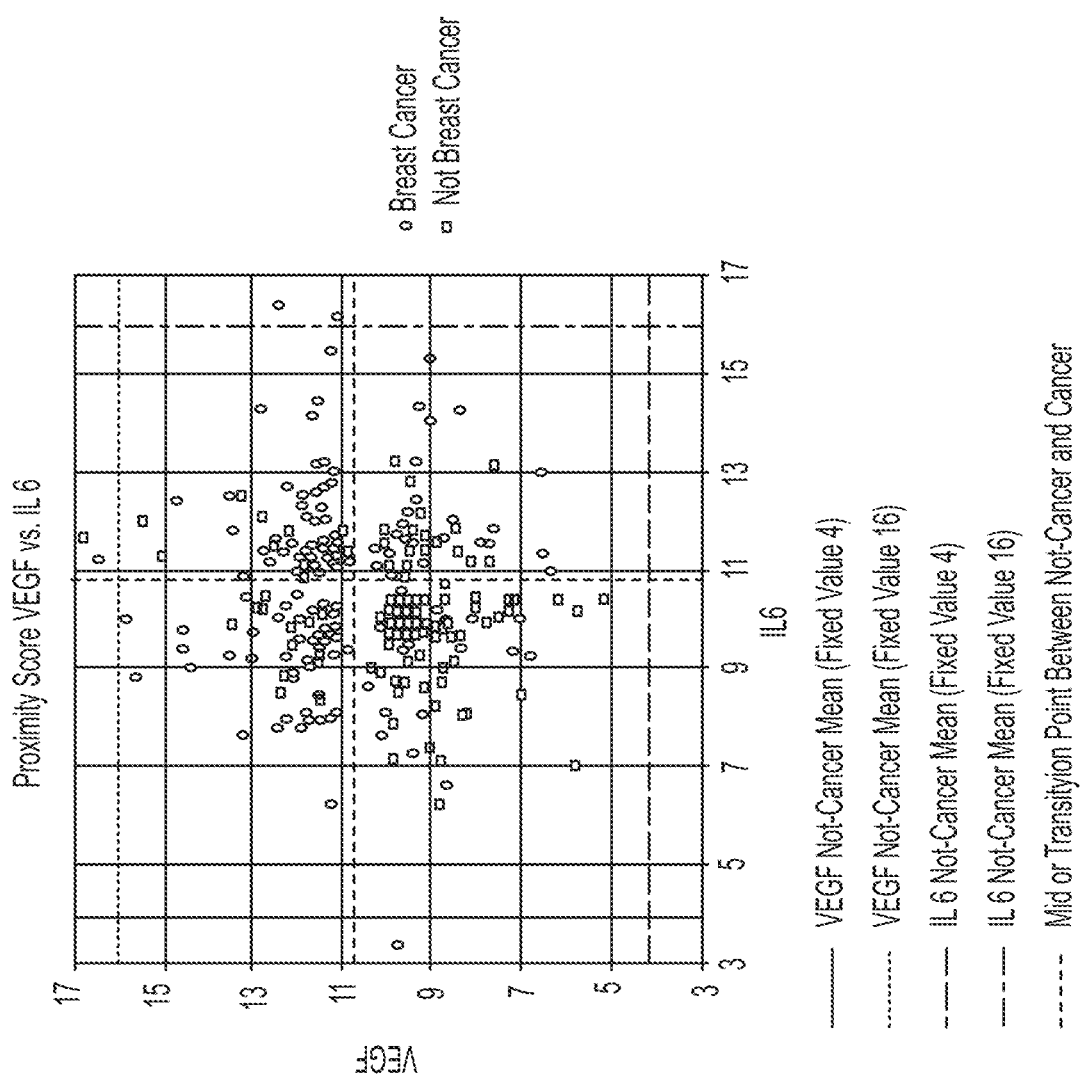
FIG. 2 shows the Proximity Score plot for the same two biomarkers for 400 women shown in FIG. 1 for IL 6 and VEGF.

FIG. 2 shows the Proximity Score plot for the same two biomarkers for 400 women shown above in FIG. 1 for IL 6 and VEGF. It is a plot of the same 400 women shown above in FIG. 1 after processing through the OTraces Proteomics Computation Engine that performs the analytical steps described herein. This computation converts raw concentration into Proximity Score. The mean values for not-breast cancer and breast cancer are now normalized at 4 and 16 respectively and the midpoint or not-cancer to cancer transition point is fixed at slightly less than 11. Each individual data point shown in FIG. 1 is now forced to be placed in zones that are anchored by the Proximity Score Means and each point keeps its relationship to its age adjusted mean concentration value respecting the age of the sample. The not-breast cancer and breast cancer means are now fixed at Proximity Scores of 7 and 15 for both biomarkers respectively. Proximity Scores for this example were chosen to range from 0 to 20, however, other ranges can be chosen. Also, the individual sample data points are forced into the ranking (1 through 4) zones inside the fixed mean values. At a fixed Proximity Score of 11, both biomarkers are at their derived mean point between the not-breast cancer and breast cancer means. These fixed points at Proximity Scores of 5, 11 and 17 are all normalized for age. Thus, a raw sample exactly at the concentration of either of the means or the mid-point between the means at that samples age will get the Proximity Score of 5, 11, or 17 respectively, regardless of age. Of course, the scoring range and fixed or normalized points are arbitrary. All other individual samples including far outliers are compressed into the space between the means, and each raw concentration value is forced to the proper side of the mid-point of the means by its raw concentration's relationship to the means and mid-point of the means. Note also that zones 1 and 2 may overlap in the dimensional plot as can 3 and 4 for best separation. However, 1 & 2 and 3 & 4 cannot overlap at all.

Transformations discussed above work well for the not-breast cancer to breast cancer transition. In fact, the folding of very far outliers into the space between is unique to situations where the normal population of disease to not-disease is far from equal (see discussion below). Other transformation methods may be indicated for other distributions of raw concentration distributions. The method is directly related to the nature of the raw data distributions and the character of the disease state distribution, and is a factor derived from the model building process, not from first principles. However, the mean value anchoring is important along with the forced ranking with respect to the mean values.

When these new independent variables are applied to various correlation methods according to the present invention, the results are considerably improved. Note that most of the raw concentration data have now been transformed to place them between the new fixed mean values for not-breast cancer and breast cancer. The reason for this will be discussed below. Table 1, shown below, demonstrates the improvements in predictive power, and more improvements are discussed below. As can be seen from the Tables, simply converting to the Proximity Score from raw concentration improves regression methods by 5%, and neural networks by 7%. Support Vector Machines yields 10%. Another correlation method called Spatial Proximity Correlation has similar improvement as the Support Vector Machine method. The Spatial Proximity Correlation method will be discussed further below, but it should be noted that this method actually renders the Support Vector Machine moot. The Support Vector Machine is a mathematical method designed to find the optimal correlation separation surface between two states where the mixing of the training set data for the two states is high and this optimal surface is not discernible visually. The Support Vector Machine functions as a binary linear classifier that maps points in space with as large a separation (surface) as possible. The computation methods described herein will produce this separation by damping the aforementioned noise. The systems and methods of the claimed invention reduce the planes of best separation into places on the multi-dimensional plot that one can see with the eye, such as the midpoint at Proximity Score of 11 in the FIG. 2 example.

TABLE 2

| Data Manipulation Method | Correlation Method | Predictive Power | Improvement Over Baseline |
| --- | --- | --- | --- |
| Logarithm of Raw concentration | Logistic Regression | 80% | Baseline |
| Logarithm of Raw concentration | Neural Network | 84% | 4% |
| Logarithm of Raw concentration | Surface Vector Machine | 84% | 4% |

TABLE 2-continued

| Data Manipulation Method | Correlation Method | Predictive Power | Improvement Over Baseline |
| --- | --- | --- | --- |
| Conversion of Concentration to Proximity Score | Logistic Regression | 85% | 5% |
| Conversion of Concentration to Proximity Score | Neural Network | 87% | 7% |
| Conversion of Concentration to Proximity Score | Surface Vector Machine | 90% | 10% |
| Conversion of Concentration to Proximity Score | Spatial Proximity | 90% | 10% |
| Conversion of Concentration to Proximity Score plus Orthogonal Biomarkers | Spatial Proximity | 96% | 12% |
| Plus Correction of Blind Samples for Topology Instability | Spatial Proximity | 96% Plus | 12% plus |

The evidence shows that predictive power improvements are much more enhanced by focusing on up/down regulation clustering in biomarker multi-dimensional space than following data trending in the information in the concentration measurements, especially after the conversion to Proximity Score from raw concentration. Regression methods and neural networks focus on data trends and cannot retain any spatial separation information. The Support Vector Machine and Spatial Proximity method captures this spatial separation information, discussed more below, and on clustering of the proteomics data.

In this breast cancer example, these biomarkers have selected functions that are immune system actors on the cancer or biomarkers of the cancer's actions (generally vascularization for tumor growth) on the organism that are as best as possible to be independent of the other biomarker functions. In other words, varying levels on one should not interact with the others except as the disease itself affects the others. Thus, if variations in one orthogonal function occur, these change in and of themselves will not drive changes in the others. These proteins have functions that are specific to the body's reaction to the disease or the disease's action on the body. In the case of cancer, these are generally considered to be active proteins such as inflammatory, cell apoptosis and vascularization functions. Many cytokines have multiple interacting functions. Thus, the task is to select functions and the proteins such that this interaction is limited.

This functional orthogonal action of these proteins (or other biomarkers) can easily be seen when they are plotted on orthogonal axes if Proteomics Variation is suppressed. If they up regulate in the transition to disease, the movement will be obvious to the eye that the disease state positions of the biomarkers in the dimensional grid move away from the ordinate. This information in this dimensional movement is dramatically enhanced by the conversion to Proximity Score (in fact, when using other analytical techniques, the contamination by Proteomics Variances almost completely obscures this information). However, this information is lost when the regression or neural network correlation methods are used.

This information is captured when a dimensional grid is used intrinsic to the correlation method. Support Vector Machine methods capture this as does the Spatial Proximity method. As noted above, the Support Vector Machine method is rendered moot by the conversion to the Proximity Score. In FIG. 2, the surface of maximum separation for best correlation is at about Proximity Score 11, the derived midpoint of the means, for both biomarkers. If one were to run the Support Vector Machine on this Proximity Score plot, one would just confirm the eye's recognition of the proper plane of best separation, wasting computer computation time and energy. Thus the best possible use with these complex functional cytokines includes functional orthogonality coupled with the Spatial Proximity Correlation method, which yields improvements in predictive power. Note also that the Support Vector Machine does not specify how the actual correlation weighting is done, just the planes of maximum separation in the multi-dimensional plot. Spatial Proximity focuses first on clustering of the data then on data trending in the transition from not-disease to disease.

The Spatial Proximity method, applied in an embodiment of the invention, includes a multi-dimensional space, one for each biomarker. The Proximity Score for each biomarker in the Training Set is plotted in the multi-dimensional space (5 dimensions in this breast cancer example). The plot is broken up into a grid, and then each point in this five dimensional grid is scored breast cancer or not-breast cancer by its closest proximity to several (15 to 20) Training Set points on the grid. The score is rendered by the count of breast cancer and not-breast cancer in the local vicinity of the empty grid point being scored. Maximum score is achieved in the empty grid point when it "sees" only breast cancer and vice-versa for not-breast cancer. Unknown samples are then placed on this grid and scored accordingly. Table 1 shows that combining this functional orthogonal selection of biomarkers with the Proximity Score Conversion (noise reduction and age normalization) yields predictive power of 96% for these biomarkers in this breast cancer case.

There are three problems with the Spatial Proximity Correlation method that must be dealt with: (1) population distribution local bias; (2) spatial density local bias; and (3) topology instability. Problems (1) and (2) may be dealt with in the conversion to Proximity Score, while problem (3) is handled through the correlation of unstable blind samples.

Figure 3:
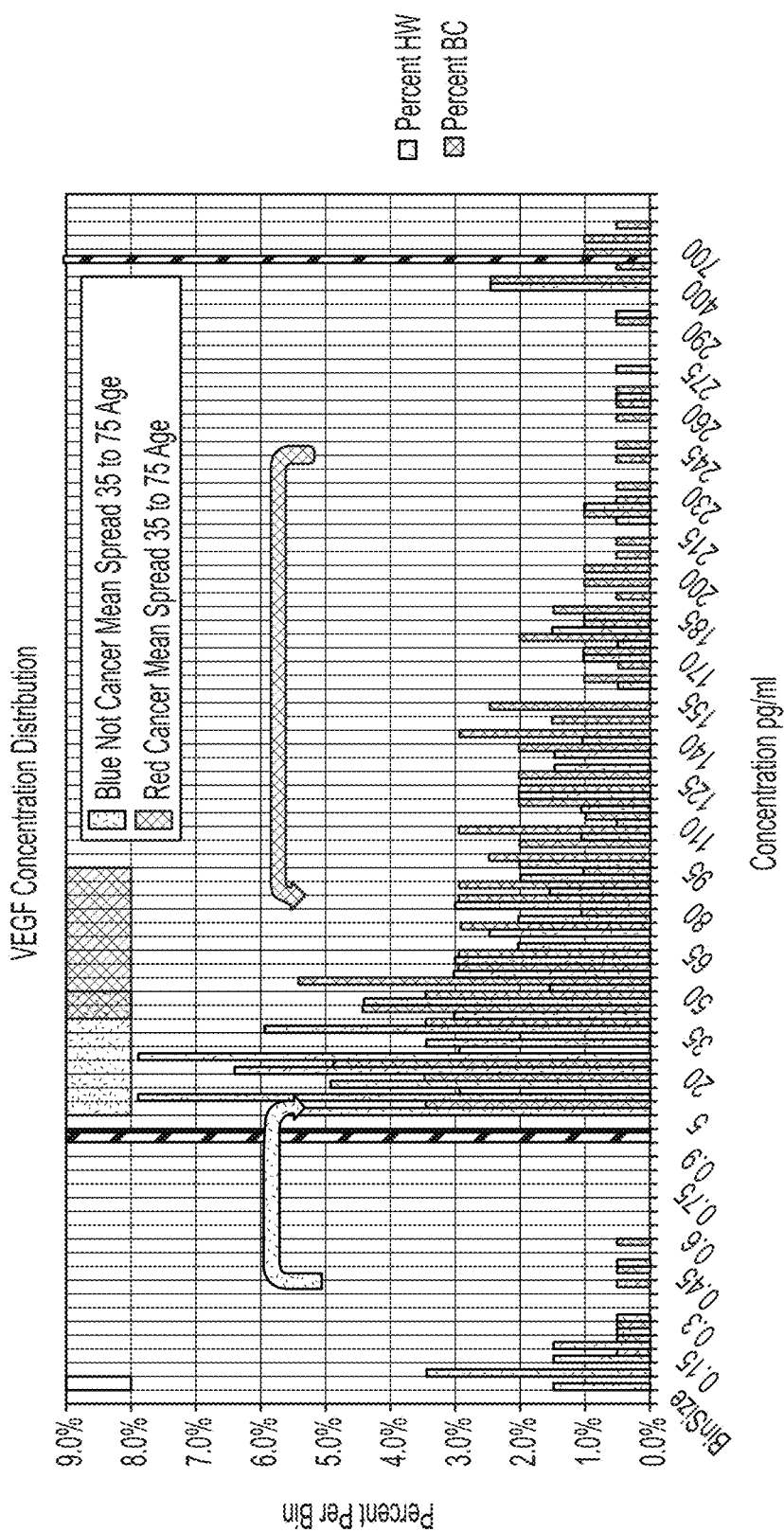
FIG. 3 shows population distribution for biomarker VEGF for 400 women diagnosed with and without breast cancer

Population distribution local bias can be managed as follows. The Training Set should by design have an equal 50% to 50% split of not-disease to disease samples, or the model will be biased. If the disease representation in the population is far from equal, this will yield areas in the grid where disease samples are far over represented than reality, causing this local population distribution bias. Breast cancer is represented in only 0.5% of the population. This problem can be mitigated by folding areas that are at very low concentrations and high fractions of not-breast cancer samples, into areas near the not-disease mean value, thus improving the distribution in this area for biomarkers that up regulate to the disease state. FIG. 3 shows the raw concentration values for these 400 women and the complex and non-linear nature of the actions of these proteins in the transition to breast cancer. In FIG. 3, the blue and red arrows show the directions of this folding. This action also has the effect of damping extraneous information in these very low level samples, and again on the higher breast cancer dominant side of the plot, discussed above. As FIG. 3 shows, the population distribution of the raw concentration of VEGF in women with and without breast cancer, this behavior is common to all five biomarkers including the tumor marker PSA. This is indicative of the highly complex and non-linear behavior of the immune system. The red bars across the top are the ranges of mean values for not-breast cancer and breast cancer as the age of the sample varies. In general, the mean value increased with age (not always). FIG. 3 has the extreme low concentration levels folded into the area just above the now fixed mean value for not-breast cancer, and they now overlap concentration values just around and above the not-breast cancer mean. The opposite is done for the breast cancer dominant side of the plot in FIG. 3.

The Spatial Density Local bias is an artifact of the complex non-linear up regulation of the proteins and the Spatial Proximity Correlation method. Isolated sample points in the middle sections between the clumping at very high and low concentrations will tend to force large sections of the grid to be called with the isolated point's designation, breast cancer or not-breast cancer. This is also corrected when the conversion to Proximity Score is done as the whole complex of raw data is compressed.

Finally, the clustering effect noted above must be retained. Thus, this conversion shifting cannot be random and must be done with contiguous mathematical operations that can be repeated on the training set and on unknown samples. In situations where the not-disease to disease transition is accompanied by full or even partial age adjusted down regulation, these same principles apply.

The Spatial Proximity Correlation method is based upon a topology rendering of not-disease and disease areas. This could yield unstable outputs when unknown sample points sit on topology areas that are deep cone or valley shapes. These points are identified in this method by a stability test. Then, if the data point is found to be unstable, it is either corrected or confirmed by a secondary model, termed incongruent that is phenomenologically different. Usually within 100 unknown samples, three to four are found to be unstable and one or two will corrected and the others confirmed.

Measurement Methods

In measurement science there are strategies for taking measurements in the presence of significant noise that will allow reduction or effective elimination of the noise by multiple measurements of the signal and noise. These methods will measure, to any degree of accuracy required, a desired signal by mathematically taking advantage of the following facts: 1) there is a signal to be measured and it can be sampled multiple times; 2) if the signal varies in time the time-wise variability must be known; and 3) the measurement schema must be correlated to this variability. If 1, 2 and 3 above are satisfied, the noise (or extraneous information) will be separated into the two components: 1) measurement correlated noise; and 2) measurement uncorrelated noise. The measurement correlated noise is called either the null signal or offset (in electronics sometimes the DC offset). The uncorrelated noise is, on average, 90° out of phase with the correlated measurement schema. This noise can be reduced by sampling the signal and offset multiple times. The noise is reduced by the square root of the number of samples. The null or offset can be determined in the same way by turning the signal off (aiming the antenna away from the signal source). In biology or Proteomics, the conventional wisdom is that the "truth" in accurately predicting a disease or non-disease state is in the raw concentration values measured and the practitioners come from a biology or clinical chemistry background. The inventive method diverts completely away from the notion that "truth" is in these raw concentration values, but is in a deeper interpretation of what the concentration values mean (see below). Thus, no one heretofore has applied certain of these measurement science techniques to biological state separation because the inventive methods necessarily eliminate certain biological information that heretofore were understood to be necessary.

There are two cases for these techniques. Both these techniques rely on the notion that the uncorrelated noise is on average 90° out of phase with the signal, and all measurements consist of three and only three components: 1) the signal; 2) the DC offset or null offset in phase with the signal; and 3) noise (or extraneous information), in general 90° out of phase with the signal and null or offset. The signal is the desired result, the null or offset is a portion of the "noise" that does not vary in time with the measurement sampling schema, and the noise is random or semi-random variation due to actions extraneous to the desired information.

The first case is when the sample rate is far lower than the noise spectrum. In this case, a single sample can be measured repeatedly, and each measurement will reduce the noise component by the square root of the number of measurements taken. If the signal is on an electromagnetic carrier, the wavelength must be known, and the receiver must be able to synchronize or correlate with it (e.g. phase locked loop). 900 measurements will reduce the noise by a factor of 30. One simply needs to redo this with the signal turned off to subtract offset and derive the final result, an accurate signal, for each sample.

The second case is where the measurement sample rate is far faster than the variability rate of the noise (or extraneous information) on a single sample. In this case, the noise for one sample is fixed within a practical measurement time rate. And thus no information, and noise reduction can be extracted from one single sample by multiple measurements over time. This is the situation faced in Proteomics measurements for a single sample where the goal is disease state detection. Multiple measurement samples of the same patient over several days will not yield changes that can be used to average out extraneous information in that sample. The noise is static.

A common usage of this noise reduction method is where multi-parameter measurements are taken on earth terrain and the goal is to indentify targets from not-targets or identify objects as "Specific Object" and "Not-Specific Object." In a possible case, the measurements may be infrared, audible, visual sighting (by machine), and two bands of radar. The individual measurement are likely "static" and thus measurements are made across many terrain situations and possible target and not targets. Ultimately, the resultant correct answer is based upon target, not-target averaging and noise suppression math schemes.

The variances found in Proteomics are not random noise, but are based upon some condition or drug cause. However, they are numerous and ubiquitous and randomly scattered across the population sample of interest. Further, there is mostly no knowledge about their occurrence and/or effect on an individual patient, so they can be considered uncorrelated to the measurement schema. Thus, they can rightfully be treated as random noise. Table 1 (above) shows a very limited list of these conditions or drugs that affect the biomarkers used in this breast cancer example.

In order to use these science concepts, the null or offset would be considered the mean value of the not-disease samples, and the signal would be the difference between the Disease mean value and the null value for each measurement and for each biomarker. All measurements that differ from the mean values are considered extraneous information or noise. In this case, one need not determine the actual value of a particular sample signal (mean cancer minus mean not-cancer), one measures it over many samples of both types. The measurement of an unknown sample is then used to determine whether it is within the group with mean signal for cancer or is in the group with just null, not-cancer. One does this reduction with mathematical manipulations that reduce the extraneous information (noise). This can be done with a correlation method where the anchor points are the mean population value for each biomarker for cancer and not-cancer. The rules for the mathematical manipulations are simple, anything that improves the correlation is viable as long as both the training set and blind samples are treated the same. The analysis may be adjusted by a person skilled in the art based on the explanation and examples contained in this disclosure. Methods that are suitable for these biological measurements will be discussed below.

Within a large sampling of raw concentration values for any one biomarker with known not-disease and disease states, there are two useful pieces of information and the not-useful Proteomics Variance. The useful information is the mean value for not-disease and the mean value for disease. Next, within one sample of raw concentration for any one biomarker there is only one piece of useful information, the ranking or position of the concentration value with respect to the two means and the derived midpoint between the means, and again there is the not-useful Proteomic Variance. The task is to suppress the Proteomic Variance within the known group and then apply this to unknown samples.

The measurement strategy can be applied to this situation by sampling a large cohort of samples with known disease and not-disease state condition. In this case, the strategy is to determine the mean value of each measurement parameter by averaging the many measurements. 100 patient samples reduce the mean value uncorrelated noise "error" by a factor of 10. Then, mathematically manipulate these known groups to eliminate, as much as possible, the extraneous information that differentiates individual samples from the mean values (the noise). The mathematical methods are limited only by the goal of forcing the predictive scoring of the predictive model to agree with the known samples. The method can involve compression, expansion, inversion, reversal, folding portions of measured variables over onto itself producing a function where multiple inputs (concentration) produce the same output (Proximity Score). The reason for this are several (see below population distribution bias) and for the purpose of damping "noise." Also, look up tables or similar tools can be used for the transformation, and other mathematical schemes. The method can include some or all of these schemas. The goal of this process is to force each known group of samples into its respective correct group be it disease or not-disease, with the respective mean values as anchor points. In the end, the resultant independent variable value may not resemble the original concentration values at all. We call this new variable, used for insertion in the correlation method, the Proximity Score. It may not resemble the original concentration measurement at all, and in fact, the concentration values may not be uniquely recoverable from the Proximity Score because the best predictive power fit may result in Proximity Score values folding back over the concentration values (one Proximity Score value may revert to many concentration values for best "fit").

Replicating this exact method can then be used to force unknown or blind samples into either group, disease or not-disease based upon the notion that the forcing group behavior characteristics on individual samples will positively force the predictive power of the model on the blind samples. The first level proof for the model is its internal predictive power to force correctly the known group or training set samples. The final proof will be the resulting models ability to correctly place unknown (blind) samples into the correct groups, the validation group. This final proof will also require that the model or training set size be sufficiently large to accurately represent the statistics of the parameters measured within the general population of interest outside of the training set model. The methods can be described as mathematically forcing group behavior of the known sample set under the assumption that this exact same forcing will properly place unknown samples.

As discussed above, FIGS. 1 and 2 show an example of two biomarkers VEGF and IL 6 plotted in bi-planes. FIG. 1 shows the biomarkers plotted as raw concentration values. The red data points are the breast cancer samples and the blue are the not-breast cancer samples. The red and blue arrows show the spread over concentration of the age adjusted mean values of the breast cancer and not-breast cancer samples. There is natural tendency to think of this plot as truth for the cancer vs. not-cancer state. However, the deeper truth is that this plot has overlaid on it a tremendous amount of information that cannot be retrieved for causation or understood or rationalized to the two conditions under investigation, that is, breast cancer or not-breast cancer. There are imbedded into the scatter of data an unknown number of non-malignant conditions that affect both the cancer (red) and not-cancer (blue) data points. These conditions scatter the data and reduce the accuracy of the correlation. Also, the age drift in mean value tends to obscure again the transition from not-cancer to cancer.

Table 1 above shows some of the various conditions that can affect to varying degrees these protein concentrations in serum, that are useful for diagnosing breast cancer. These conditions are embedded in the general population as shown in the table for trace amounts to as high as 10%. There are many more. The table should be considered just a limited survey, compiled by surveying scientific literature. One must be concerned that most of these conditions or drugs that cause this Proteomic Variance are in fact not known. The scientific literature only focuses on these conditions or drugs and these biomarkers that have scientific interest.

The presence of these conditions is in general unknown in patients seeking screening for a specific disease, (e.g., breast cancer), and the question asked is in which group does the unknown patient fit in, the not-breast cancer or the breast cancer group. The unknown variance must be dampened as it is done in Proteomic Variance, "noise" suppression in the measurement science, in order to answer this question. Note that both the breast cancer positive patients and the not-breast cancer concentration measurements are contaminated with this extraneous information. Furthermore, the notion of the "proper" value for these biomarkers for a "healthy" individual as well as an individual with the disease is meaningless. The only way to make sense of this scattering of the concentration data is to dramatically suppress the noise for both of the cohorts by anchoring on the mean values and suppressing all other information in the concentration data. The result is the Proximity Score. One could say that the notion of "proper values" for these concentrations for a "healthy" or diseased individual is meaningless. The extraneous information, Proteomics variance "noise", is what contributes to the scatter in FIG. 1. This noise suppression is what produces the cleaner plot in FIG. 2.

The first step is to reconcile what can be known about the FIG. 1 plot for breast cancer. There are limited pieces of information in the plot that relate to the question: is the unknown patient likely to have a not-breast cancer disease state or a breast cancer disease state. The information in the plot are the mean values of the two biomarkers for both not-breast cancer and breast cancer. Beyond these mean values, we can rank each individual sample by its relationship to the means. There are only four ranks or zones: 1) the individual sample is less than the mean value for not-breast cancer; 2) the individual sample is greater that this mean value for not-breast cancer but less than the derived midpoint mean value between the breast cancer/not-breast cancer means; 3) the individual sample is above this midpoint of the means and below the mean value for cancer; and 4) the individual sample is above the mean value for breast cancer. Furthermore, the mean values noted for each state and each biomarker drift with age. Thus, the relationship between age and the mean values must be known. Each of the rankings noted above must be limited for any one patient to the mean for that patient's age. Any information beyond this for individual samples is not useful and can be considered Proteomic Variance (noise). These five pieces of information (age and relationships of the means and midpoint) are the deeper interpretation of the raw concentration measurements. As noted, this information, when evaluated according to the present invention, surprisingly reflects the truth with respect to the question at hand, is the patient not-disease or disease. And thereby provides a method of indicating the probability of a disease state existing in a patient under examination.

Finally, the mean values and ranking are transferred from the raw concentration such that the mean values are normalized and the noted ranks are plotted in specific zones. This transformation from raw concentration, anchored by age adjusted means and age adjusted rankings with respect to the means, produces a new independent variable for the Spatial Proximity plot and correlation method. This variable is called a Proximity Score.

FIG. 2, as discussed above, shows the resultant bi-plane plot after conditioning the raw concentration into Proximity Score. Also the age drift is normalized such that all age groups are positioned at a fixed or set point for each biomarker. Thus, if an unknown patient sample happens to have a concentration value at the not-cancer mean value for its age, then its Proximity Score will be fixed at the set value, and all patient samples at all ages who are at the mean value will get that same value in Proximity Score.

In this example, the set values are arbitrary 4 for not-cancer mean and 16 for cancer mean. Other values could be used, such as a broader range, for example. Also, note that in this example the raw outlying concentration values achieve best fit to the known patient diagnosis of the training set by folding these concentrations into the space between the now newly set fixed mean values for pseudo-concentration. This achieves the damping of noise needed and the transformation is designed to retain the clumping behavior that the correlation method is based upon, the Spatial Proximity Correlation.

Each individual raw concentration value is then placed within one of 4 "ranks" based upon its position with respect to the means at its age in the concentration space. Once converted to Proximity Score, age is removed from the new independent variable for the correlation (see below for details). This is not the only equation set for this task and best fit of the training set to the real diagnosis. The design of this transformation is based upon the fundamental characteristics of the raw data to be fitted and the underlying characteristics of the Spatial Proximity method. A workable solution can be found by iterative trials.

Use of these five biomarkers described in this application, IL 6, IL 8, VEGF, TNFα, and PSA for breast cancer, and yields the predictive power noted in Table 1 above for various correlation methods. While these particular markers are sufficiently orthogonal and provide sufficient information to separate disease states, it is contemplated by the inventors that other sets of biomarkers can be utilized and different numbers of biomarkers in such sets may vary.

These biomarkers produce predictive power with standard logistic regression methods typical of any group of five such markers. This level of predictive power is also typical of the various Receiver Operator Characteristic (ROC) curve methods for maximizing the aggregate area under the ROC curve (i.e., about 80%). The conversion to logarithm scales is also typical as the raw concentration ranges often exceed 5 orders of magnitude. Also, using the logarithm of concentration with the Support Vector Machine and Spatial Proximity correlation method yields better predicative power (i.e., 84 to 85%). This is likely due to the spatial separation effects of these biomarkers. The conversion to Proximity Score (reduction in extraneous information) also yields even more significant improvement in predictive power (i.e., 87 to 90%). However, the best predictive power results with the combination of all three, these functionally orthogonal biomarkers, Spatial Proximity correlation, and the conversion to Proximity Score (i.e., 96%). Finally, correcting the Spatial Proximity method for topology instability improves this predictive power to greater than 96%.

The analytical model comprising an embodiment of the methods of the present invention generally follows the following steps:

1) Collect a large group of known not-disease and disease patient samples. They should not be screened for any other unrelated conditions (non-malignant for cancer) but collected such that they look statistically like the general population.

2) Measure the biomarker parameter concentrations.

3) Compute the mean values of these biomarkers for the not-disease and disease group (see additional considerations below under age drift of the means).

4) Mathematically manipulate the raw concentrations to force them into groupings that mimic the mean values. This may involve compression, expansion, inversion, reversal, look up tables for transformation, and other mathematical operations. The method may contain some or all of these schemas. The resulting numerical value may not resemble the original concentration values at all, and one may not be able to work back from the resulting value to concentration as the transformation curve may fold back on itself. This new independent variable for the correlation is called Proximity Score. In fact, the resulting distribution is likely to be piled up near the two mean values with the mean value anchor points retained.

5) The manipulation also must force the unknown sample into rankings based upon that sample's relationship to the aforementioned mean values. Herein, we define zones that are respectively: 1) below the unknown sample's mean value at its age for not-disease; 2) above the not-disease mean value at its age but below the derived midpoint between the not-disease mean and disease mean at its age; 3) above the derived midpoint between the not-disease mean and disease mean but below the disease mean value at its age; and 4) above the unknown sample's mean value at its age for disease. These zones can be compressed into spaces near and/or on the respective means to dampen variances caused by the unrelated contaminating conditions or drugs.

The aforementioned mean values must take into account the age of each patient who contributes a biological sample. The zone positioning of each sample must be related to the corresponding patient's age and the mean values of the disease and not-disease means at that patient's age.

Possible Equations Used for Concentration to Proximity Score Conversion

The Ratio Log Linear Equation Used for OTraces Breast and prostate Cancer Determination is:

One equation for conversion of concentration to Proximity Score discussed in the referred application is:

$$PS_h = K^* \text{logarithm}_{10}((C_i/C_{(h)}) - (C_c/C_h))^2 + \text{Offset}$$

$$PS_c = K^* \text{logarithm}_{10}((C_i/C_c) - (C_h/C_c))^2 + \text{Offset} \quad \text{Equation 2}$$

Where:
$PS_h$ +Proximity Score for not-cancer
$PS_c$ =Proximity Score for cancer
K=gain factor to set arbitrary range.
$C_i$ =measured concentration of the actual patient's analyte
$C_h$ =patient age adjusted mean concentration of non-disease patients' analyte
$C_c$ =patient age adjusted mean concentration of disease patients' analyte.
Offset=Ordinate offset to set numerical range (arbitrary)

Figure 19:
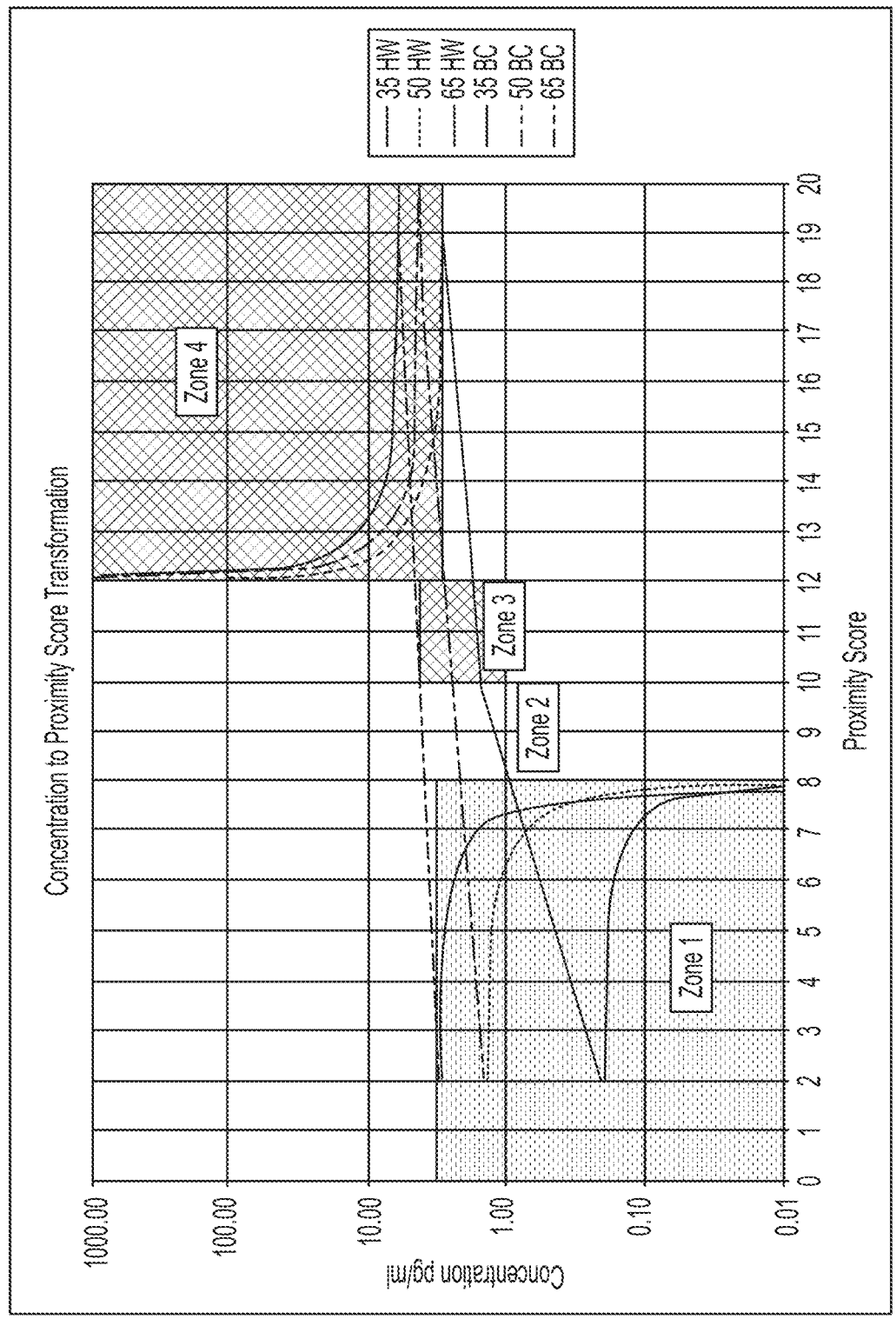
FIG. 19 shows the concentration to Proximity Score conversion for one equation set.

This embodiment, FIG. 19, shows Zone 1 fold on to Zone 2 and Zone 4 folded back on Zone 3 (see section on Population Distribution Bias). In the case of Cancer Versus not Cancer the cancer cohort is over represented in the training set by a large margin. The folding improves the distribution bias the zones dominated by not cancer. This embodiment is shown in FIG.

Figure 20:
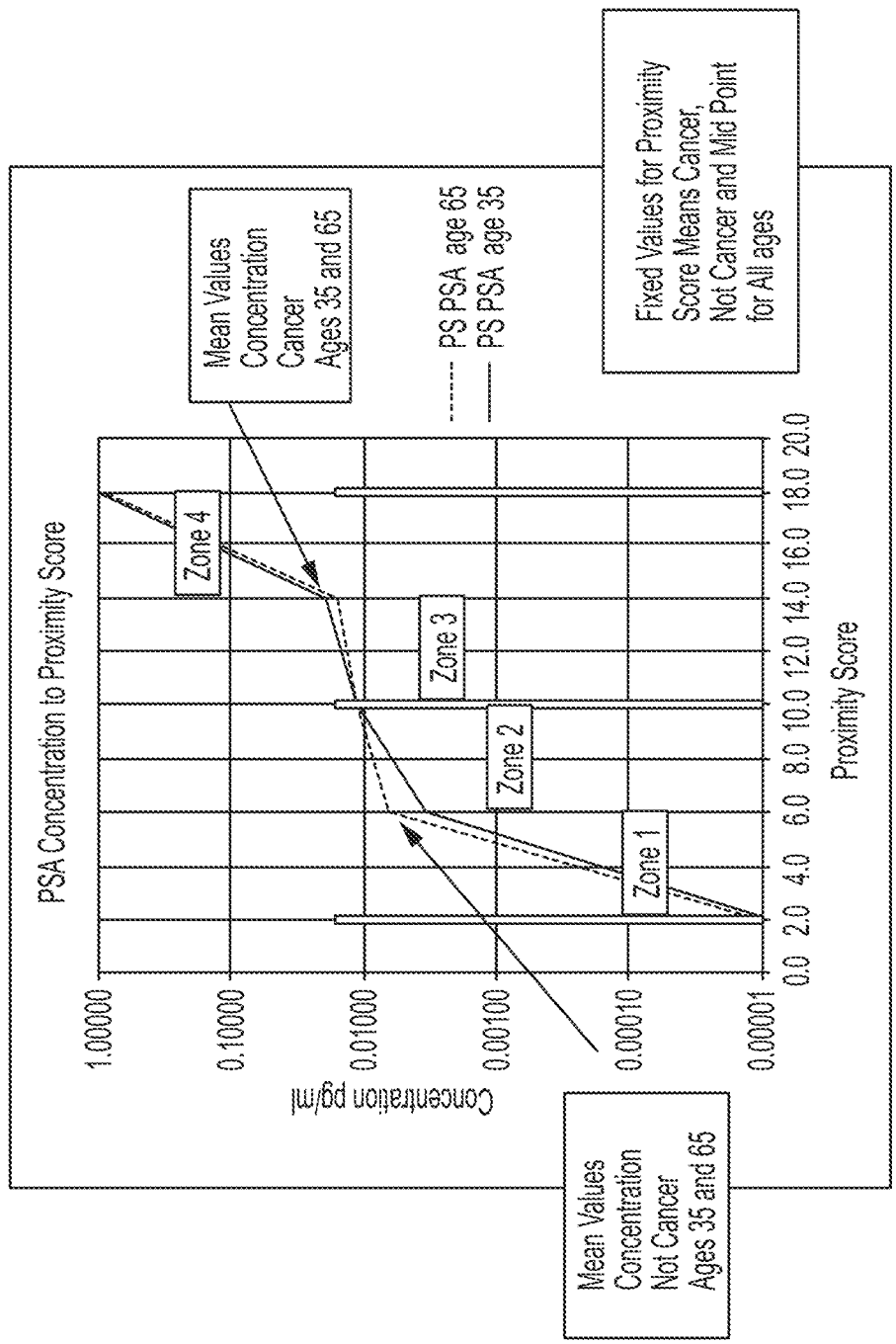
FIG. 20 shows the concentration to Proximity Score conversion for another equation set.
Figure 21:
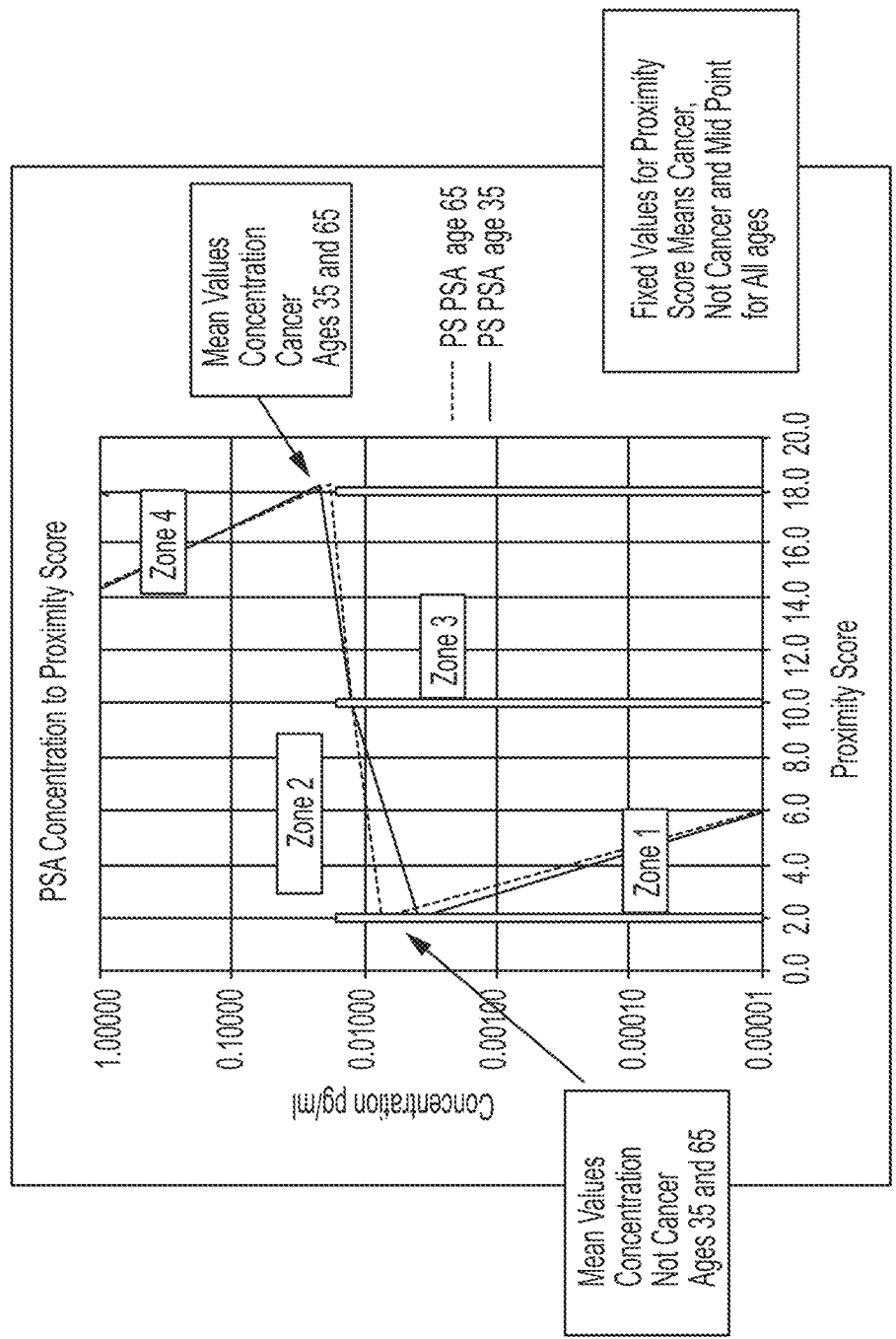
FIG. 21 shows the concentration to Proximity Score conversion for another equation set with zones folded over on top of another.

8) Another Embodiment uses straight log concentration to linear conversions.
where:
PS=M(log(Ci)+B
PS=Proximity Score the concentration
$C_i$ =measured concentration of the actual patient's analyte
M=conversion slope
B=Offset This embodiment is shown in FIGS. 20 and 21. FIG. 20 shows the order of the four zones in maintained order on the Proximity Score axis. FIG. 21 shows the zones 1 and 2 overlapped as are zone 3 and 4 (see population distribution bias below). Folding Zone 1 fold on to Zone 2 and Zone 4 folded back on Zone 3 is useful where the population distribution of the two states "A" and Not "A" are somewhat equal in population distribution.

7) This new variable called Proximity Score is applied to the correlation method of choice (see sections herein for discussions of this). 8) Using the same schema as developed to maximize predictive power within the training set model, determine whether an unknown samples "fits" either in the not-disease or disease group.

The age related mean value function is the anchor point for the transition from raw concentration and the new Proximity Score used in the correlation on the Spatial Proximity Grid. This function is determined from a large population of known disease and not-disease samples, and the population can include the training set but can also include a larger group. The not-disease and disease populations are defined as noted below. It is a function that relates mean value of not-disease and disease to age as it drifts. It is used to place the mean values to fixed positions on the Proximity Score axis where raw concentration is converted to Proximity Score. It will usually result in a family of equations that perform the transformation—one for each year of age. This function allows normalization of age drift.

Figure 4:
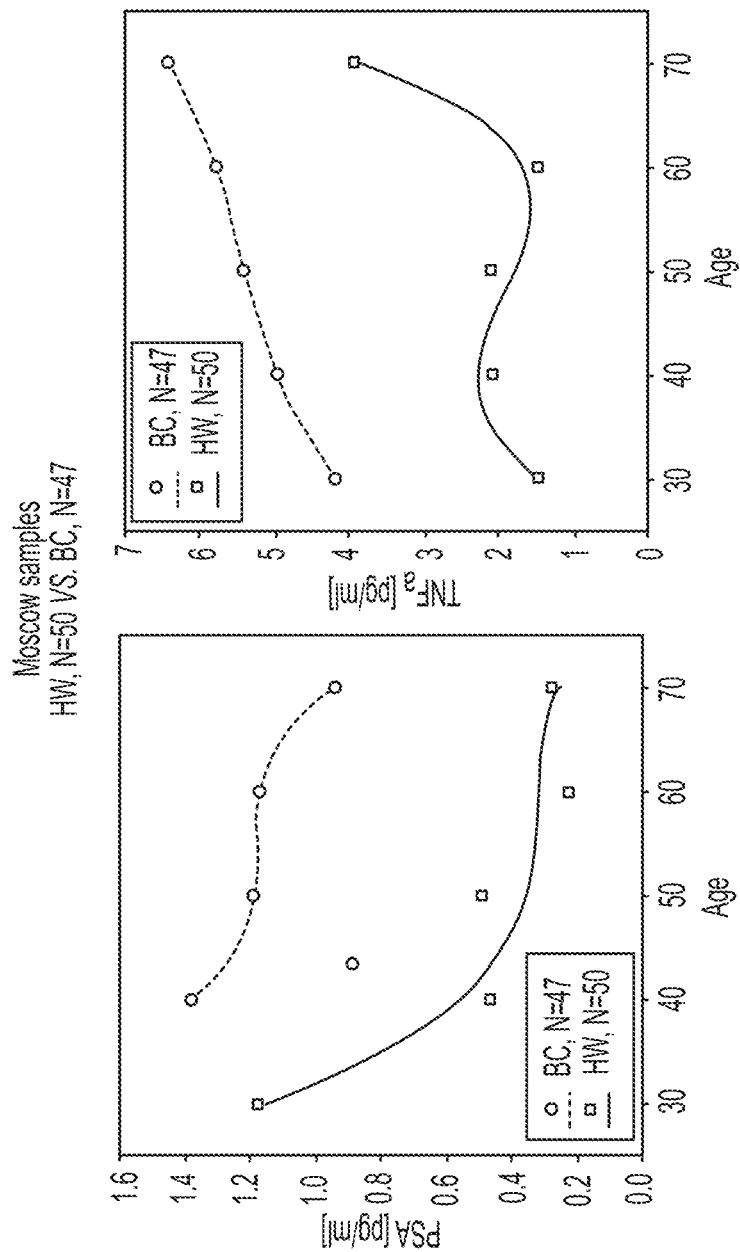
FIG. 4 shows the age distribution of the biomarkers PSA and TNFα mean concentration values.

FIG. 4 shows such functions for breast cancer and not-breast cancer from market clearance trials conducted at the Gertsen Institute Moscow for TNFα and Kallikrein 3 (PSA). Note that this plot can give very good indications of the biomarker that will yield predictive power when coupled with other biomarkers in the manner described in this application. The degree of separation, across all ages indicates, from the measurement science perspective, that there is a strong "signal" that will differentiate from the not signal condition, disease and not-disease will differentiate. In most cases, this will give a better indication of predictive power than a single ROC curve.

Use of Functionally Orthogonal Biomarkers and the Spatial Proximity Correlation Methods The method uses the Spatial Proximity search (neighborhood search) for correlation. This method places each independent variable on a spatial axis, and each biomarker used has its own axis. Five biomarkers are placed in a 5 dimensional space. Each biomarker is transformed by the meta-variable method discussed in the patent PCT/US2014/000041 and above. This method forces the normalization of age related drift in concentration actions and immune system non-linearity. The test panel discussed here is for breast cancer and it uses an inflammatory marker, Interleukin 6; tumor anti-angiogenesis or cell apoptosis marker, Tumor Necrosis Factor alpha; and tumor vascularization markers, Vascular endothelial growth factor (VEGF); and an angiogenesis marker, Interleukin 8; as well as a known tumor tissue marker, kallikrein-3 (or PSA). These markers are highly complementary in the proximity method for correlation as their functions do not overlap significantly. Thus, when plotted orthogonally, they enhance separation as each added axis pulls the biomarker data points apart, for not-cancer and cancer as shown in the Figures. Other standard correlation methods such as regression analysis or ROC curve area maximization methods cannot retain this orthogonal separation as the mathematics analysis looks for individual marker trends (linear regression-linear and logistic-logarithmic). Any spatial information is lost.

Figure 5:
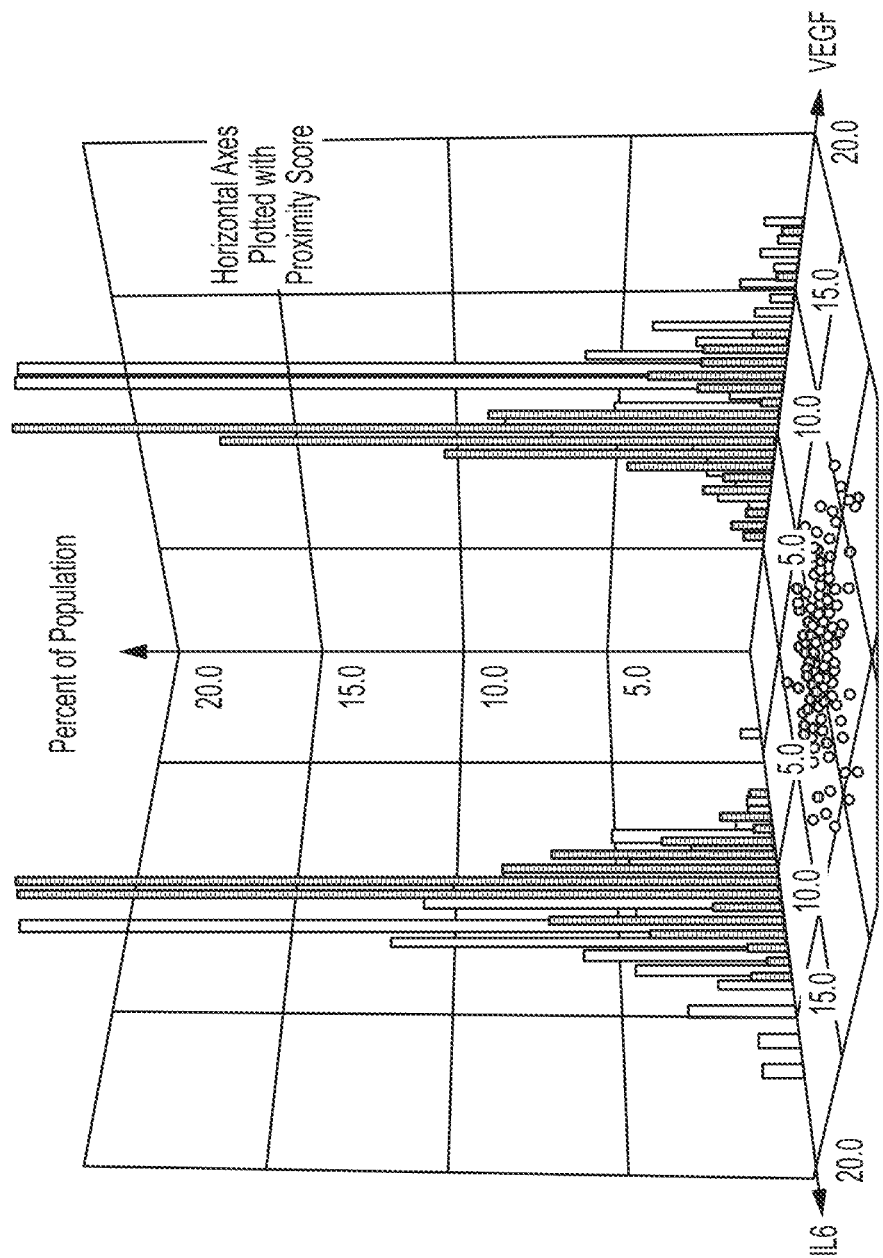
FIG. 5 shows a 3 D plot of IL 6 and VEGF Proximity Scores plotted on the horizontal axes and population distribution on the vertical axis.
Figure 6:
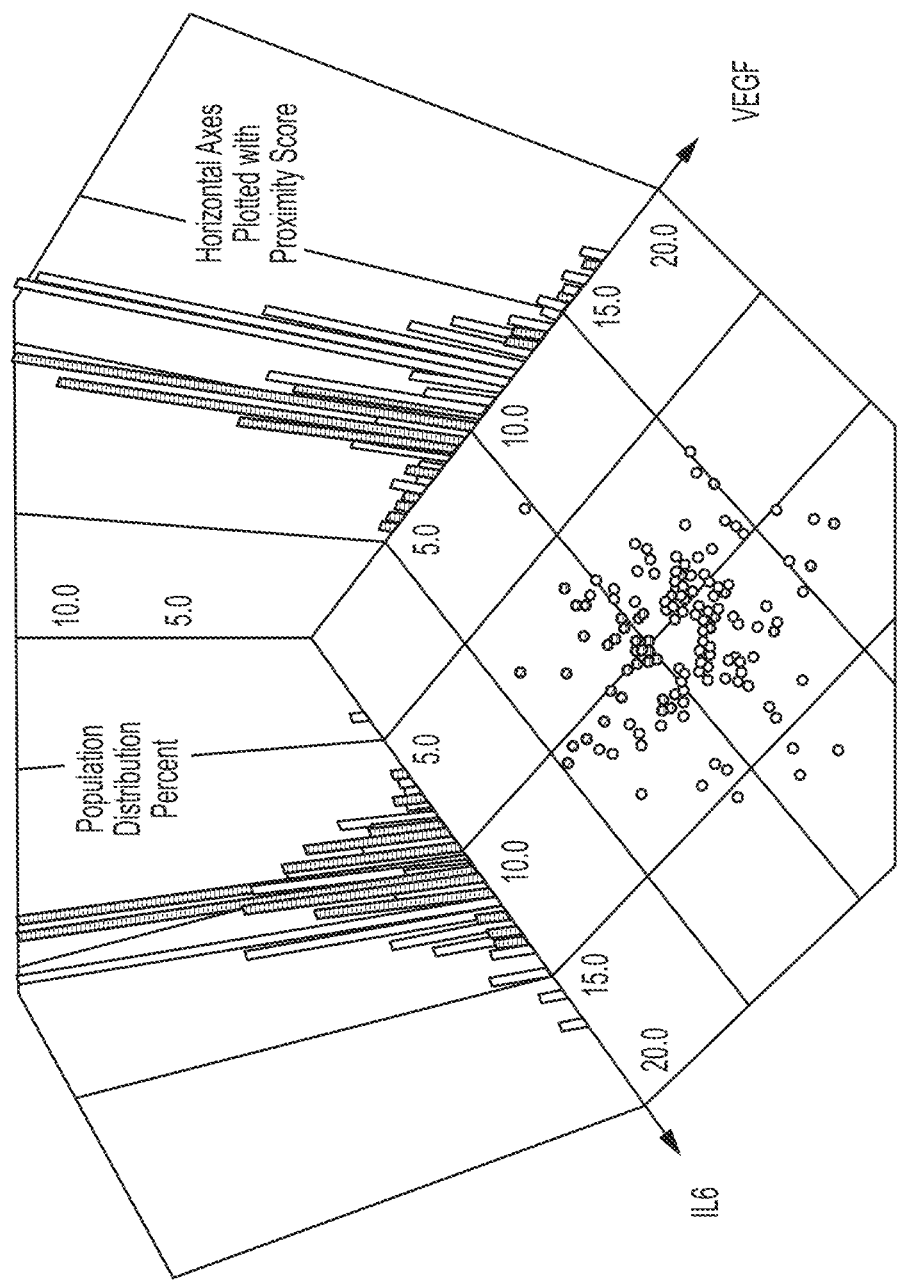
FIG. 6 is FIG. 5 with the horizontal axes rotated down showing the horizontal separation of the blue (not cancer) and red (cancer) samples.
Figure 16:
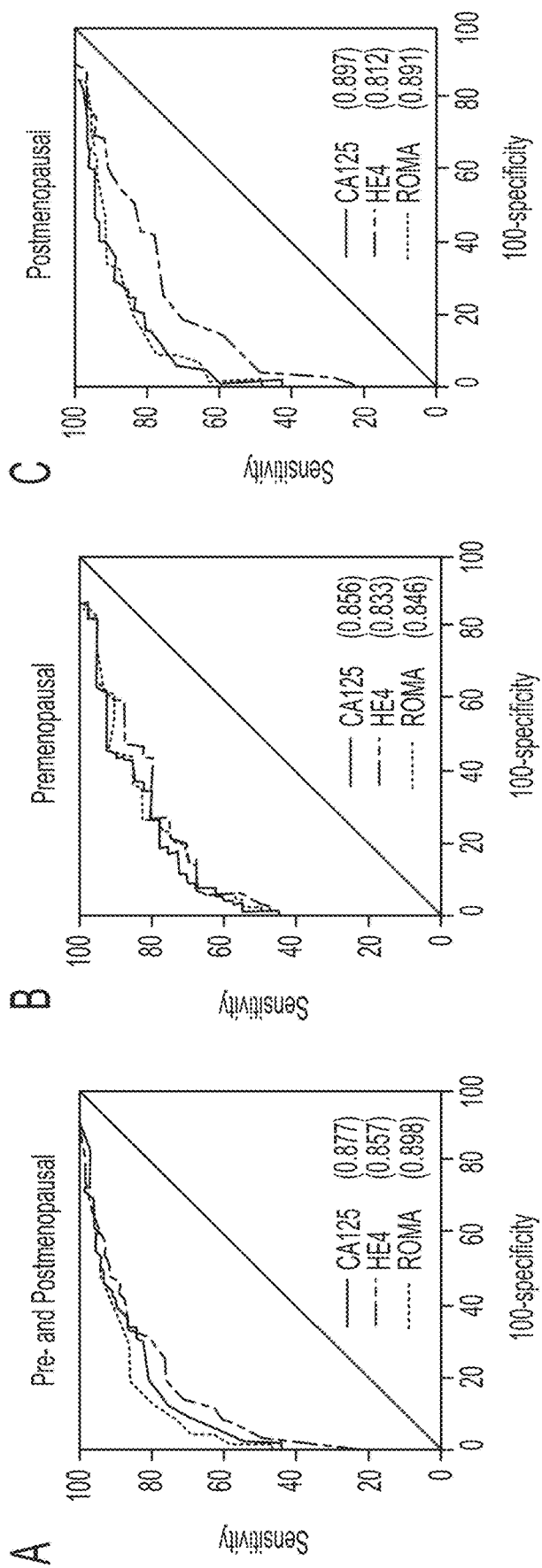
FIG. 16 shows the ROC curves for CA 125, HE 4 alone and the composite ROC curve for the ROMA test for ovarian cancer.

The phenomena noted above, orthogonality or incongruence of function, can also be seen graphically in FIGS. 5 and 6. These graphs show the concentration population distribution of the pro-inflammatory biomarker, IL 6 plotted against the vascularization biomarker VEGF on the horizontal orthogonal axes. FIG. 5 shows the 3 D plot rotated so the horizontal plane is nearly horizontal, and FIG. 6 shows this x, y plane rotated so the planar distribution of the markers can be seen on this horizontal plane. The horizontal concentration axes show this parameter plotted not in concentration units but the in the Proximity Score computed as discussed herein. The vertical axis shows population distribution as a percentage of the total. The bin size is 0.5 units of Proximity Score for each vertical bar. Note that this graphic plotting depiction will not allow side by side separation of the two population groups, not-cancer (blue) and cancer (red). Thus the bars overlay each other. When the blue population is higher than the red, the blue shows above the red and vice versa, but they do not add, the red behind the blue still shows the red high as correct on the vertical axis. Note the considerable overlap of the not-cancer on the cancer population and vice versa, as one would expect with any one biomarker. Also note that the cancer, red, are generally at higher Proximity Score levels along each axis compared to the not-cancer, blue samples, as one would expect with a single biomarker. FIG. 6 shows these same 3D axes rotated 45° down to show the horizontal axes. Note the dramatic separation of the individual markers. The pro-inflammatory markers, IL 6, that show a low response, but are red, cancer, tend to show a high level vascularization response, and vice versa. This effect would be expected by any biomarker chosen for its uncoupled functionality with respect to the other biomarkers chosen and where the biomarkers up regulate in general to the cancer. This would be expected by simple probability, both proteins up regulate in the disease transition, and those with a low response from one function will likely show a stronger response from the other. This effect is even more enhanced in breast cancer with the orthogonality of the inflammatory and vascularization functions. FIG. 16 shows the degree of up regulation of each of these proteins in breast cancer by cancer stage. Note that the pro-inflammatory marker up regulates highly first at the onset of the nascent stage 0. However, as the tumor progresses, the vascularization marker up regulates to a greater degree as the tumor grows, stage 1 through 4. Thus, low level pro-inflammatory response, late stage, is coupled with high level vascularization response. And high level pro-inflammatory response is coupled with relatively low level vascularization response in the early stage of the disease. This behavior, when plotted in a multi-dimensional correlation method, will separate, in cancer, low level vascularization response with high level pro-inflammatory response, pulling these sample points away from the origin (and vice versa for the opposite). The correlation information is in the pull by function away from the orthogonal axis for the other function, in cancer. Note that this enhancement is lost in methods such as regression or ROC curve area maximization as the coupling of the orthogonal functions is lost.

Figure 7:
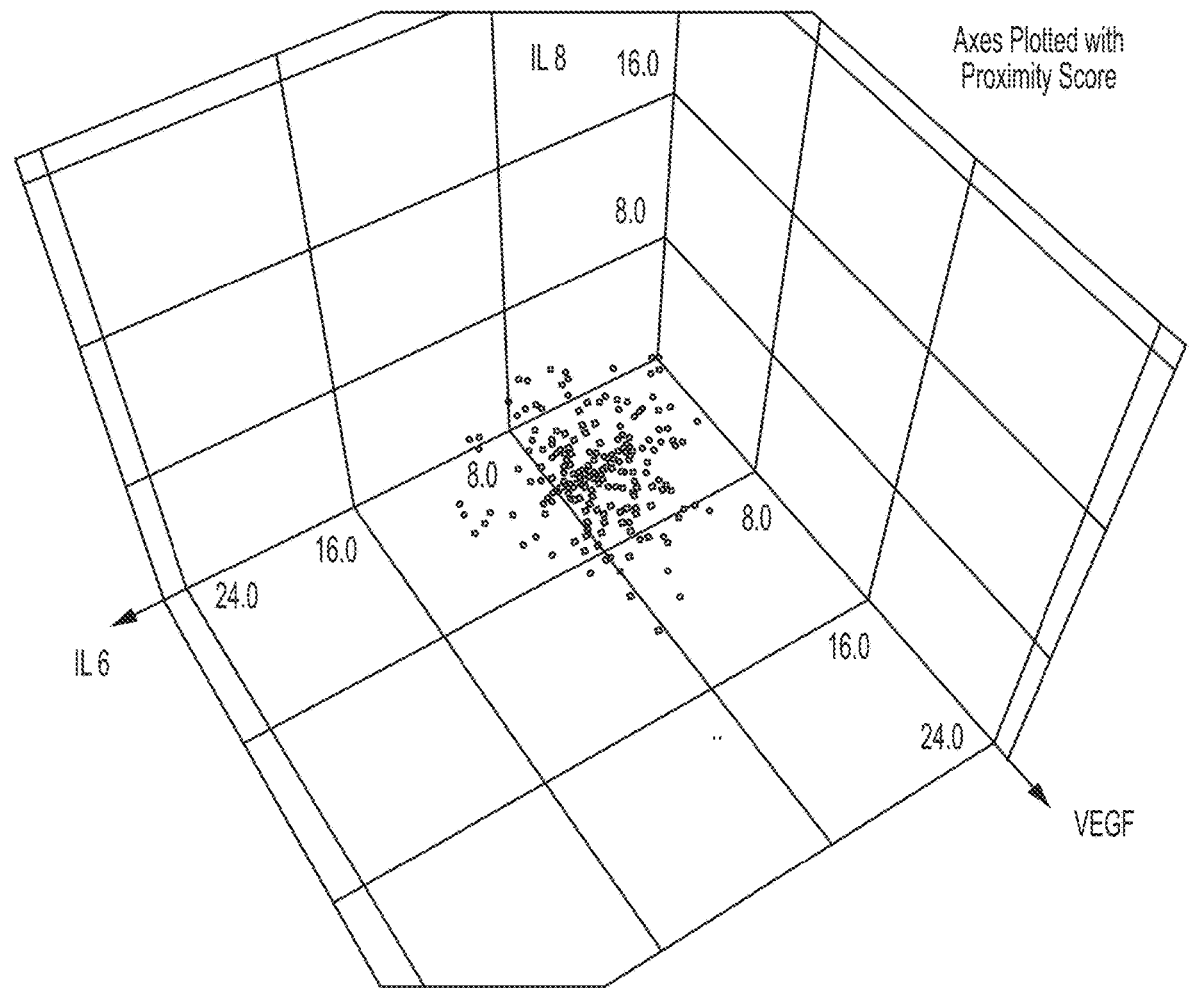
FIG. 7 is a 3 D plot showing IL 6, VEGF and IL 8 plotted.
Figure 8:
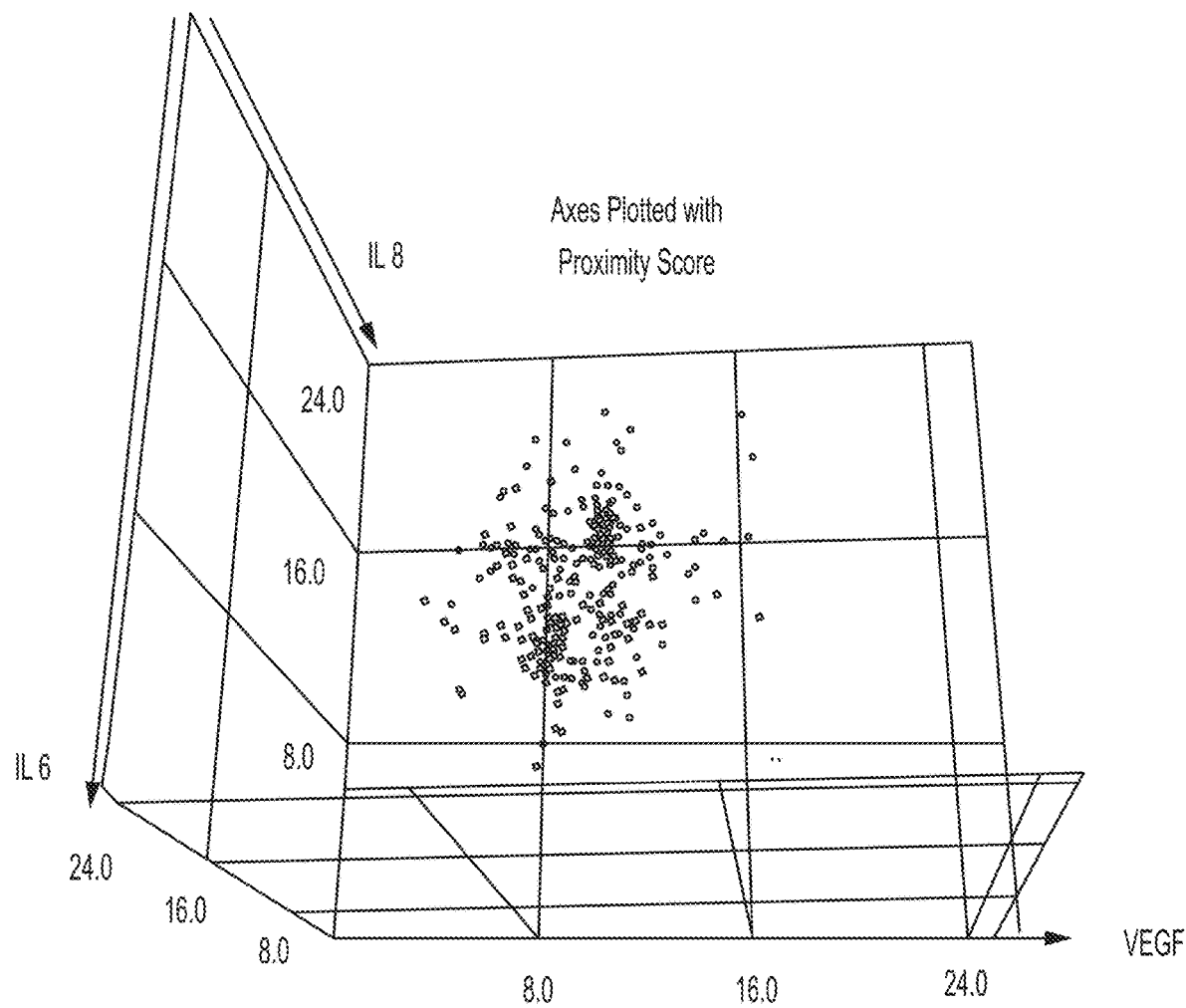
FIG. 8 shows the plot in FIG. 7 rotated around the vertical axis and tilted back.
Figure 9:
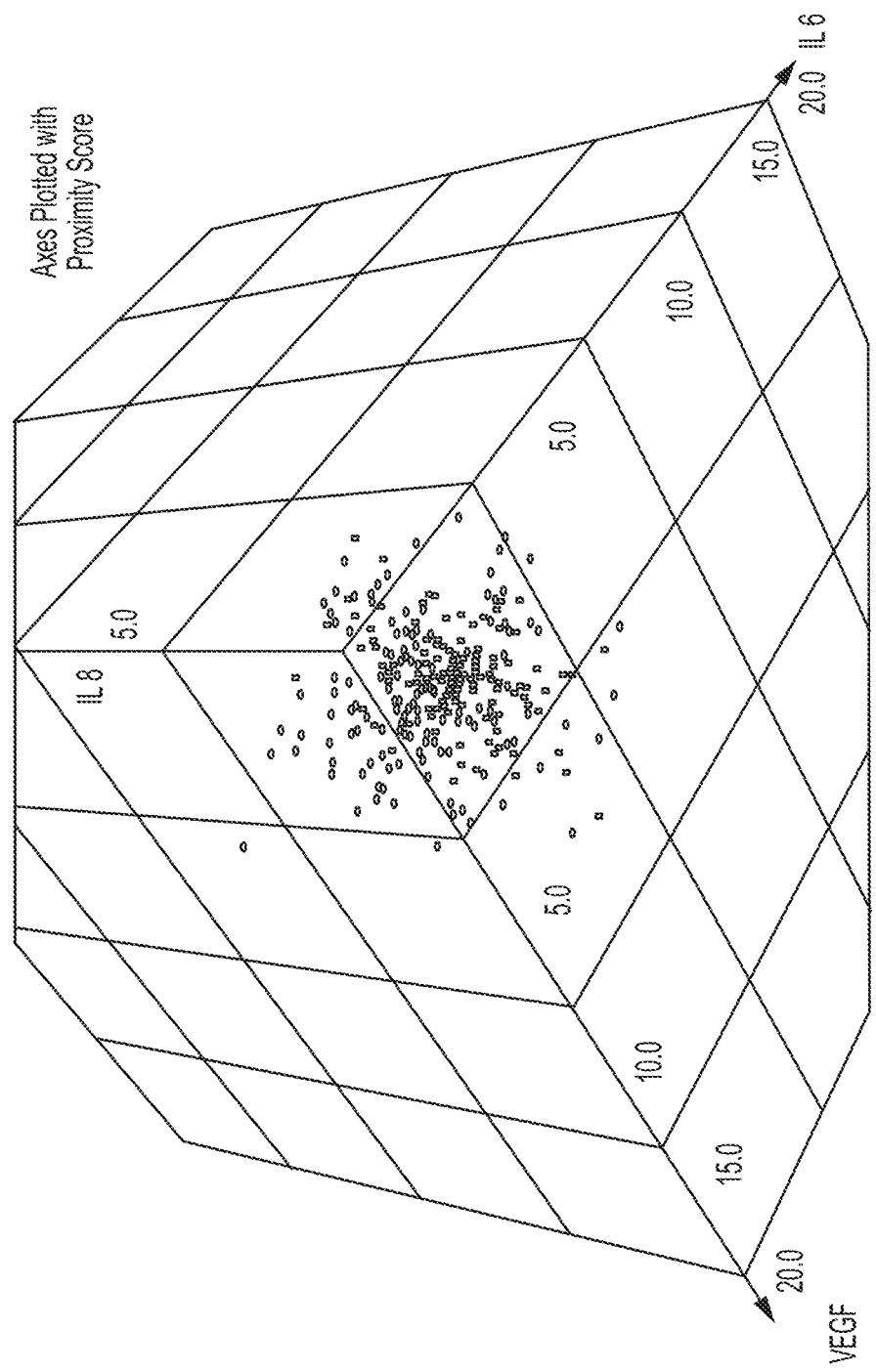
FIG. 9 shows the plot in FIG. 7 rotated around to see the back through the origin.
Figure 10:
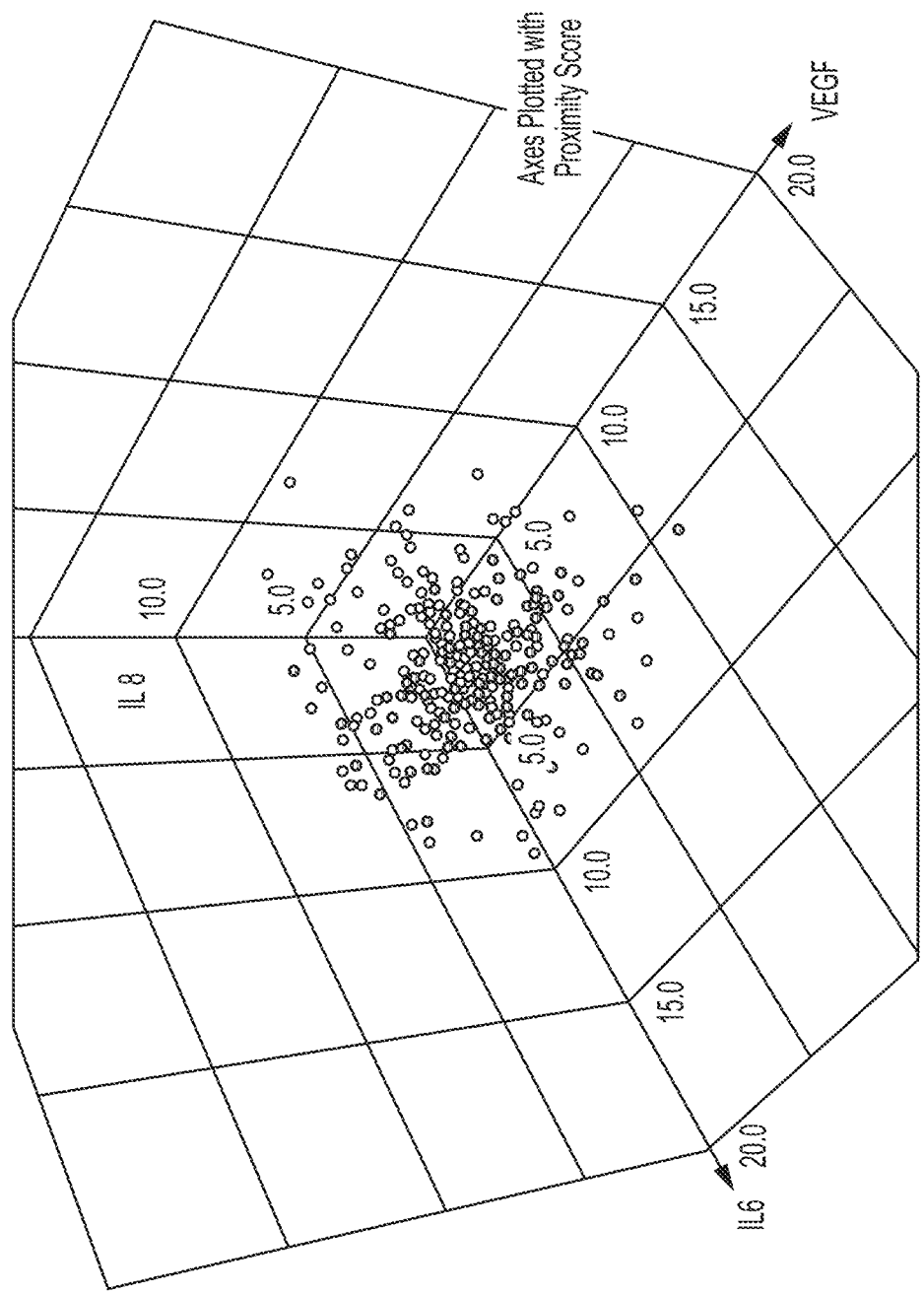
FIG. 10 shows the plot in FIG. 7 rotated upwards to show the red (cancer) samples in front.

FIGS. 7 through 10 show a third biomarker IL 8, primarily an angiogenesis function in 3D with the other two discussed above. Note that angiogenesis, IL 8, and vascularization, VEGF, are both involved in growing blood vessels but are not the same. Angiogenesis, IL 8, drives creation of blood vessels from tissues with existing circulation and vascularization, VEGF, drives production of new blood vessels in bulk tissue where there are no pre-existing ones. Tumors are known to produce both responses. Again, looking at FIG. 16, angiogenesis is strong in the early stage when the tumor is within vascularized tissue and vascularization increases as the bulk tumor grows. The plots are: FIG. 7 shows the plot looking down into the plot origin at 45° from above for all axes. FIG. 8 shows the plot rotated showing the horizontal axes ten degrees above horizontal and the vertical axis rotated about 35° to the right. The blue, not-cancer, are clearly located below the red, cancer, and closer to the origin. FIG. 9 shows the whole plot rotated around to the back side to look through the origin to the not-cancer, blue with the cancer red in back, FIG. 10 shows the plot rotated up slightly to show the red, cancer in front of the blue not-cancer. Note that this separation is greatly enhanced by not using actual concentration but the Proximity Score discussed in related applications, as outlined above (e.g., provisional application No. 61/851,867 and its progeny) and in this application. These plots clearly show how selecting biomarkers with complimentary functions, (i.e., orthogonal) yield significant improvements in separation and thus predictive power. This improvement will continue through the other two markers not shown, TNFα (anti-tumor genesis), and Kallikrein 3 (PSA) tumor marker. They can't be plotted with the first three, of course, as this would exceed 3 dimensions, and the eye cannot see this. These two markers, when plotted against one of the three noted above, will look substantially the same, showing a high degree of separation on each axis. The computerized 5 dimensional Spatial Proximity correlation method retains this orthogonality.

Figure 11:
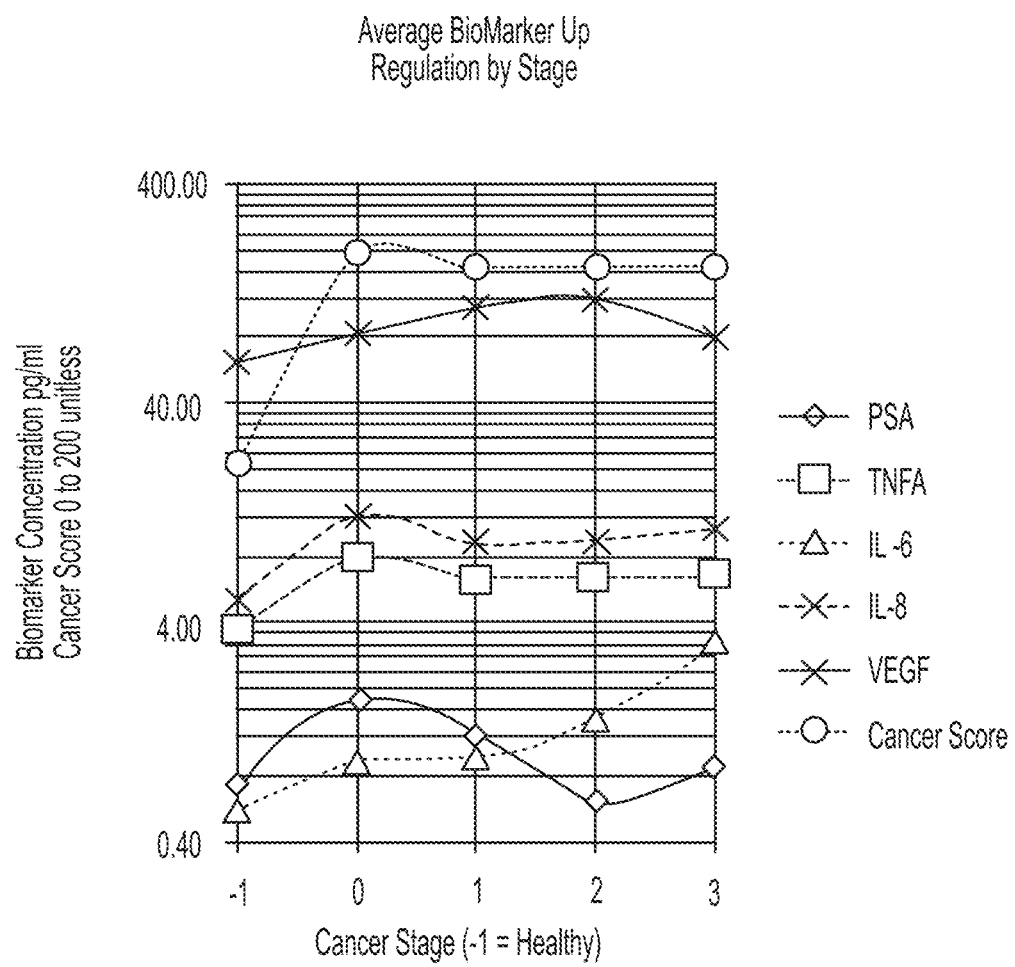
FIG. 11 shows the actions on the five breast cancer biomarkers actions as the cancer progresses from healthy to stage 3 breast cancer.

In summary, the nascent breast cancer tumor, stage 0, develops a very strong pro-inflammatory response, as shown in FIG. 11. This response by itself cannot be differentiated from infections, allergies or autoimmune disease (and others). However, this same nascent tumor will generate a strong angiogenesis response, circulatory increases in vascularized surrounding tissue. Thus, in FIGS. 7 through 10, the nascent tumor samples will move out on the pro-inflammatory axes and up the angiogenesis axis (and the tumor anti-genesis axis and tumor biomarker axis in the fourth and fifth dimensions). A late stage tumor stage 3 or 4 will tend to show a strong vascularization response (growth in bulk tumor tissue without vascularization) and a weaker anti-tumor genesis, moving out from the origin on the VEGF axis. These cannot be discriminated from trauma wounds, cardiac ischemia or pregnancy as these conditions call for vascularization. However, again, unrelated functions, tumor anti-genesis and up regulation of the tumor marker will create the differentiation.

This improvement is multiplied as the other three biomarkers are added to the 5 dimensional correlation grid. This careful selection of biomarkers for incongruent functionality improves predictive power over methods where multiple tumor markers are selected. Tumor markers for the same tumor tend to measure the same phenomena and this will not pull the biomarkers apart on these orthogonal axes and they will just rotate the group clustering by 45 degrees. Regression and other methods do not retain this orthogonal information. This improvement can only be achieved with functionally orthogonal biomarkers and the Spatial Proximity correlation method.

The measured concentration values themselves are not used in the 5 axis grid for the Spatial Proximity correlation. The Proximity Score is used. This computed value removes age related drifts in the transition from not-cancer to cancer, the age variation in the mean value of actual concentration, not-cancer and cancer are normalized. Also, actual concentration is carefully expanded and compressed to eliminate what we call local spatial and population density biases to determine the value of the Proximity Score. This number is unit less and varies over an arbitrary range of 0 to 20. These two corrections will improve predictive power by about 6%. The use of incongruent functional cytokine groups will achieve about 10% to 15% higher predictive power than using multiple tumor markers as biomarkers. The normalization of age drift and non-linear up down regulation produces a 6 to 7% improvement in predictive power over conventional proximity search methods.

Figure 12:
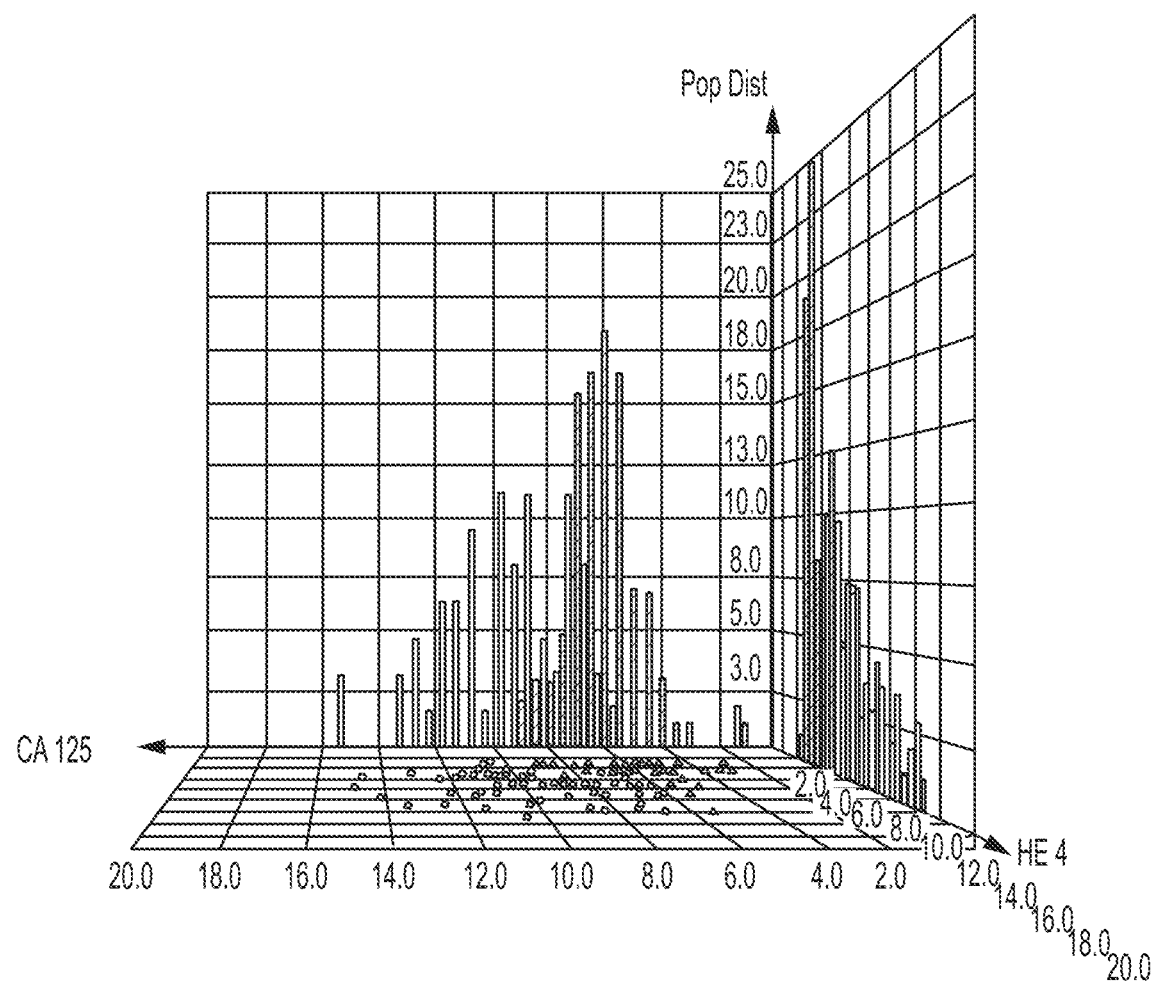
FIG. 12 is a 3 D plot of the biomarkers CA 125 and HE 4 for ovarian cancer with population distribution of the Proximity Score shown on the vertical axis.
Figure 13:
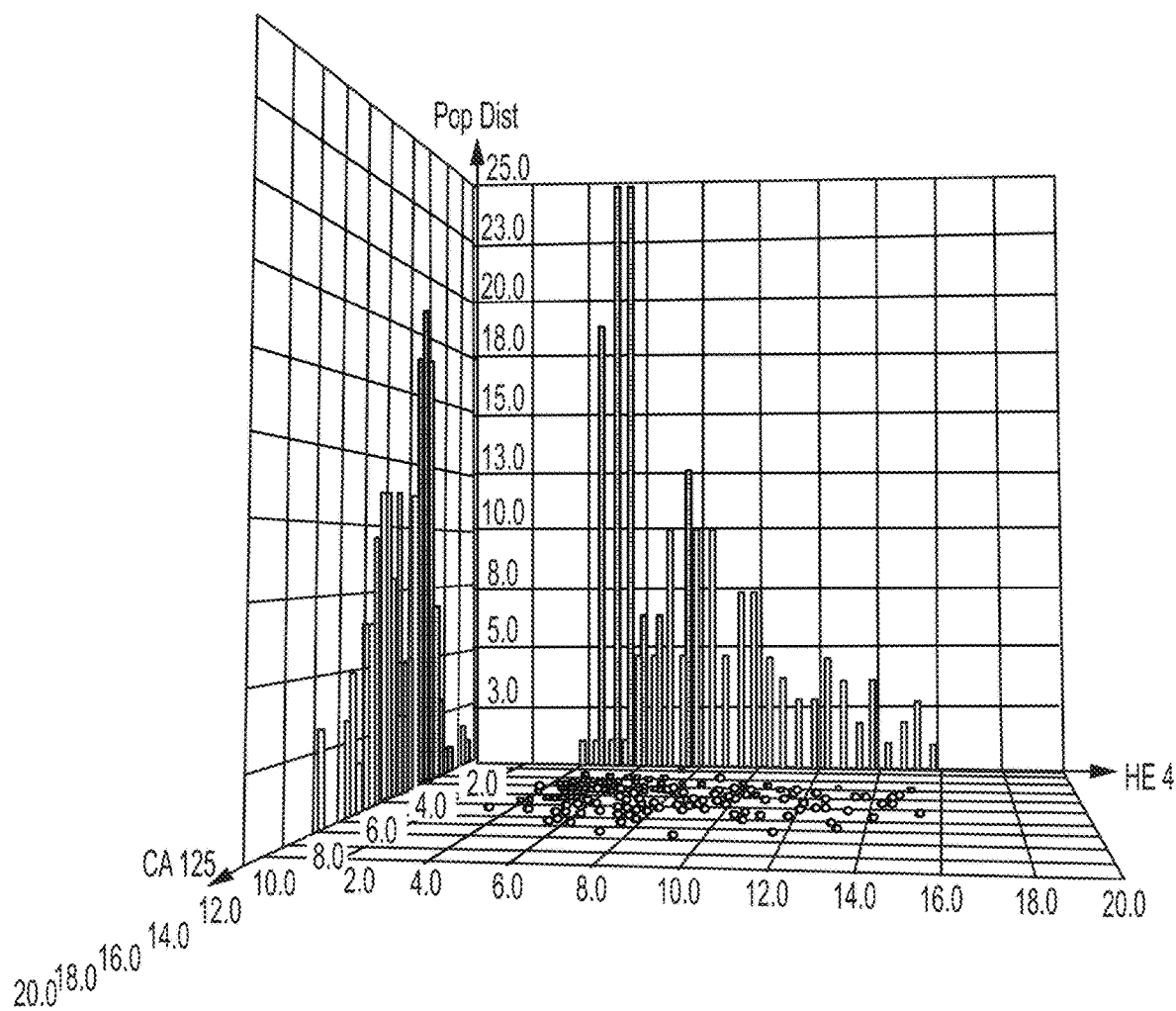
FIG. 13 is FIG. 12 rotated to show the population distribution of the HE 4 biomarker more clearly.
Figure 14:
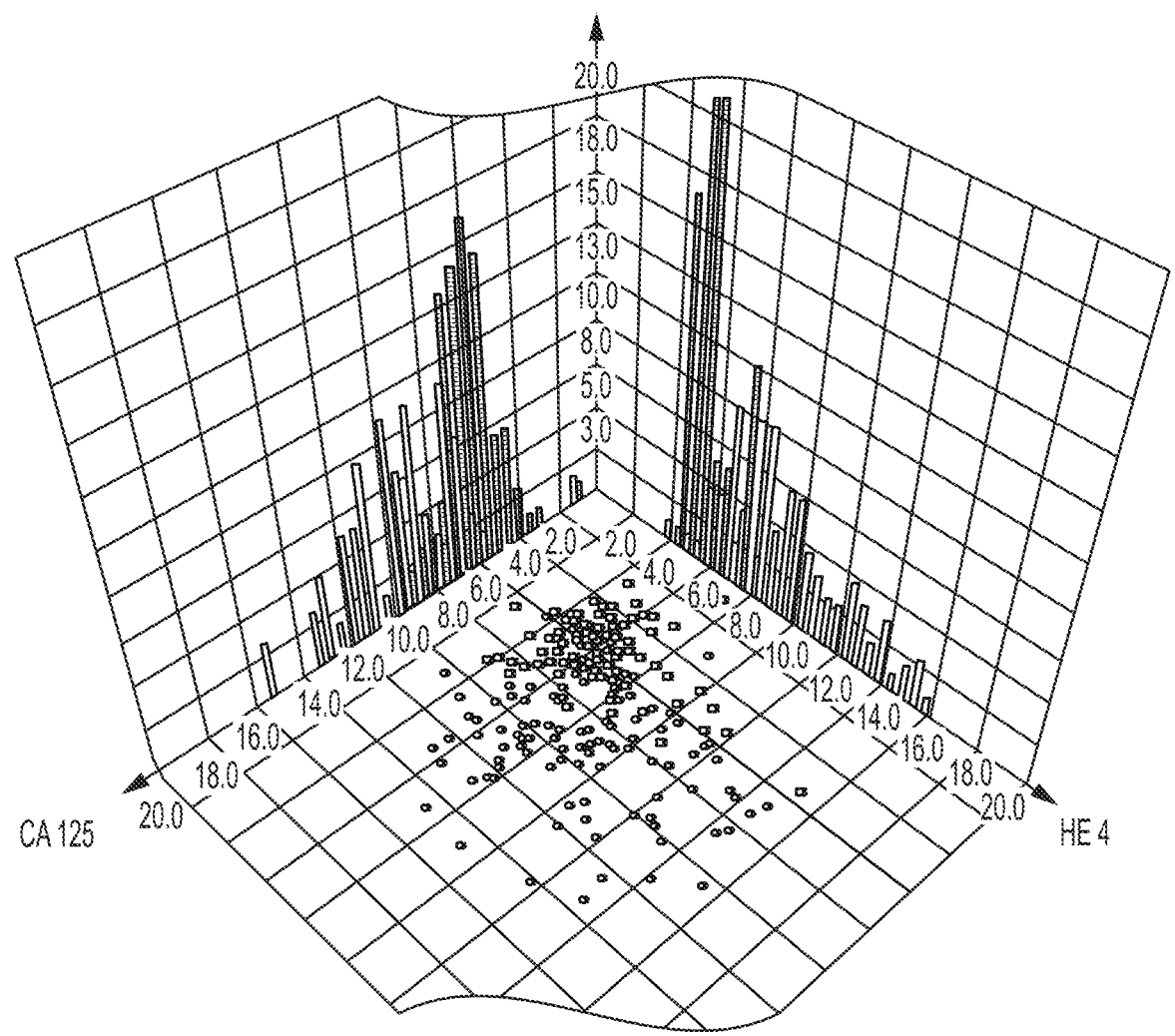
FIG. 14 is FIG. 12 rotated down to show the two axes distribution of these twp tumor marker more clearly.
Figure 15:
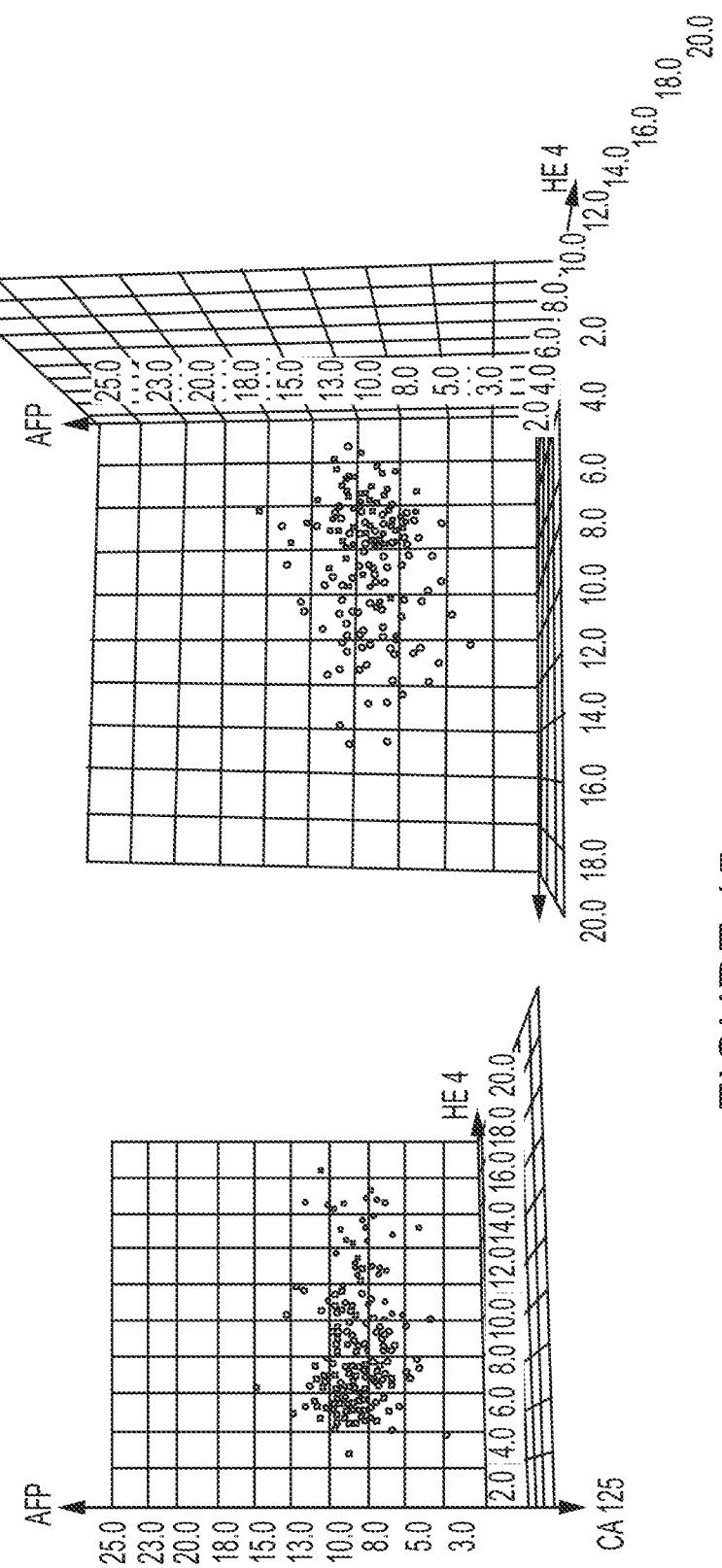
FIG. 15 shows CA 125, HE 4 and AFP tumor markers plotted in 3 D space.
Figure 17:
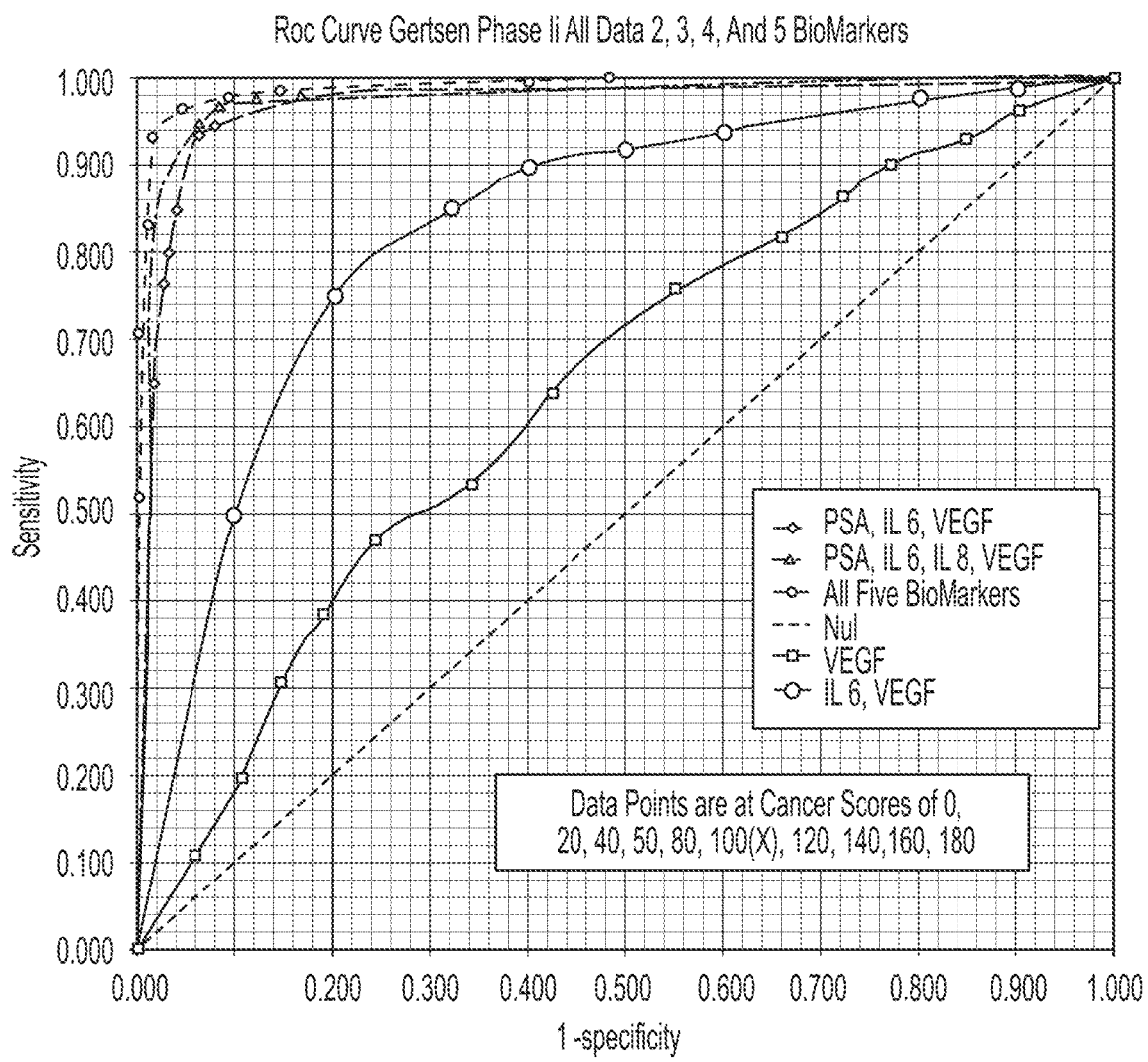
FIG. 17 shows the ROC curve for the breast cancer test discussed in this application.
Figure 18:
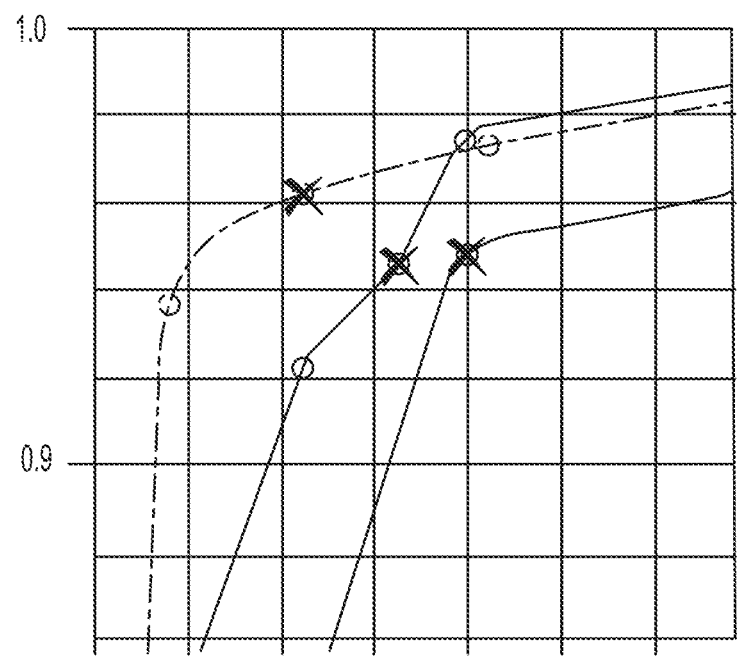
FIG. 18 shows the ROC curve in FIG. 17 blown up showing the scores near the upper left portion of the graph.

In contrast, FIGS. 12, 13 and 14 show population distribution of CA 125, HE4 for ovarian cancer, again on the horizontal axes and population distribution on the vertical axis. FIG. 13 shows these axes rotated down to see the orthogonal relationship of these biomarkers to each other. This 3D plot also shows the spatial distribution of these two markers when plotted on the horizontal 2-dimensional bi-marker plane (the vertical axis shows population distribution). The concentration is plotted as the normalized log concentration ranged from 1 to 20. CA 125 and HE4 are well known ovarian cancer biomarkers. In fact, for single high abundance protein cancer markers, these are very good. HE 4 is far better than PSA for prostate cancer in men. Yet they are not good enough for regulatory approval for screening. Even the combination of the two is not effective. Note that the single biomarker is relatively good for both. CA 125 will achieve about 50% specificity at 90% sensitivity. HE 4 will achieve about 45% specificity at 90% sensitivity. Notice that the orthogonal separation is not much different when viewed in two dimensions than for the single biomarker by itself. "HE4 a novel tumour marker for ovarian cancer: comparison with CA 125 and ROMA algorithm in patients with gynaecological diseases;" Rafael Molina, Jose M. Escudero, Jose M. Augé, Xavier Filella, Laura Foj, Aureli Tome, Jose Lejarcegui, Jaume Pahisa; Tumor Biology; December 2011, Volume 32, Issue 6, pp 1087-1095. FIG. 15 shows the addition of AFP, another general and ovarian cancer biomarker. No additional improvement is seen over CA 125 and HE 4. These three biomarkers are measuring similar aspects of the same thing and thus are not complimentary in improving predictive power when viewed with orthogonality maintained. The combined performance (using standard methods) is about the same as HE 4 by itself. FIG. 16 shows the ROC curves for CA125 and HE4 alone and then the combined ROC curve for the two when correlated to ovarian cancer. The combination is nearly an overlay of the HE 4 ROC curve. There is no improvement in performance at all (except a slight improvement for post-menopausal women). "HE 4 and CA 125 as a diagnostic test in ovarian cancer: prospective validation of the Risk of Ovarian Malignancy Algorithm;" T Van Gorp, I Cadron, E Despierre, A Leunen, F Amant, D Timmerman, B De Moor, I Vergote; Br J Cancer, Mar. 1 2011; 104(5) 863-870. The dramatic improvement in ROC curve using three, then four, and then all five biomarkers with this so-called orthogonal function characteristic, is shown in FIGS. 17 and 18. These plots all use the logarithm of the raw concentration, Note that if these raw concentrations were converted to Proximity Score and improvement would be seen as the orthogonal separation movement is enhanced when the Proteomic variance "noise" is removed. Shear probabilities indicate that a tumor biomarker for one cancer with a low response will likely have a higher response on an orthogonal axis, when this noise is suppressed.

Further separation occurs on this orthogonal grid by just the conversion to Proximity Score. FIGS. 5 and 6 show the data in FIG. 2 on the 3D plot where the vertical axis is the population distribution of each biomarker. The Proximity Score separates the sample data into two groups, populated by, mostly not-breast cancer close to the origin and breast cancer far away from the origin. These distributions are approximately Poisson. Notice the normal single biomarker overlap on each of the horizontal axes. No amount of mathematical manipulation can get rid of this problem. Notice however, that individual red (Breast Cancer) samples that are low on the pro-inflammatory axis (IL 6) tend to have a high position on the vascularization (VEGF) axis. The same is true of the other horizontal axis for (VEGF). Note that this separation will occur where functionally orthogonal biomarkers are used, or with tumor markers that do not have inherent orthogonal separation actions. Simple odds will dictate that a low level concentration for one of the tumor markers will very likely correspond with high levels for all the others in a cancer patient. For example, if a test panel includes 5 tumor markers (not orthogonal in action), the markers are measuring the same condition (e.g., a tumor is present). All the markers up regulate for the most part. If one marker has a poor response, for example is not present at levels typically found when up regulated, in an individual, it is likely that the others must also be active up regulating as well. This separation action is brought out when the Proteomic Variance (or noise) is dampened. Within the raw concentration values, this separation effect is contaminated by the noise. Note also that this separation keeps piling up through all, in this example, 5 orthogonal dimensions in the grid, whether the biomarkers are chosen for orthogonality of function or are just tumor makers that indicate the presence of the same tumor, with the orthogonality of function having by far the best separation. Note that each of these dimensions are associated with each biomarker selected. Thus, five biomarkers will require 5 dimensions, and 6 biomarkers requires 6 dimensions, etc.

The Spatial Proximity Method

The methods include a multi-dimensional space, one for each biomarker. The Proximity Score for each biomarker in the Training Set is plotted in the multi-dimensional space (5 dimensions in this breast cancer example). The plot is broken up into a grid, and then each point in this five dimensional grid is scored breast cancer or not-breast cancer by its closest proximity to several (5 to 15 percent) Training Set points on the grid. The cancer score is rendered by the count of breast cancer and not-breast cancer in the local vicinity of the empty grid point being scored. Maximum score is achieved in the empty grid point when it "sees" only breast cancer and vice-versa for not-breast cancer. Unknown samples are then placed on this grid and scored accordingly. Table 1 shows that combining this functional orthogonal selection of biomarkers with the Proximity Score Conversion (noise reduction and age normalization) yields predictive power of 96% for these biomarkers in this breast cancer case.

This can also be done on individual bi-marker slices through the 5-dimensional grid on each biomarker two dimensional plane to reduce computation time. This produces 10 so-called bi-marker planes. The 2-dimensional grid point is again scored by proximity to the training sets, disease or not-disease by the 2-dimensional proximity to the training set points. In this case, 3 to 10 percent of the closest data points are used for the proximity distance. This yields scores for each grid point. Grid points with a training set data point in it ignore the actual diagnosis of that training set point for the grid point score. The plane is then scored for predictive power, sensitivity and specificity by counting the training set points correct versus not correct by the usual definitions. The 10 resulting planes are then added up with an individual plane predictive power weighting. This weighting of each bi-marker plane is the predictive power (also sensitivity can be used) of that plane. The additive score of all ten planes is then shifted and gained to get a range from 0 to 200 with 0 to 100 labeled as not-cancer and 101 to 200 labeled as cancer. Unknown sample data points are then scored by their placement on these bi-markers planes by the predetermined scoring from the model build using the training sets.

ROC Curves for a Five-Biomarker Breast Cancer Diagnostic Test Panel

FIG. 17 shows the combined ROC curves for the full 5 test panel derived from the concentration values measured at the Gertsen Institute for cancer and not-cancer cohorts of 407 serum samples total. This overall plot, shows five ROC curves: 1) the black is VEGF alone; 2) the brown curve is for IL 6 and VEGF combined; 3) blue curve is for PSA, IL 6 and VEGF only; 4) the green curve is for PSA, IL 6, VEGF and IL 8 only; and 5) the red curve is for all five biomarkers. The buildup of predictive power is clear when looking at the cancer score set points corresponding to 100, the mid-point between the arbitrary 0 to 200 cancer score range. FIG. 18 shows this range of the ROC curve blown up to better see the improvement achieved with each added biomarker. The X mark is on the data point for the midpoint cancer score of 100. This would be the putative transition point from not-cancer to cancer. Though medical goals may shift this value. Oncologists have set the transition point at about 80 to minimize false negative predictions at the expense of false positives results. These data show all data set points, both the training set and the blind samples as well as data from a third party validation of the OTraces BC Sera Dx test kit for detecting breast cancer, for a total of 407 data sets. Note that the predictive power within the training set and the final predictive power scoring of the blind data set had about the same predictive power, about 97% to 98%. The reported cancer score in this case is an arbitrary scoring from 0 to 200 with 0 to 100 being not-cancer and 100 to 200 being cancer. Note that the red curve (all 5) does not terminate at the usual axis end points, 0, 0 and 1, 1. This is because a significant number of the data set points have a cancer score of exactly 0 and 200. 30% of the not-cancer samples have a score of 0 and about 50% of the cancer points have a score of 200. These points in the 5-dimensional grid only see respectively not-cancer for the 0 scores and cancer for the 200 score of the training set points in the grid. The proximity test uses the three closest points for the score computation on each 2-dimensional orthogonal cuts through the 5 dimensional space. These cuts are called bi-marker planes. The 5-dimensional space yields 10 discrete bi-marker planes. In the full five dimensions each blind sample is tested for proximity to about 20 to 25 different training set data points. These samples that score 0 or 200 see only not-cancer or cancer training set points, respectively in the grid. Thus they score respectively 0 and 200, the ends of the arbitrary range. The same is true, but to a lesser extent for the 3 and 4 biomarker curves. This demonstrates the robustness of the method.

Though these biomarkers have insufficient predictive power to be used as a screening test, combined they can achieve predictive power above 95%. However, this performance cannot be determined from individual ROC curves and the measurements of one biomarker's behavior. VEGF has the poorest performing ROC curve but when combined with the pro-inflammatory biomarker shows a very high boost in predictive power. This is due to amplifying effect of the orthogonal functions of these biomarkers. Furthermore, biomarkers with these features continue to amplify predictive power. This amplification can only be seen when the orthogonal information contained within the multiple functions is retained in the Spatial Proximity correlation method.

Assessing the performance of one biomarker by itself has limited value. They need to be assessed in a multi-dimensional format where coupling (or uncoupling) of functionality is maintained. Alternately, the biomarkers can be studied in an orthogonal matrix. This amplification of predictive power shown in these ROC curves comes directly from: 1) the suppression of Proteomics Variance by conversion to Proximity Score; 2) the use of biomarkers with Functional Orthogonality coupled with the Spatial Proximity correlation method; and 3) Normalization of the age drift inherent to the transition from not-disease to disease.

Age Normalization

The measured concentration distribution of VEGF in female humans is measured in about 400 patients in FIG. 3. VEGF is an anti-tumor low abundance cytokine that is up-regulated generally in serum with the presence of cancer but also up-regulates in other conditions as shown in Table 1. The vertical red and blue vertical bars show the population count (in percentage) for each concentration level shown on the horizontal axis in pg/ml (red is cancer and blue is not-cancer).

The red and blue horizontal bars across the top show the shift in population mean values for both not-cancer, blue and women with breast cancer, red as it varies with patient age. Notice, these mean values actually overlap. The not-cancer woman mean population value for age 65 is actually higher than the cancer mean value of a 35 year old women. This age shift is also seen in FIG. 1, the red and blue arrows the right side and bottom of the plot. This problem (for the correlation analysis) can occur with most if not all possible signaling proteins that could be useful in these analyses. See above for how this problem is rectified.

Age causes a complication to the above discussion as the population mean values for both not-cancer and cancer change with age. Additionally, using age as a separate independent variable in the correlation analysis does not improve predictive power. Thus, though the methods described above improve predictive power, age drift should be factored into it. Related provisional application 61/851,867 (and its progeny) describes how to use age as a meta-variable in the transformation of the concentration variables into age factored Proximity Score values. The discussion below describes methods to improve this transformation.

As outlined previously, methods for improving disease prediction can use an independent variable for the correlation analysis that is not the concentration of the measured analytes directly but a calculated value (Proximity Score) that is computed from the concentration but is also normalized for certain age (or other physiological parameters) to remove such parameter's negative characteristics such as age drift and non-linearities in how the concentration values drift or shift with the physiological parameter (age) as the disease state shifts from healthy to disease. This discussion provides improvements to that method.

One equation for conversion of concentration to Proximity Score discussed in the referred application is (see possible equations for the concentration to Proximity Score Conversion above):

$$PS_h = K^* \text{logarithm}_{10}((C_i/C_{(h)}) - (Cc/Ch))^2 + \text{Offset} \quad \text{Equation 1}$$

$$PS_c = K^* \text{logarithm}_{10}((C_i/Cc) - (Ch/Cc))^2 + \text{Offset} \quad \text{Equation 2}$$

Where:
$PS_h$+Proximity Score for not-cancer
$PS_c$=Proximity Score for cancer
K=gain factor to set arbitrary range.
$C_i$=measured concentration of the actual patient's analyte
$C_h$=patient age adjusted mean concentration of non-disease patients' analyte
$C_c$=patient age adjusted mean concentration of disease patients' analyte.
Offset=Ordinate offset to set numerical range (arbitrary)
This is referred to as equation 1 and 2 in the text below.

These equations selectively compress or expand measured concentration values to allow a better fit to the proximity correlation method. Age adjusted mean concentration values are used for the not-disease state and for the disease state. The method for age adjustment below shows that this improved method uses this equation and others in portions or zones on the graph showing the measured concentration and resultant Proximity Score that is actually used in the correlation analysis.

FIG. 19 shows Equation 1 and Equation 2 plotted showing the conversion from concentration to Proximity Score. Note that Equation 2 is inverted and reversed mathematically and its offset value is shifted such that the not-cancer equation (one) does not overlap the cancer equation (two) on the ordinate. The age related mean values are shown on the abscissa as the horizontal asymptotic curves not-cancer going to the left and cancer going to the right. These asymptotic curves vary with age again on the abscissa. In fact, for some markers, the age adjusted mean value for not-cancer and cancer overlap on the vertical axis, as shown on the figure. This aspect of the biology of this particularly deteriorates the predictive power if not dealt with. This embodiment shows Zone 1 folds onto Zone 2 and Zone 4 folded back on Zone 3 (see discussion on Population Distribution Bias). In the case of cancer versus not-cancer the cancer cohort is over represented in the training set by a large margin. The folding improves the distribution bias in the zones dominated by not-cancer FIG. 21 shows an alternate embodiment that uses a straight log concentration to linear conversion. In this scenario, $PS=M(\log(C_i))+B$, where PS=Proximity Score (the concentration), $C_i$=the measured concentration of the actual patient's analyte, M=the conversion slope, and B=the offset. Again, this embodiment shows Zone 1 folds onto Zone 2 and Zone 4 folded back on Zone 3.

The equations and resulting Proximity Score values are forced into zones on the two dimensional plot by adjusting the offset values. Furthermore, all individual samples at a particular age with actual measured values below that age mean values for not-cancer will be forced into zone 1. Likewise, all samples at a particular age with actual measured values above the mean value for cancer at that age are forced into zone 4. Similarly, samples with actual values between the mean value of not-cancer at that age at particular age and the midpoint between not-cancer and cancer mean values for that age are forced into zone 2, likewise for zone 3. In effect, the Proximity Score forces the individual sample of a certain age to take one of four positions based upon its relationship to the mean values for not-cancer and cancer for that age. The Proximity Score forces the concentration measurement to take sides. Note that this does not indicate that say a sample in zone 1 will be not-cancer. That depends on how the other four markers behave. The three key points not-cancer mean, cancer mean, and the derived midpoint between them, all vary independently on the abscissa and may overlap but are normalized in set zones or values on the ordinate (Proximity Score).

Figure 22:
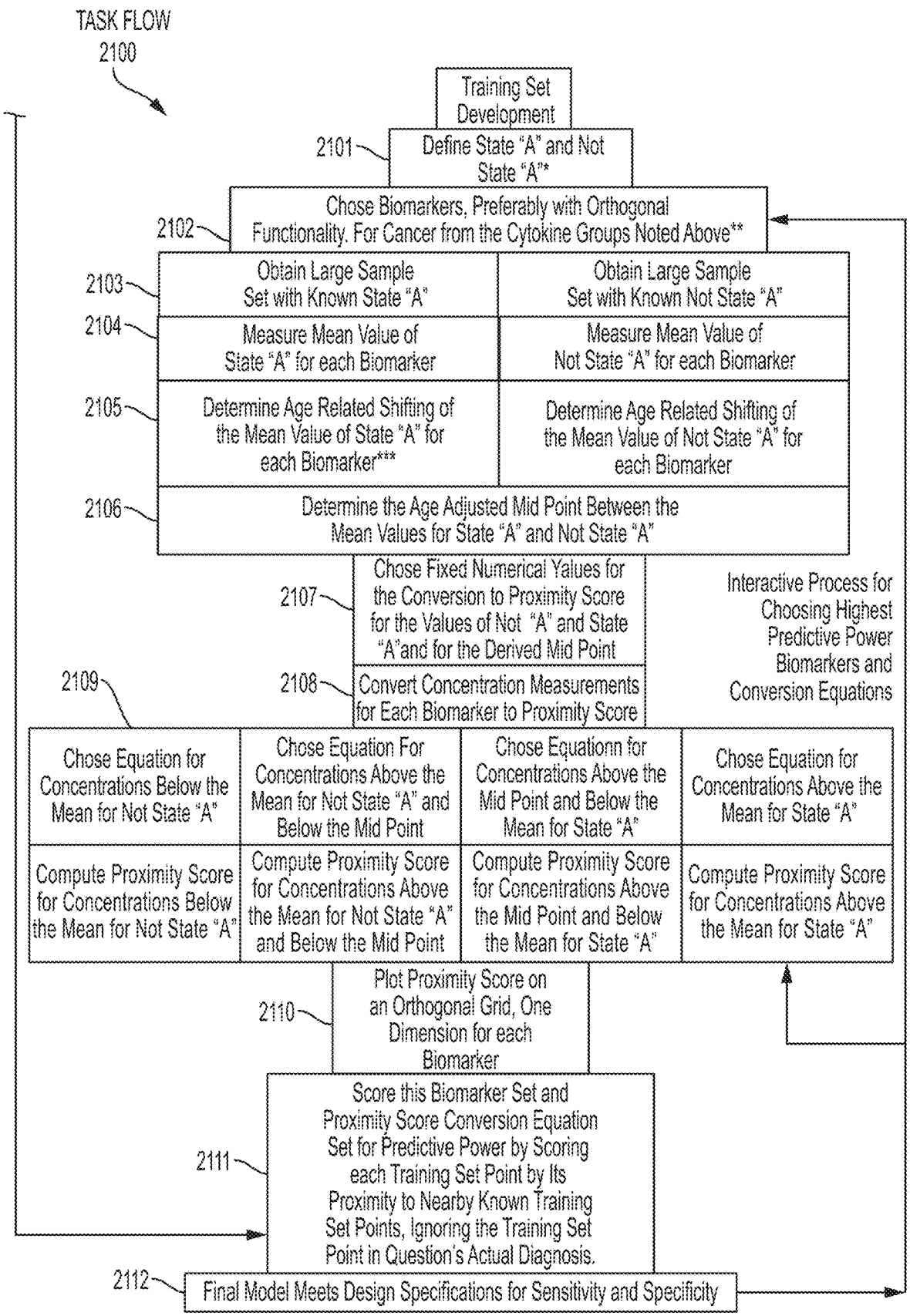
FIG. 22 shows a task flow chart for the construction of the Training Set Model.

FIG. 22 depicts an exemplary flow chart for Building Proteomic Noise Suppression Correlation Method. This flow chart describes the steps involved in developing a high performance correlation algorithm for separating two opposing conditions (state "A" and not-state "A") needed for diagnosis of either a disease state, a condition within a disease state related to severity or to determine the best population suitable for treatment of the disease with a particular drug. State "A" and Not-State "A" could be the presence of a disease and absence of the disease. Alternatively it could be a severe state of the disease and a less severe state of the disease. Also, it could be for scoring a particular drug or treatment modality for efficacy within a group of prospective patients. For cancer, the preferred cytokines with orthogonal functionality would be: pro-inflammatory, anti-inflammatory, Anti-tumor genesis, angiogenesis, and vascularization. Also at least one tumor marker would be appropriate. Age could a different independent variable. We term this variable the meta-variable. Note that age Body Mass index, race, and geographical territory among other independent variables are claimed in referenced patent PCT/US2014/000041.

An exemplary method is shown as 2100, "Task Flow." At step 2101, State "A", exemplarily the Disease State, and Not-State "A", exemplarily the Non-Disease State, are defined. At step 2102, biomarkers comprising the set are chosen, preferably those with orthogonal functionality. At step 2103, large sample sets of known State "A" and Not-State "A" are obtained. At step 2104, for State "A" and Not-State "A," the mean value for each biomarker is measured. At step 2105, for State "A" and Not-State "A," age-related shifting is calculated. At step 2106, the age-adjusted midpoint between the mean values for State "A" and Not-State "A" is calculated. At step 2107, the software calculates fixed numerical values for the conversion to Proximity Score for the mean values of Not-State "A" and State "A" and for the derived midpoint. At step 2108, the concentration measurements for each biomarker in the set are converted to a Proximity Score. At step 2109, the biomarker Proximity Scores for each biomarker in the set are used to compute concentration Proximity Scores and choose equations for concentration for State "A" and Not-State "A". At step 2110, the Proximity Score is plotted on an orthogonal grid, such that there is one dimension for each biomarker in the set. At step 2111, the biomarker set is scored, based on, for example, the Proximity Score Conversion Equation Set. This biomarker set score results in the highly predictive method for diagnosis discussed herein.

Negative Aspects of the Spatial Proximity Correlation Method

The Spatial Proximity Correlation method has very significant advantages over other methods in that it retains the orthogonal spatial separation inherent in these biomarkers as the transition from healthy to cancer occurs. However, the method may have several disadvantages that are not relevant to conventional analytical approaches that can be overcome. The method plots the training set data on a multidimensional grid and then scores other "blind" (not occupied) points on the grid for not-cancer or cancer by proximity to the training set points. The best correlation performance generally occurs if the movement of these biomarker data points is relatively linear. That is, if the movement or up/down regulation is highly non-linear or exhibits clumping with highly isolated points, degradation of the correlation may occur. Basically, highly isolated points on the grid will influence all nearby points with the scoring of the isolated point at the expense of others. A second problem is related to the relative general population distribution of the training set data and the real distribution of the disease in the general population. In the case of breast cancer, the general population distribution is about 0.5% cancer to 99.5% not-cancer. Yet the training set must be distributed 50%/50% or it will bias the correlation in favor of the side with higher population. No bias demands the 50%/50% split. This may cause areas with predominant not-cancer but low levels of cancer to over call cancer in these areas and vice versa.

Special Bias Problems with the Spatial Proximity Correlation Method and Human Biological Measurements FIG. 3 shows the population distribution of one of the biomarkers discussed for the cancer predictive test. This non-linear distribution with clumping and highly isolated data points is typical for all five of these biomarkers and most, if not all, of these low level signaling proteins (cytokines). This is indicative of the non-linear behavior of the immune system. This problem (and the age shift effect described above) significantly decays the ability to correlate these proteins to disease state predictions. This example is intended to teach how to correct this non-linear up regulation behavior.

In FIG. 3, the concentration distribution is highly non-linear with blocks of concentration values at extremely low levels as well as very high levels. This is an indication of the non-linear behavior of the immune system. This behavior is common to all of these cytokine or signaling based biomarkers. In fact, the biomarkers used in this breast cancer detection method discussed herein all look very similar to the plot in FIG. 3. Also note that the distribution shows isolated points in between the clumps. This will cause a correlation bias we term "Local Spatial Distribution Bias." Both of those deficiencies are partially mitigated with the use of Equations 1 and 2, as disclosed above.

Local Spatial Distribution Bias

Figure 23:
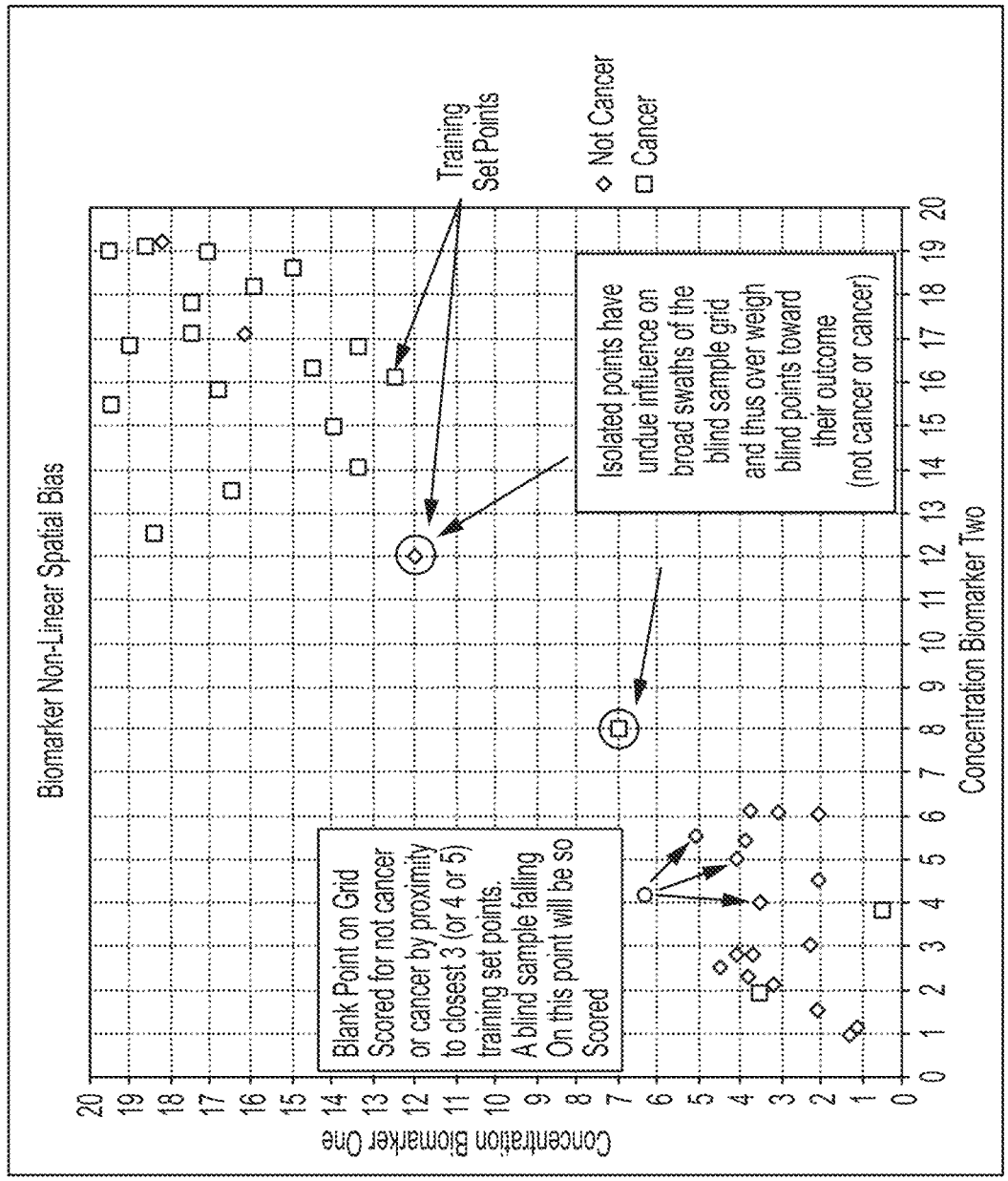
FIG. 23 shows a stylized Proximity Score distribution with large non-linear distributions

As noted above, this problem is partially mitigated by the use of Equations 1 and 2, though there may be many other possible solutions. FIG. 23 shows a stylized two dimensional biomarker plot showing cancer at high levels and dispersed. Also, not-cancer is shown at lower levels and compacted. Isolated points between these clumps are also shown. The standard deviation of the spacing of the plot points on this graph is about 8 units. Note that the two isolated points on the graph will sweep up large sections of the proximity plot forcing these areas with the isolated point's diagnosis.

Figure 24:
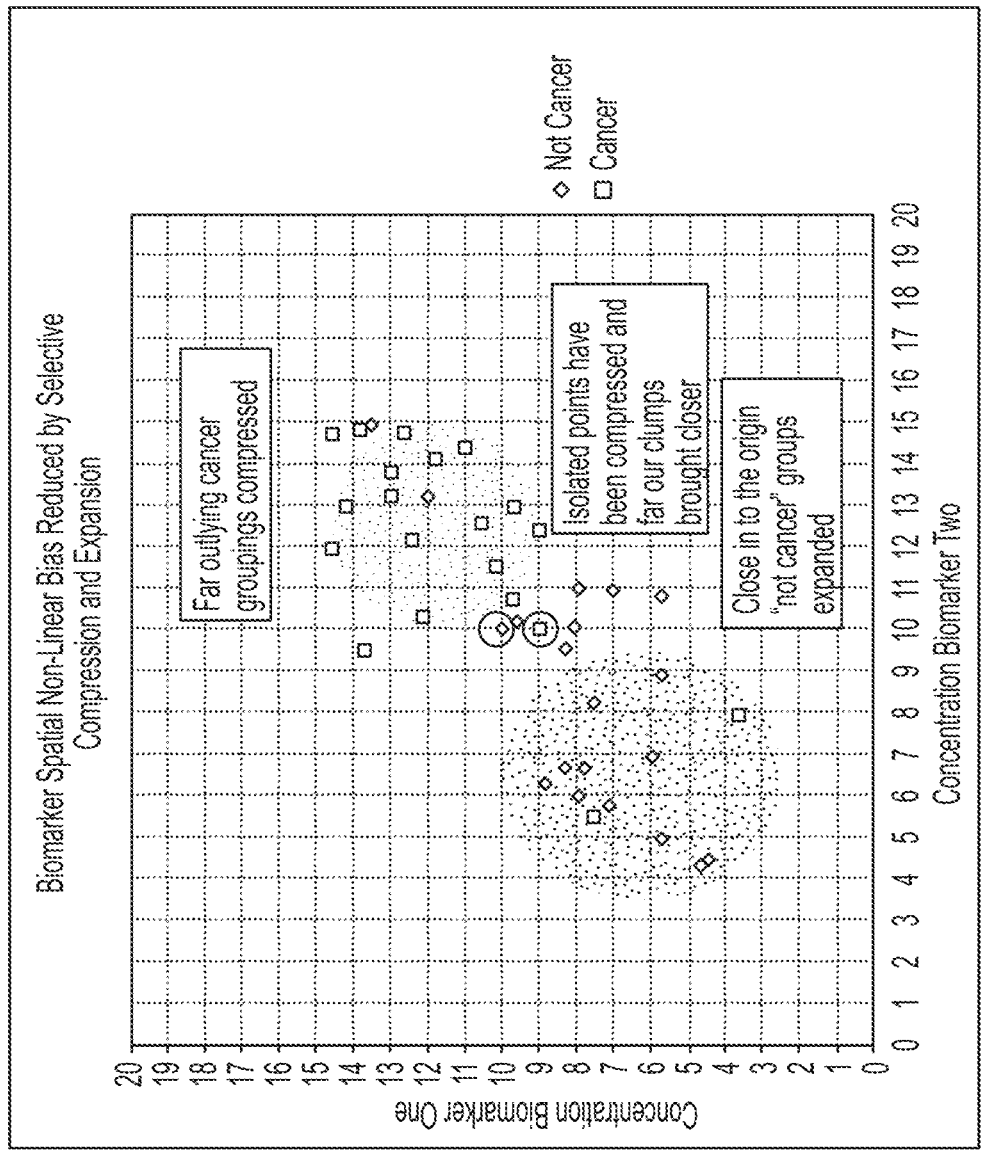
FIG. 24 shows a stylized Proximity Score distribution with the large non-linear distributions suppressed.

FIG. 24 shows these same points conditioned by the compression and expansion performed by Equations 1 and 2. The standard deviation between points on this graph is about 2.5 and the clustering and isolation are very much reduced. This mathematical manipulation is perfectly acceptable under the rules noted above under the discussion of the measurement science. Indeed, the distance standard deviation reduction is a good rule of thumb for predictive power of the model. Note the standard deviation of the spacing is reduced to only 3 units. This spacing deviation should be as low as possible without shifting the spacing order.

Population Distribution Local Bias

Figure 25:
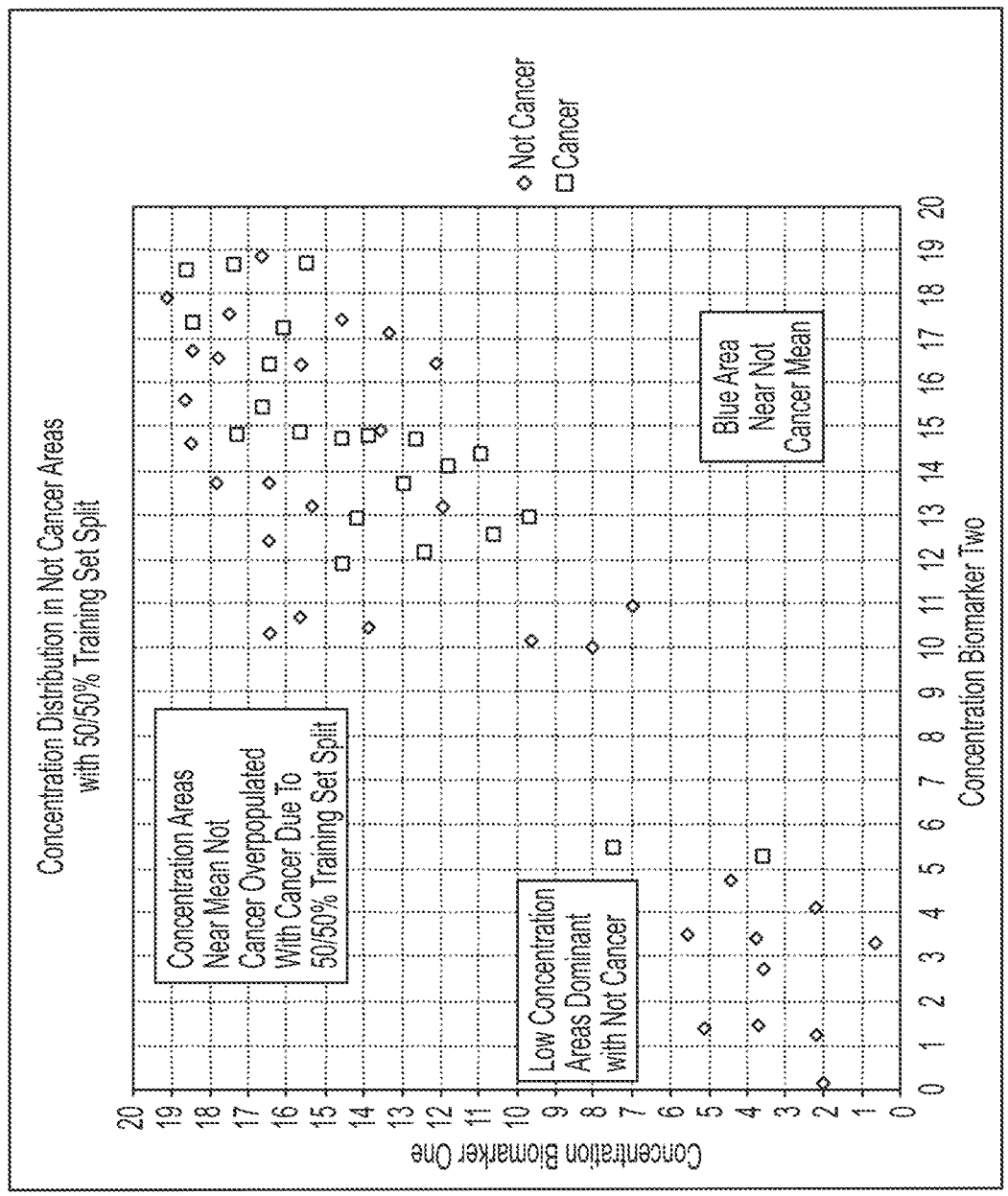
FIG. 25 shows a stylized Proximity Score distribution with a 50% to 50% disease to not disease distribution as required by the Training Set.
Figure 26:
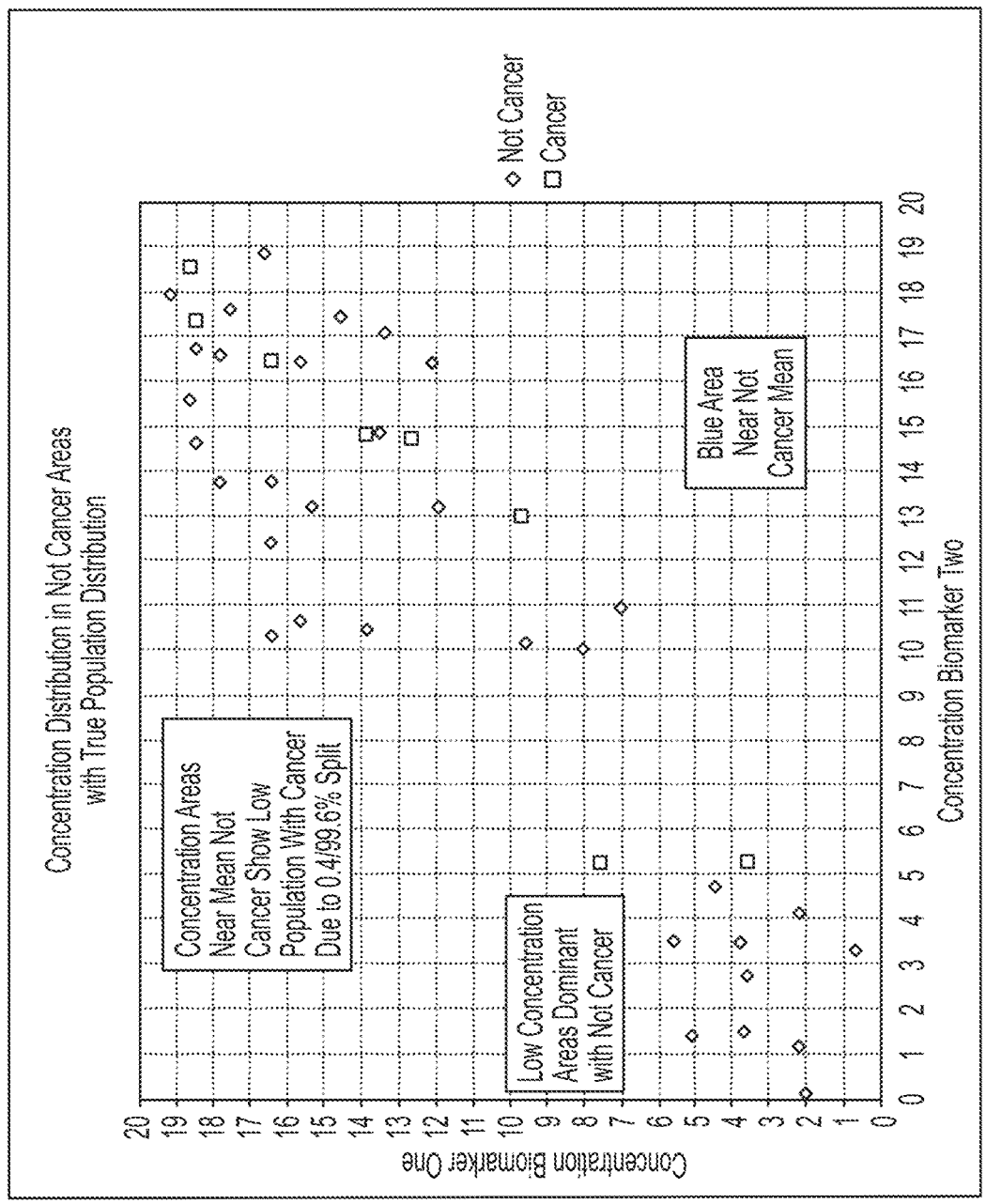
FIG. 26 shows a stylized Proximity Score distribution with a disease to not disease true distribution.
Figure 27:
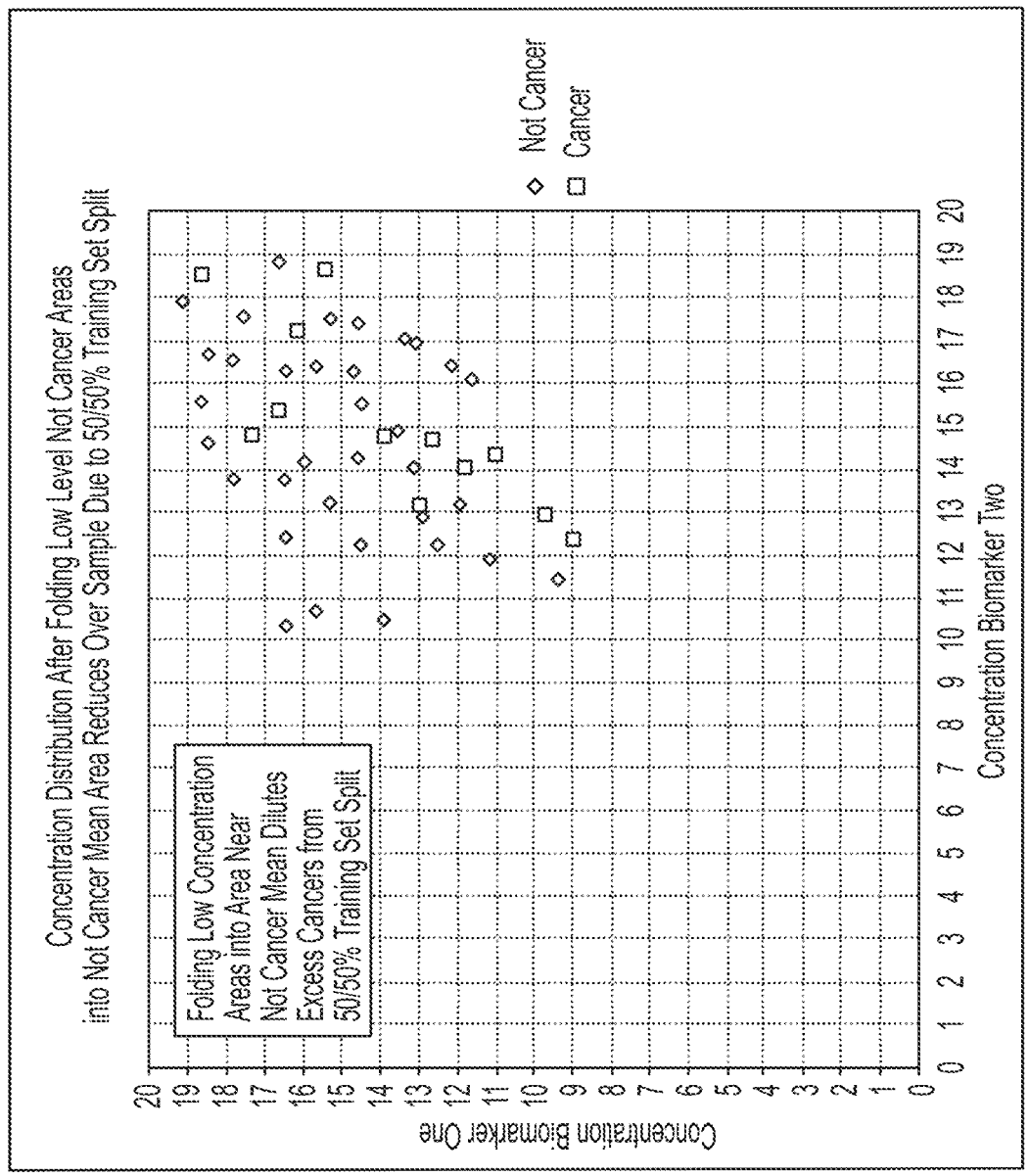
FIG. 27 shows a stylized Proximity Score distribution with a disease to not disease true distribution corrected by folding.

FIGS. 25, 26, and 27 show how this issue can be mitigated. FIG. 25 shows the over representation of cancer in the not-cancer space for samples below the age related mean value for not-cancer. The area in the upper right will generally be over samples with cancer. The samples in the lower left are dominated by not-cancer and thus are more correct. FIG. 26 shows how the plot would look if properly represented by the real lesser distribution of cancer. These are at risk of bias and can be mitigated to a degree by folding the lower right area up into the areas near the age related mean value for not-cancer. These very low concentration values, well below 1 pg/ml, are populated into the higher concentration area, helping mitigate the bias. The stylized plot showing the folding and reduced local population distribution bias is shown in FIG. 27.

The mathematical rules are:
1) The training set model should be populated by 50% not-cancer and 50% cancer to remove model bias.
2) Mathematical manipulations are acceptable for reducing the effect of the physical characteristics of the independent measurement to reduce the effect of extraneous informant noise provided the methods are applied to both the training set model and the blind samples to be tested.

Using simple logistic regression with these biomarkers for breast cancer will yield predicative power of slightly less than 80%. Using simple standard Spatial Proximity correlation without the age and non-linearity corrections (simple logarithm of concentration) yields about 89% predictive power. These improvements discussed above: 1) age normalization; 2) local spatial distribution bias corrections; and 3) population distribution local bias corrections, yields about 96% predictive power with these biomarkers. Adding correction of blind samples for topology instability (see provisional application No. 61/851,867 (and its progeny)) can add another 1 to 2% improvement.

Spatial Bias and Population Distribution Bias Corrections are Complementary to the Variance (Noise) Suppression Methods The methods discussed above for correcting two bias problems associated with the Spatial Proximity Correlation method are complimentary to solving the problem of Proteomics variance (noise). The correction methods both involve compressing the raw concentration data, and this compression is toward the predetermined mean values for disease and not-disease. In fact, correcting the population bias problem involves folding the very low concentration values (well below the not-disease mean) into an area near or even above the not-disease mean. The same is true of the very high concentration values.

Figure 28:
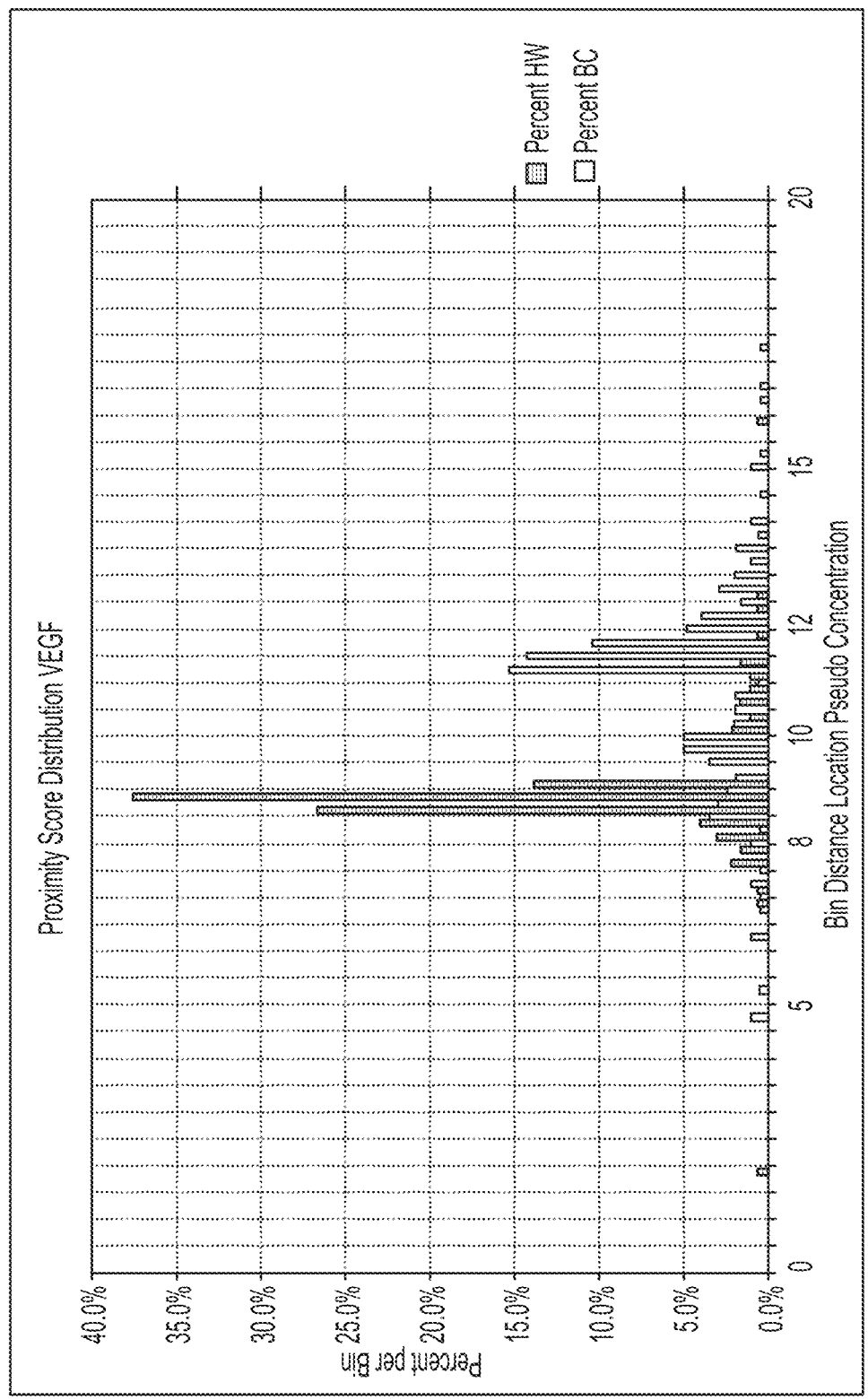
FIG. 28 shows the resulting population distribution after conversion for biomarker VEGF.

The resulting Proximity Score distribution of this method is shown in FIG. 28 for VEGF. The other four look similar. The process forces sample data points into two roughly overlapping Poisson distributions where not-cancer predominates on the lower side and cancer predominates on the upper side. Note that the cancer and not-cancer samples still overlap. One biomarker simply cannot completely separate healthy from disease with a high degree of accuracy. The equation used in this example causes an inversion of the order of the concentration values when transitioned into a Proximity Score, in zones above and below the age adjusted mean values of concentration for cancer and not-cancer, respectively. There are two cases discussed here. The first case is where zones 1 and 2 are above the mean value for not-disease and below the midpoint; and where zones 3 and 4 are above the midpoint but below the mean value for disease. The second case is where the zones are staged sequentially on the Proximity Score axis, with the mean for not-disease placed between zones 1 and 2; the mean for disease placed between zones 3 and 4 and the derived midpoint between zones 2 and 3. The first case has been used in situations where the population distribution of the not-disease and disease are in disparity (e.g., breast cancer—not-breast cancer is 0.5% and 99.5%, respectively which reflects a Local Population Bias). The second case has been used where the population distribution is closer to the training set distribution (e.g., aggressive/non-aggressive prostate cancer).

Note that now the mean value age transitions for not-cancer, midpoint and cancer mean values are each a single vertical line at the ordinate axis. Also note that the very low and very high values are logarithmically compressed and the values near the age related mean values are expanded somewhat. On the inversion, it is important to note that keeping the linear order is not important in the proximity correlation method, simply the proximity relations must be maintained. In other words, the order can be inverted. The compression and expansion normalizes the grand or overall distribution of the data but the close in spatial relations are maintained. This is termed removing spatial bias. The method removes negative spatial bias and smearing of the data due to age or other physiological variables, e.g. body mass index. In essence, the training set sample data points are forced to take positions in one of the 4 zones: 1) below age related mean for not-cancer; 2) between age related mean for not-cancer and the midpoint transition to cancer; 3) above the midpoint transition and below the age related mean for cancer; and 4) above the age related mean for cancer regardless of age or spatial distribution non-linearities.

Note that several other equations could be used in this method as long as the spatial biased is dealt with. Simple log compression from low concentrations to the age related mean for not-cancer, and for high concentrations above the age related mean for cancer and perhaps a sigmoid equation between these mean values. It is not possible to a priori determine what equation relationships for this transition, and the best fit must be determined by experiment and comparison of results via overall multi-marker ROC curves. The best equation depends on the character of the spatial bias.

Summary of Analytical Steps

1) Chose biomarkers that have a functional relation to the disease of interest. The fact that the biomarker may have very poor disease predictive power (poor ROC curve) cannot eliminate it for consideration as two poor biomarkers with a large independent action in the transition from not-disease to disease may produce a very large amplification of predictive power. These biomarkers should have a functional distinction on their actions.

2) Carefully define the disease and not-disease cohorts for the Training Set. These sets should mimic the population that the test will be administered to. Unrelated non-conditions unrelated to the disease should not be eliminated. Nonmalignant conditions that are within the population should be statistically correct for both the cancer and not-cancer cohorts.

Measure the mean values of concentration for each cohort with sufficient age sampling to accurately determine how the age affects the mean values.

4) Convert the raw concentration values into the Proximity Score. On a two axis plot, this transformation will encompass forcing all raw concentration values equal to or very near the respective mean values onto a fixed but different (separated) numerical values on the Proximity Score axis regardless and independent of the samples age. Also, the raw concentration values at or very near the calculated midpoint in concentration between the not-disease and disease mean values must be mathematically forced to a fixed value on the Proximity Score axis regardless of the samples age. The midpoint Proximity Score Point should be between the low not-disease (usually) and high disease fix points on the proximity Score axis. This location arrangement is usually desirable but may not always be (e.g., a biomarker that up regulates at low ages but down regulates at higher ages may require a different strategy for Proteomics Variance suppression).

5) Mathematically compress or expand (or other) the raw concentration data such that it lands in its proper place regarding its relationship to the mean values at it age (make the solders line up by rank). While applying the Spatial Proximity Correlations method, adjust or experiment with the mathematical schema to maximize predictive power with the training set group. There are not a priory rules and the mathematical schema that meets the diagnostic goals will change depending on the character, non-linearly and complexity of the raw measurement involved in the transition from not-disease to disease. *The Complexity Paradox* (Kenneth L. Mossman, Oxford University Press, 2014), the challenges faced by Proteomic Investigators are aptly summarized: "the non-linear dynamics inherent in complex biological systems leads to irregular and unpredictable behaviors"

6) Use the exact same mathematical schema to compute disease scores on a test population that is equivalent to the target population for the test. Determine if this validation sample set meets diagnostic criterion.

Discussion of Current Methods Using Tumor Markers

A typical example of research into serum based tests for detecting cancer using tumor markers includes the work published in the International Journal of Molecular Sciences entitled, "A Bead-Based Multiplexed Immunoassay to Evaluate Breast Cancer Biomarkers for Early Detection in Pre-Diagnostic Serum". "Sensitivity of CA 15-3, CEA and Serum HER2 in the Early Detection of Recurrence of Breast Cancer." Pedersen AC1, SØrensen P D, Jacobsen E H, Madsen J S, Brandslund I. Dept. of Clin. Biochem., Lilleb ALT Hospital, Vejle, Denmark. This study focused on 5 well known breast cancer tumor markers; cancer antigen 15-3, (CA15-3), carcinoembryonic antigen (CEA), cancer antigen 125 (CA-125), cancer antigen 19-9 (CA19-9), a-fetoprotein (AFP), as well as several markers with putatively non-cancer functions, leptin, migration inhibitory factor (MIF)), osteopontin (OPN), haptoglobin), and prolactin. This study concluded that none of these markers were effective in detecting early stage breast cancer either individually or in combination, but could be useful in detecting metastasis. Table 2, below, shows each cancer bio-marker and its functional characteristics. There are 5 tumor markers, two possible pro-inflammatory markers and the other have unclear functionality related to either the immune systems reaction to the presence of cancer and/or the tumors signaling action on the body.

TABLE 3 is a list of tumor or biomarkers used in cancer diagnostic proteomics

| Biomarker | Functional Description | Orthogonal Functionality |
|---|---|---|
| CA15-3 (U/mL) | Breast Cancer Antigen, it is found on the surface of many types of cancer cells and shed into the blood stream. | No |
| CEA (ng/mL) | Breast and Other Cancer Antigen, describes a set of glycoproteins involved in cell adhesion. CEA is normally produced in gastrointestinal tissue during fetal development, but the production stops before birth. Therefore CEA is usually present only at very low levels in the blood of healthy adults. However, the serum levels are raised in some types of cancer, which means that it can be used as a tumor marker in clinical tests. | No |
| CA-125 (U/mL) | Breast and Other Cancer Antigen, Mucin 16 is a membrane associated mucin that possesses a single transmembrane domain.[5] A unique property of MUC16 in its large size. MUC16 is more | No |

TABLE 3-continued is a list of tumor or biomarkers used in cancer diagnostic proteomics

| Biomarker | Functional Description | Orthogonal Functionality |
|---|---|---|
| | than twice as long as MUC1 and MUC4 and contains about 22,000 amino acids, making it the largest membrane associated mucin. | |
| CA19-9 (U/mL) | Breast Cancer Antigen 19-9, or sialylated Lewis (a) antigen) is a tumor marker that is used primarily in the management of several cancers | No |
| AFP (ng/mL) | Breast and Other Cancer Antigen, AFP is the most abundant plasma protein found in the human fetus. It is thought to be the fetal forth of serum albumin. Plasma levels decrease rapidly after birth but begin decreasing prenatally starting at the end of the first trimester. The function of AFP in adult humans is unclear. However, the serum levels are raised in some types of cancer, which means that it can be used as a tumor marker in clinical tests. | No |
| Leptin (ng/mL) | The "satiety hormone"; is a hormone made by fat cells which regulates the amount of fat stored in the body. It does this by adjusting both the sensation of hunger, and adjusting energy expenditures and Hunger is inhibited. The identification of the mechanistic links between obesity and cancer progression is emerging as a topic of interest. | fat; functional connection to cancer action is unclear |
| MIF (pg/mL) | Macrophage migration inhibitory factor (MIF), an inflammatory cytokine, is over expressed in many solid tumors and is associated with poor prognosis. | inflammatory |
| Haptoglobin (mg/mL) | In blood plasma, haptoglobin binds free hemoglobin (Hb) released from erythrocytes with high affinity and thereby inhibits its oxidative activity. Haptoglobin level is used to determine whether hematology needs to be consulted for hemolytic anemia. Elevated haptoglobin levels is associated with epithelial ovarian cancer. | Mostly associated with hemolytic anemia, functional connection to cancer action unclear |
| Prolactin (ng/mL) | Much of the literature on human breast cancer and prolactin (PRL) appears to be contradictory. PRL has been first recognized as a hormone that plays an important role in breast cancer initiation and development in rodents, and, at least partly, in humans | Lactation, functional connection to cancer action unclear |
| osteopontin (ng/mL) | Osteopontin (OPN) is expressed in a range of immune cells, including macrophages, neutrophils, dendritic cells, and T and B cells, with varying kinetics. OPN is reported to act as an immune moduiator in a variety of manners. It has chemotactic properties, which promote cell recruitment to inflammatory sites. (OPN) has been recognised as important in the processes of tumorigenicity and metastasis. | Inflammatory |

Table 3 is a list of tumor or biomarkers used in cancer diagnostic proteomics

The referenced publication refers to methods for data mining from large data sets. Principle Component Analysis (PCA) and Random Forest (RF) are methods for data mining from, especially, large data sets to learn of connections from the data to outcomes. This is useful for the situation shown in the table where there are a number of components with unknown connections to the other components and the outcomes being measured. These methods will illuminate the connections, if any, that work. These methods are not useful for the correlations described herein. We know the connection, or lack thereof, between components (independent variables) and the outcomes. These discussions concern a way to greatly improve the correlation between these variables and their characteristics and the outcomes.

Devices and Reagents Used for this Cancer Validation Study

Traces CDx Instrument System

The test data included below and for much of the work discussed above was measured on the devices and with the reagents noted below. The data was processed on the OTraces LIMS system, or in some cases calculations were completed on PC based software. All of the computational software was written and validated by OTraces, Inc.

The CDx Instrument System is based upon the Hamilton MicroLab Starlet system. It is customized with programming to transfer the OTraces immunoassay methods to the Hamilton high speed ELISA robot. The Hamilton Company is a well respected company that sells automated liquid handling systems worldwide, including the MicroLab Starlet. The unit is customized by Hamilton for OTraces to provide for full automation. OTraces CDx System includes an integral Microplate Washer System and Reader. These two additional devices allow the system to complete one full run of all five immunoassays in the test panel in one shift with no operator intervention after initial setup. The system as configured will complete 40 cancer scores per day. Enhancements include software to conduct one target analyte at a time. This is needed to be able to rerun a specific test when an error occurs within a full test run.

BC Sera Dx Test Kit

This test kit includes all of the reagents and disposable devices to perform 120 cancer test scores, including all buffers, block solutions, wash solution, antibodies and calibrators. Enhancements needed to fully commercialize this test kit include adding two control samples. These controls provide independent validation that a "blind" test sample yields a proper cancer score. The two controls are designed to produce a proximity score of 50 and 150 respectively. The LIMS system (see below) QC program will verify that these controls are correct thus validating the individual test runs in the field. The test kits are built in a GMP factory and have received the CE mark. The microtiter plates are pre-coated at the factory with the capture antibody and protein blocking solutions.

Laboratory Information Management System (LIMS)

Clinical chemistry systems marketed today, e.g. by Roche and Abbott, all include a graphical interface with software sufficient to manage patient data, quality control the instrument and chemistry operations and facilitate test sample identification and introduction to the test system. These menus are integrated into the delivered chemistry system. OTraces' business model is to include these functions on OTraces computer servers located at OTraces' US facilities and connect the CDx instrument integrally to these servers through the Internet using cloud computing. This yields several significant advantages: 1) The LIMS software incorporates FDA compliant archival software such that data from all test runs from each CDx system deployed in the field are run on the OTraces servers. Applying feedback from the installed base, and input from key institutions about patient outcomes allows OTraces to collect FDA compliant data for US based FDA market clearance submissions. 2) Preferably, bar coded reagent packaging allows the instrument and LIMS to connect all QC test results from the factory QC test. These data are available in real time as the tests are run in the field for further validation of the field test results. 3) The CDx System will only run OTraces validated reagents and thus test runs using non OTraces reagents will not be possible. This system appears as a typical user interface to the operator with all functions running in real time and patient reports are available as soon as the test run is complete.

Breast Cancer Prediction Summary

This report documents the performance of the correlation computation method for predicting the stage of breast cancer for the breast cancer positive samples from both the Phase I and II Gertsen studies. The two studies had 186 samples diagnosed with breast cancer. Of these 29 were stage 3 (or 4), 86 were stage 2 and 71 were stage 1 or 0. Only 4 samples were diagnosed as Stage 0, which is not enough samples to develop a proper correlation algorithm, so these were grouped with stage 1. Also, only one was diagnosed with stage 4 and this was grouped with the stage 3 diagnoses. When sufficient samples are obtained, the staging algorithm will be able to separate these stages also. Out of the 186 total samples diagnosed by biopsy to have breast cancer by the Gertsen Institute, the staging correlation algorithm miscalled one sample as stage 1 whereas the Gertsen Institute diagnosed this sample as Stage 2 (99.5% Predictive Power).

Gertsen Phase I Validation Study

The Gertsen Phase I Validation Study was conducted at the Gertsen Institute in November of 2010 and was to assess the performance of the OTraces BC Sera Dx test kit and the OTraces LHS Instrument System, for assessing the risk of the presence of breast cancer. The LHS Chemistry System is a semi-automated liquid handling system to process the BC Sera Dx Breast Cancer Detection Test kit. The test kit measures the concentrations of five very low level cytokines and tissue markers and calculates a score for assessing the risk. The proteins measured are IL-6, IL-8, VEGF, TNFα and PSA. The experiment consisted of measuring 100 patient samples split 50% with breast cancer diagnosed by biopsy and 50% putatively healthy (only 97 were actually collected by the Institute). The cancer scoring results of this project were equivocal as 100 samples is not enough to complete a full training set model. The Institute also indicated to OTraces that they felt the Instrument was not automated enough nor was its throughput fast enough for the intended task, screening women for cancer. The LHS system was designed for the early stage research and was not considered by OTraces management sufficient for production and market release.

Gertsen Phase II Validation Study

The Gertsen Phase II project was conducted at the Gertsen Institute in November of 2012, to assess the performance of the OTraces BC Sera Dx test kit and OTraces CDx Instrument System for assessing the risk of the presence of breast cancer. The CDx Instrument system is the upgraded chemistry system intended for market release. It is based upon the high speed ELISA robot, the MicroLab Starlet developed and marketed by the Hamilton Company. The test kit measures the concentrations of five very low level cytokines and tissue markers and calculates a score for assessing the risk. The proteins measured are IL-6, IL-8, VEGF, TNFα and PSA. The experiment consisted of measuring 300 patient samples split roughly 50% with breast cancer diagnosed by biopsy and 50% putatively healthy. For the Phase II project, the biopsy results were disclosed to OTraces for 200 samples divided exactly into 50% healthy and cancer and divided into specified age groupings. These results were used for a training set to develop a model that is predictive of the disease state. The remaining blind samples, 112, were then processed through the model for resultant cancer score and these scores were then disclosed to the Gertsen Institute. These blind sample scores were then analyzed by the Gertsen Institute to assess the accuracy of the OTraces prediction.

Results of Cancer Prediction Study of Combined Phase I/Phase II

Phase II training set model now has processed 209 blind samples from the Gertsen Phase I study (run as blinds) and the Gertsen Phase II study, (blinds) with a combined false negative and positive rate of 2%, or a predictive power of 98%.

Prediction of Breast Cancer Staging from BC Sera Dx Test Data Recovered from the Gersten I and II Validation Studies A correlation Model for predicting the stage of breast cancer has been developed by OTraces. This algorithm is not the same as the models used to predict the healthy or breast cancer state. The mathematics of the Training Set Models is designed to separate training set data into two states, usually "STATE A" and "NOT-STATE A" (e.g., breast cancer and not-breast cancer). As such, the model does not directly predict the cancer stage in breast cancer patients. The breast cancer versus healthy score, from the cancer scoring model, will not accurately estimate cancer stage, and it will not achieve high predictive power for staging. The degree of increase in scoring in the cancer/healthy model is not based upon how bad the cancer is but is based upon the degree of proximity of the training set data points to the blind sample positions in the 5-dimensional grid. Thus, a stage 0 cancer could score 200 (0 to 100 score healthy and 100 to 200 score breast cancer) if it sits on a point in the 5-dimensional grid that is surrounded by other training set data that are cancerous and no points that are healthy. Indeed, the four stage 0 cases in this model score above 190 on the healthy versus cancer scoring model. This is indicative that the stage 0 cases are strongly differentiated from healthy and in the healthy/cancer model are surrounded by mostly cancer cases.

In order to use the correlation method to predict cancer stage of cancer samples from the BC Sera Dx test kit, OTraces constructs three models. These models follow the binary directive of the correlation model for "STATE A" and "NOT-STATE A". Thus the three models are predictive for the groups of staging include: 1) Stage 1 versus Stage 2 and 3; 2) Stage 2 versus Stage 1 and 3; and 3) Stage 3 versus Stage 1 and 2. These three models create a matrix of scores giving the probability each sample falling on either side of the three cases. This matrix can then be de-convoluted to determine the predicted breast cancer stage.

Other Applications of the Cancer Staging Method

This technique for breaking the disease into sub-states, where the signal (disease) and offset (not-disease) are redefined to be conditions within the diagnosed state of the disease are certainly possible. The most obvious example would be to break prostate cancer down into its two medically relevant states aggressive, Gleason score 8 and up to 10, and non-aggressive, Gleason score of 7 and lower. Currently, the Gleason score is determined at biopsy. Medically, men with low Gleason score perhaps should not be treated, but the medical problem is that these men can convert to aggressive prostate cancer and the only reliable way to detect this today is with another biopsy. This is nether pleasant for the patient and is medically difficult. Using this method can solve this unmet medical need by providing a simple and easy to administer blood test.

The methods described herein may also be applied with equal efficacy to five other solid cancer tumors, as shown in Table 3 below. As evidenced by Table 3, the methods of the present invention are useful in the diagnosis of any solid tumor.

TABLE 4

| Condition | Status | Cohort | % Correct | Falsely Identified | Test Location |
|---|---|---|---|---|---|
| Breast Cancer | Cancer | 651 | 96.9% | 3.1% | U.S. |
| | Not Cancer | 529 | 97.5 | 2.5 | U.S. |
| | Cancer | 200 | 97.0 | 3.0 | Russia[(2)] |
| | Not Cancer | 207 | 96.6 | 3.4 | Russia[(2)] |
| Prostate Cancer | Cancer | 111 | 96.4 | 3.6 | U.S. |
| | Not Cancer | 148 | 96.6 | 3.4 | U.S. |
| Ovarian Cancer | Cancer | 101 | 96.0 | 4.0 | U.S. |
| | Not Cancer | 111 | 99.1 | 0.9 | U.S. |
| Melanoma | Cancer | 172 | 98.3 | 1.7 | U.S. |
| | Not Cancer | 172 | 97.7 | 2.3 | U.S. |
| Lung Cancer | Cancer | 96 | 100.0 | 0.0 | U.S. |
| | Not Cancer | 96 | 97.9 | 2.1 | U.S. |

Applications Beyond Cancer

The described method can be used in any diagnostic application where two or more biomarkers are required to diagnosis a single condition where the diagnostic description is the patient sample either has the disease or not. Table 4, below, lists a number of conditions that have been evaluated using the herein described methods.

TABLE 5

| Condition | Predictive Power Expected/Achieved | Number of Biomarkers |
|---|---|---|
| Conditions Beyond Cancer | | |
| Alzheimer's Disease | >90% | 4 to 5 |
| Lyme's Disease | >90% | 5 |
| Premature Birth | >92% | 5 |
| Miscarriage | >92% | 5 |
| Macular Degeneration | >94% | 5 |
| Cardiomyopathy | 90% | 5 |
| Myocardial infarction | >90% | 5 to 6 |
| Rheumatoid Arthritis | >90% | 5 |
| Diabetes | >90% | 5 |
| Multiple Sclerosis | >90% | 5 |
| Amyotrophic Lateral Sclerosis | >90% | 5 |
| Parkinson's Disease | >92% | 4 to 5 |
| Auto-immune Disease | >90% | 5 |
| Drug Efficacy Testing | | |
| Macular Degeneration | >95% | 5 |
| nephrotoxin actions | >95% | 5 |
| Cancer | >95% | 5 |
| Cytotoxins | >92% | 4 to 5 |
| Vaccines | >92% | 4 to 5 |
| Immune Stimulators | >95% | 5 |

The methods can also be used to segregate drugs into groups wherein a drug is efficacious or not. This can be used to rescue drugs that have failed in clinical trials due to poor statistics, or used a priory to increase the success rate of the trial.

While certain exemplary embodiments have been described above in detail and shown in the accompanying drawing figures, it is to be understood that such embodiments are merely illustrative of and not restrictive of the broad invention. In particular, it should be recognized that the teachings of the invention apply to a wide variety of biological states and diseases, as well as to stages of diseases. Persons of skill in the art will recognize that various modifications may be made to the illustrated and other embodiments of the invention described above, without departing from its broad inventive scope. Thus, it will be understood that the invention is not limited to the particular embodiments or arrangements disclosed, but is rather intended to cover any changes, adaptations or modifications which are within the scope and spirit of the invention as defined by the appended claims.

The invention claimed is:

1. A computer-implemented method for using an evaluative model to indicate a probability of a disease state for a metabolic disease in a patient under examination, the method comprising:
   receiving a first set of concentration values of a first analyte from a first set of samples from patients with a not-disease diagnosis for the metabolic disease;
   receiving a second set of concentration values of the first analyte from a second set of samples from patients with a disease diagnosis for the metabolic disease, wherein the first set and second set of samples comprise a training set of samples;
   calculating a mean value of concentration of the first analyte from the first set of concentration values;
   calculating a mean value of concentration of the first analyte from the second set of concentration values;
   computing a midpoint value of concentration between the mean value of the first set of concentration values and the mean value of the second set of concentration values;
   calculating a first proximity score representing the mean value of concentration of the first set of analytes, said calculation comprising normalizing age drift in transition between the disease state for the metabolic disease and non-disease state for the metabolic disease and dampening outlier concentrations in the training set of samples;
   calculating a second proximity score representing the mean value of concentration of the second set of analytes, said calculation comprising normalizing age drift in transition between the disease state for the metabolic disease and non-disease state for the metabolic disease and dampening outlier concentrations in the training set of samples;
   deriving a midpoint proximity score representing the derived midpoint of the mean values of concentration of the first and second sets of analytes; and
   mapping the concentrations of the training set of samples into a range of proximity scores between the first proximity score and the second proximity score to complete the evaluative model, wherein the evaluative model diagnoses the disease state for the metabolic disease of a patient under examination; and
   administering a treatment for the diagnosed disease state for the metabolic disease of the patient under examination in accordance with the disease state diagnosed by the evaluative model, wherein the metabolic disease diagnosed is at an initial stage.

2. The computer implemented method of claim 1, wherein the training set of samples includes at least one of blood samples, urine samples, and tissue samples.

3. The computer-implemented method of claim 1, wherein the calculated mean value for concentration for the first set of samples and for the second set of samples is age-adjusted.

4. The computer-implemented method of claim 1, wherein the training set of samples includes an equal number of disease samples and not-disease samples.

5. The computer implemented method of claim 1, wherein mapping the concentrations of the training set of samples includes mapping the concentrations into proximity score zones, wherein the proximity zones further comprise:
- a first zone with proximity scores corresponding to a concentration of the first analyte higher than the mean value of concentration of the first set of samples and lower than the mid-point; and
- a second zone with proximity scores corresponding to a concentration of the first analyte higher than the mid-point and lower than the mean value of concentration of the second set of samples.

6. The computer implemented method of claim 1, wherein calculating a range of proximity scores further comprises:
- mapping concentrations of the training set of samples below the first proximity score; and mapping concentrations of the training set of samples above the second proximity score, wherein the mapping of concentrations of the training set of samples creates proximity score zones.

7. The computer implemented method of claim 6, wherein mapping the concentrations of the training set of samples comprises mapping the concentrations into proximity score zones, wherein said proximity score zones further comprise:
- a first zone with proximity scores corresponding to a concentration of the first analyte lower than the mean value of concentration of the first set of samples;
- a second zone with proximity scores corresponding to a concentration of the first analyte higher than the mean value of the first set of samples but lower than the midpoint value of concentration and wherein the second zone is located next to the first zone;
- a third zone with proximity scores corresponding to a concentration of the first analyte higher than the midpoint value of concentration and lower than the mean value of the second set of samples and wherein the third zone is located next to the second zone; and
- a fourth zone with proximity scores corresponding to a concentration of the first analyte higher than the mean value of the concentration of the second set of samples and wherein the fourth zone is located next to the third zone.

8. The computer implemented method of claim 1, wherein the mapping of the
- concentrations of the training set of samples into the range of proximity scores further comprises:
- inverting a range of concentration values of the training set of samples as the concentrations are mapped into the range of proximity scores.

9. The computer implemented method of claim 1, wherein the mapping of the
- concentrations of the training set of samples into the range of proximity scores further comprises:
- at least one of compressing and expanding a range of concentration values of the training set of samples as the concentrations are mapped into the range of proximity scores.

10. The computer-implemented method of claim 1, further comprising:
- performing steps a-i recited in claim 1 for a second analyte;
- mapping the concentrations of the training sets of samples for the first analyte and the second analyte into an orthogonal multi-dimensional grid, wherein the axes of the grid include the concentration of the first analyte, the concentration of the second analyte, and the proximity scores of the first analyte and the second analyte;
- dividing the multi-dimensional grid into grid sections boxes to be scored for the disease; and
- scoring each individual grid section box in the multi-dimensional grid based upon the proximity of each grid section box to a predetermined number of training set samples.

11. The computer-implemented method of claim 10, further comprising: compiling multi-dimensional grid scores at each training set location point; and calculating a raining set accuracy score based upon the compiled multi-dimensional grid scores.

12. The computer-implemented method of claim 10, wherein the predetermined number of training set samples includes about five to fifteen percent (5-15%) of the closest training set samples to each box.

13. The computer-implemented method of claim 12, wherein scoring each individual box in the multi-dimensional grid includes:
- calculating a count number of about five to fifteen percent (5-15%) of the closest training set samples that are samples from patients with a disease diagnosis for the metabolic disease;
- calculating a count number of about five to fifteen percent (5-15%) of the closest training set samples that are samples from patients with a not-disease diagnosis for the metabolic disease;
- comparing the determined count numbers; and
- scoring each individual box in the multi-dimensional grid as disease or not-disease based upon the comparison of the determined count numbers.

14. The computer-implemented method of claim 10, wherein the predetermined number of training set samples includes about three to ten percent (3-10%) of the closest training set samples to each box.

15. The computer-implemented method of claim 10, wherein scoring each individual box in the multi-dimensional grid further comprises:
- slicing the multidimensional grid into planes that are coincident with the axes of the first analyte concentration and proximity score and the second analyte concentration and proximity score;
- calculating a count number of about three to ten percent (3-10%) of the closest training set samples that are samples from patients with a confirmed disease diagnosis for the metabolic disease;
- calculating a count number of about three to ten percent (3-10%) of the closest training set samples that are samples from patients with a not-disease diagnosis for the metabolic disease;
- comparing the determined count numbers;
- scoring each two-dimensional box in each of the planes as disease or not-disease based upon the comparison of the determined count numbers;
- calculating a plane score for each of the planes based on the scoring of each two-dimensional box in each of the planes; and
- calculating a total probability of a disease state score by combining the plane scores.

16. The computer-implemented method of claim 15, further comprising:
- applying a weighting factor to each of the plane scores.

17. The computer-implemented method of indicating the probability of a disease state of claim 1, further comprising:
- normalizing the indication of the probability of a disease state for the metabolic disease based on the age of the patient under examination.

18. The computer-implemented method of claim 17, further comprising:
- calculating mean values of concentration of the first analyte for a predetermined number of ages of patients with the not-disease diagnosis for the metabolic disease and for a predetermined number of ages of patients with the confirmed disease diagnosis for the metabolic disease; and
- converting the determined values of concentration to proximity scores, wherein the proximity scores do not have an age related bias.

19. The computer-implemented method of claim 18, wherein determining mean values of concentration of the first analyte for a predetermined number of ages of patients with the not-disease diagnosis for the metabolic disease and for patients with the confirmed disease diagnosis for the metabolic disease further comprises:
- normalizing a concentration-age shift in the mean values; and
- normalizing the midpoint value of concentration between the mean value of concentration of the first analyte for patients with the confirmed disease diagnosis for the metabolic disease and the mean value of concentration of the first analyte for patients with the not-disease diagnosis for the metabolic disease.

20. The computer-implemented method of claim 19, wherein the training set of samples includes samples from patients within a predetermined range of ages.

21. The computer implemented method of claim 1, further comprising administering a second drug in conjunction with the anti-cancer drug as a combination therapy.

22. The computer implemented method of claim 1, wherein the metabolic disease is diabetes.

23. A method of treatment for a metabolic disease comprising:
- receiving a first set of concentration values of a first analyte from a first set of samples from patients with a not-disease diagnosis for the metabolic disease;
- receiving a second set of concentration values of the first analyte from a second set of samples from patients with a disease diagnosis for the metabolic disease, wherein the first set and second set of samples comprise a training set of samples;
- calculating a mean value of concentration of the first analyte from the first set of concentration values;
- calculating a mean value of concentration of the first analyte from the second set of concentration values;
- computing a midpoint value of concentration between the mean value of the first set of concentration values and the mean value of the second set of concentration values;
- calculating a first proximity score representing the mean value of concentration of the first set of analytes;
- calculating a second proximity score representing the mean value of concentration of the second set of analytes;
- deriving a midpoint proximity score representing the derived midpoint of the mean values of concentration of the first and second sets of analytes;
- mapping the concentrations of the training set of samples into a range of proximity scores between the first proximity score and the second proximity score to complete the evaluative model;
- receiving concentration values for the first set of analytes and concentration values for the second set of analytes from a patient under examination;
- diagnosing the disease state for the metabolic disease of a patient under examination using the evaluative model; and
- administering a treatment for the disease state for the metabolic disease diagnosed by the evaluative model, wherein the metabolic disease diagnosed is at an initial stage.

24. The method of claim 23, wherein further comprising administering a second drug in conjunction with the anti-cancer drug as a combination therapy.

25. The method of claim 23, wherein the metabolic disease is diabetes.

* * * * *